(12) United States Patent
Salafsky et al.

(10) Patent No.: US 9,428,789 B2
(45) Date of Patent: Aug. 30, 2016

(54) CLASSIFICATION OF KINASE INHIBITORS USING NONLINEAR OPTICAL TECHNIQUES

(75) Inventors: Joshua S. Salafsky, San Francisco, CA (US); Ryan McGuinness, Tiburon, CA (US)

(73) Assignee: BIODESY, INC., South San Francisco, CA (US)

( * ) Notice: Subject to any disclaimer, the term of this patent is extended or adjusted under 35 U.S.C. 154(b) by 0 days.

(21) Appl. No.: 14/006,302

(22) PCT Filed: Mar. 21, 2012

(86) PCT No.: PCT/US2012/030010
§ 371 (c)(1),
(2), (4) Date: Dec. 24, 2013

(87) PCT Pub. No.: WO2012/129347
PCT Pub. Date: Sep. 27, 2012

(65) Prior Publication Data
US 2014/0113312 A1    Apr. 24, 2014

Related U.S. Application Data

(60) Provisional application No. 61/454,868, filed on Mar. 21, 2011, provisional application No. 61/595,123, filed on Feb. 5, 2012.

(51) Int. Cl.
*C12Q 1/48* (2006.01)
*G01N 33/58* (2006.01)
*G01N 33/68* (2006.01)

(52) U.S. Cl.
CPC ............. *C12Q 1/485* (2013.01); *G01N 33/58* (2013.01); *G01N 33/6803* (2013.01); *G01N 2500/00* (2013.01)

(58) Field of Classification Search
None
See application file for complete search history.

(56) References Cited

U.S. PATENT DOCUMENTS

| | | |
|---|---|---|
| 3,253,065 A | 5/1966 | Hansen |
| 3,847,909 A | 11/1974 | Schickfluss et al. |
| 4,619,879 A | 10/1986 | Kakuta et al. |
| 4,708,871 A | 11/1987 | Geysen |
| 4,739,044 A | 4/1988 | Stabinsky |
| 4,757,141 A | 7/1988 | Fung et al. |
| 4,775,637 A | 10/1988 | Sutherland et al. |
| 4,818,710 A | 4/1989 | Sutherland et al. |
| 4,833,092 A | 5/1989 | Geysen |
| 4,844,613 A | 7/1989 | Batchelder et al. |
| 4,978,503 A | 12/1990 | Shanks et al. |
| 4,997,928 A | 3/1991 | Hobbs, Jr. |
| 5,001,209 A | 3/1991 | Wreesmann et al. |
| 5,143,854 A | 9/1992 | Pirrung et al. |
| 5,145,790 A | 9/1992 | Mattingly et al. |
| 5,156,810 A | 10/1992 | Ribi |
| 5,215,899 A | 6/1993 | Dattagupta |
| 5,223,409 A | 6/1993 | Ladner et al. |
| 5,231,191 A | 7/1993 | Woo et al. |
| 5,236,826 A | 8/1993 | Marshall |
| 5,244,813 A | 9/1993 | Walt et al. |
| 5,250,264 A | 10/1993 | Walt et al. |
| 5,252,494 A | 10/1993 | Walt |
| 5,298,741 A | 3/1994 | Walt et al. |
| 5,320,814 A | 6/1994 | Walt et al. |
| 5,324,591 A | 6/1994 | Georger, Jr. et al. |
| 5,324,633 A | 6/1994 | Fodor et al. |
| 5,376,556 A | 12/1994 | Tarcha et al. |
| 5,389,482 A | 2/1995 | Okano et al. |
| 5,403,484 A | 4/1995 | Ladner et al. |
| 5,427,908 A | 6/1995 | Dower et al. |
| 5,432,018 A | 7/1995 | Dower et al. |
| 5,432,610 A | 7/1995 | King et al. |
| 5,485,277 A | 1/1996 | Foster |
| 5,498,530 A | 3/1996 | Schatz et al. |
| 5,498,538 A | 3/1996 | Kay et al. |
| 5,512,490 A | 4/1996 | Walt et al. |
| 5,521,289 A | 5/1996 | Hainfeld et al. |
| 5,556,762 A | 9/1996 | Pinilla et al. |
| 5,571,689 A | 11/1996 | Heuckeroth et al. |
| 5,580,717 A | 12/1996 | Dower et al. |
| 5,599,627 A | 2/1997 | Aoki et al. |
| 5,624,821 A | 4/1997 | Winter et al. |
| 5,627,024 A | 5/1997 | Maruyama et al. |

(Continued)

FOREIGN PATENT DOCUMENTS

| | | |
|---|---|---|
| EP | 0740156 A1 | 10/1996 |
| EP | 0873520 B1 | 10/2002 |
| EP | 0941474 B1 | 3/2006 |
| EP | 1798555 A1 | 6/2007 |
| JP | 11119270 A | 4/1999 |
| WO | WO 84/03506 A1 | 9/1984 |
| WO | WO 84/03564 A1 | 9/1984 |
| WO | WO 98/51435 A1 | 11/1988 |
| WO | WO 90/05317 A1 | 5/1990 |

(Continued)

OTHER PUBLICATIONS

U.S. Appl. No. 60/253,862, filed Nov. 29, 2000, Salafsky.

(Continued)

*Primary Examiner* — Suzanne M Noakes
(74) *Attorney, Agent, or Firm* — Wilson Sonsini Goodrich & Rosati

(57) ABSTRACT

A method is disclosed for classifying and distinguishing between type I and type II kinase inhibitors. The method involves the use of non-linear optical techniques, in particular second-harmonic generation (SHG) to identify conformational changes in kinase proteins obtained from known type I or type II inhibitors. The method further involves deducing the manner of binding of unknown inhibitors by comparison with the signal changes produced by known ligands. The method is also applied to comparing the conformational changes induced by the binding of generic and branded kinase inhibitor drugs to a target kinase.

18 Claims, 6 Drawing Sheets

(56) References Cited

U.S. PATENT DOCUMENTS

| | | |
|---|---|---|
| 5,631,734 A | 5/1997 | Stern et al. |
| 5,633,724 A | 5/1997 | King et al. |
| 5,648,260 A | 7/1997 | Winter et al. |
| 5,652,060 A | 7/1997 | Uchida et al. |
| 5,663,143 A | 9/1997 | Ley et al. |
| 5,696,157 A | 12/1997 | Wang et al. |
| 5,698,426 A | 12/1997 | Huse |
| 5,723,286 A | 3/1998 | Dower et al. |
| 5,723,323 A | 3/1998 | Kauffman et al. |
| 5,734,018 A | 3/1998 | Rutter et al. |
| 5,750,373 A | 5/1998 | Garrard et al. |
| 5,763,192 A | 6/1998 | Kauffman et al. |
| 5,766,905 A | 6/1998 | Studier et al. |
| 5,770,434 A | 6/1998 | Huse |
| 5,800,992 A | 9/1998 | Fodor et al. |
| 5,814,524 A | 9/1998 | Walt et al. |
| 5,821,060 A | 10/1998 | Arlinghaus et al. |
| 5,834,758 A | 11/1998 | Trulson et al. |
| 5,847,400 A | 12/1998 | Kain et al. |
| 5,962,248 A | 10/1999 | Tadano et al. |
| 6,023,540 A | 2/2000 | Walt et al. |
| 6,025,601 A | 2/2000 | Trulson et al. |
| 6,030,787 A | 2/2000 | Livak et al. |
| 6,040,586 A | 3/2000 | Slettnes |
| 6,055,051 A | 4/2000 | Eisenthal |
| 6,084,991 A | 7/2000 | Sampas |
| 6,095,555 A | 8/2000 | Becker et al. |
| 6,096,497 A | 8/2000 | Bauer et al. |
| 6,110,426 A | 8/2000 | Shalon et al. |
| 6,121,983 A | 9/2000 | Fork et al. |
| 6,124,102 A | 9/2000 | Fodor et al. |
| 6,134,002 A | 10/2000 | Stimson et al. |
| 6,180,415 B1 | 1/2001 | Schultz et al. |
| 6,194,222 B1 | 2/2001 | Buechler et al. |
| 6,204,067 B1 | 3/2001 | Simon et al. |
| 6,228,326 B1 | 5/2001 | Boxer et al. |
| 6,284,197 B1 | 9/2001 | Abbott et al. |
| 6,410,245 B1 | 6/2002 | Northrup et al. |
| 6,455,303 B1 | 9/2002 | Orwar et al. |
| 6,456,423 B1 | 9/2002 | Nayfeh et al. |
| 6,576,478 B1 | 6/2003 | Wagner et al. |
| 6,682,942 B1 | 1/2004 | Wagner et al. |
| 6,699,719 B2 | 3/2004 | Yamazaki et al. |
| 6,753,200 B2 | 6/2004 | Craighead et al. |
| 6,775,003 B2 | 8/2004 | Ivarsson |
| 6,780,584 B1 | 8/2004 | Edman et al. |
| 6,882,420 B2 | 4/2005 | Rassman et al. |
| 6,917,726 B2 | 7/2005 | Levene et al. |
| 6,953,694 B2 | 10/2005 | Salafsky et al. |
| 7,013,054 B2 | 3/2006 | Levene et al. |
| 7,023,547 B2 | 4/2006 | Venkatasubbarao et al. |
| 7,033,764 B2 | 4/2006 | Korlach et al. |
| 7,045,337 B2 | 5/2006 | Schultz et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,105,310 B1 | 9/2006 | Gray et al. |
| 7,108,970 B2 | 9/2006 | Levinson |
| 7,126,688 B2 | 10/2006 | Rassman et al. |
| 7,181,122 B1 | 2/2007 | Levene et al. |
| 7,193,711 B2 | 3/2007 | Rassman et al. |
| 7,233,391 B2 | 6/2007 | Schermer et al. |
| 7,262,866 B2 | 8/2007 | Ivarsson |
| 7,292,742 B2 | 11/2007 | Levene et al. |
| 7,316,769 B2 | 1/2008 | Craighead et al. |
| 7,336,359 B1 | 2/2008 | Simpson et al. |
| 7,336,389 B2 | 2/2008 | Silverbrook et al. |
| 7,361,466 B2 | 4/2008 | Korlach et al. |
| 7,384,773 B1 | 6/2008 | Benson et al. |
| 7,406,222 B2 | 7/2008 | Kornilovich |
| 7,416,844 B2 | 8/2008 | Korlach et al. |
| 7,470,549 B2 | 12/2008 | Yamamoto et al. |
| 7,473,361 B2 | 1/2009 | Craighead et al. |
| 7,485,424 B2 | 2/2009 | Korlach et al. |
| 7,518,764 B2 | 4/2009 | Osborne et al. |
| 7,545,494 B2 | 6/2009 | Haiml et al. |
| 7,545,501 B2 | 6/2009 | Muraishi et al. |
| 7,563,624 B2 | 7/2009 | Ezoe et al. |
| 7,709,808 B2 | 5/2010 | Reel et al. |
| 7,833,398 B2 | 11/2010 | Craighead et al. |
| 7,943,305 B2 | 5/2011 | Korlach et al. |
| 7,943,307 B2 | 5/2011 | Korlach et al. |
| 8,039,270 B2 | 10/2011 | Dultz et al. |
| 8,062,900 B2 | 11/2011 | Modavis |
| 8,139,288 B2 | 3/2012 | Osborne et al. |
| 8,355,133 B2 | 1/2013 | Dultz et al. |
| 8,497,073 B2 | 7/2013 | Salafsky |
| 8,932,822 B1 | 1/2015 | Salafsky |
| 2002/0037529 A1 | 3/2002 | Fesik et al. |
| 2002/0094520 A1 | 7/2002 | Salafsky et al. |
| 2002/0094528 A1 | 7/2002 | Salafsky |
| 2002/0127563 A1 | 9/2002 | Salafsky |
| 2003/0129649 A1 | 7/2003 | Kobilka et al. |
| 2003/0148391 A1 | 8/2003 | Salafsky |
| 2004/0146460 A1 | 7/2004 | Salafsky |
| 2005/0118731 A1 | 6/2005 | Salafsky |
| 2006/0046134 A1 | 3/2006 | Cho et al. |
| 2006/0228725 A1 | 10/2006 | Salafsky |
| 2009/0032592 A1 | 2/2009 | Christensen |
| 2010/0068144 A1 | 3/2010 | Salafsky |
| 2010/0120164 A1 | 5/2010 | Salafsky |
| 2012/0202296 A1 | 8/2012 | Eisenthal |
| 2012/0214164 A1 | 8/2012 | Densham |
| 2013/0129628 A1 | 5/2013 | Pantazis et al. |
| 2013/0288271 A1 | 10/2013 | Salafsky |
| 2014/0178896 A1 | 6/2014 | Salafsky |
| 2014/0178897 A1 | 6/2014 | Salafsky |
| 2014/0186854 A1 | 7/2014 | Salafsky |
| 2014/0187431 A1 | 7/2014 | Salafsky |
| 2014/0187432 A1 | 7/2014 | Salafsky |
| 2014/0187433 A1 | 7/2014 | Salafsky |
| 2015/0051110 A1 | 2/2015 | Salafsky et al. |

FOREIGN PATENT DOCUMENTS

| | | |
|---|---|---|
| WO | WO 94/29351 A2 | 12/1994 |
| WO | WO 95/34683 A1 | 12/1995 |
| WO | WO 97/09446 A1 | 3/1997 |
| WO | WO 97/15390 A1 | 5/1997 |
| WO | WO 97/35196 A1 | 9/1997 |
| WO | WO 97/46251 A1 | 12/1997 |
| WO | WO 97/47314 A1 | 12/1997 |
| WO | WO 98/14277 A1 | 4/1998 |
| WO | WO 98/15833 A1 | 4/1998 |
| WO | WO 98/20036 A1 | 5/1998 |
| WO | WO 98/20159 A1 | 5/1998 |
| WO | WO 98/20169 A1 | 5/1998 |
| WO | WO 99/51642 A1 | 10/1999 |
| WO | WO 00/00823 A1 | 1/2000 |
| WO | WO 00/39585 A1 | 7/2000 |
| WO | WO 02/44412 A1 | 6/2002 |
| WO | WO 02/46764 A1 | 6/2002 |
| WO | WO 02/54071 A1 | 7/2002 |
| WO | WO 02/61415 A1 | 8/2002 |
| WO | WO 02/095070 A2 | 11/2002 |
| WO | WO 03/055379 A2 | 7/2003 |
| WO | WO 03/064991 A2 | 8/2003 |
| WO | WO 03/104851 A2 | 12/2003 |
| WO | WO 2012/129347 A1 | 9/2012 |
| WO | WO 2013/115867 A1 | 8/2013 |
| WO | WO 2013/162654 A1 | 10/2013 |
| WO | WO 2014/201435 A1 | 12/2014 |

OTHER PUBLICATIONS

U.S. Appl. No. 60/260,249, filed Jan. 8, 2001, Salafsky.
U.S. Appl. No. 60/260,261, filed Jan. 8, 2001, Salafsky.
U.S. Appl. No. 60/260,300, filed, Jan. 8, 2001, Salafsky.
U.S. Appl. No. 60,262,214, filed Jan. 17, 2001, Salafsky.
U.S. Appl. No. 60/265,775, Feb. 1, 2001, Salafsky.
U.S. Appl. No. 60/278,941, filed Mar. 27, 2001, Salafsky.
U.S. Appl. No. 60/306,040, filed Jul. 17, 2001, Salafsky.
U.S. Appl. No. 60/347,821, filed Oct. 23, 2001, Salafsky.
U.S. Appl. No. 60/350,322, filed Jan. 17, 2002, Salafsky.

(56) References Cited

OTHER PUBLICATIONS

Abbyad, et al. Measurement of solvation responses at multiple sites in a globular protein. J Phys Chem B. Jul. 19, 2007;111(28):8269-76. Epub Jun. 26, 2007.
Abel, et al. Fiber-optic evanescent wave biosensor for the detection of oligonucleotides . . . Anal. Chem. 1996; 68:2905-2912.
Abrams, et al. Mutant ras epitopes as targets for cancer vaccines. Semin Oncol. Feb. 1996;23(1):118-34.
Achari, et al. 1.67-A X-ray structure of the B2 immunoglobulin-binding domain of streptococcal protein G and comparison to the NMR structure of the B1 domain. Biochemistry. Nov. 3, 1992;31(43):10449-57.
Aggarwal, et al. Contribution of the S4 segment to gating charge in the Shaker K+ channel. Neuron. Jun. 1996;16(6):1169-77.
Agrawal, et al. Site-specific functionalization of oligodeoxynucleotides for nonradioactive labelling. Tetrahedron Letters. 1990 31:1543-1546.
Annis, et al. A general technique to rank protein-ligand binding affinities and determine allosteric versus direct binding site competition in compound mixtures. J Am Chem Soc. Dec. 1, 2004;126(47):15495-503.
Antikainen, et al. Conformation coupled enzyme catalysis: single-molecule and transient kinetics investigation of dihydrofolate reductase. Biochemistry. Dec. 27, 2005;44(51):16835-43.
Antony, et al. A molecular beacon strategy for the thermodynamic characterization of triplex DNA: triplex formation at the promoter region of cyclin D1. Biochemistry. Aug. 7, 2001;40(31):9387-95.
Aplin, et al. Protein-derivatised glass coverslips for the study of cell-to substratum adhesion. Anal Biochem. May 1, 1981;113(1):144-8.
Arnold, et al. Identification of bone morphogenetic proteins and their receptors in human breast cancer cell lines: importance of BMP2. Cytokine. Dec. 1999;11(12):1031-7.
Arnold. Metal-affinity separations: a new dimension in protein processing. Biotechnology (N Y). Feb. 1991;9(2):151-156.
Austermuhle, et al. Maltose-binding protein is open in the catalytic transition state for ATP hydrolysis during maltose transport. J Biol Chem. Jul. 2, 2004;279(27):28243-50. Epub Apr. 26, 2004.
Bakhtiar. Peptide nucleic acids: deoxyribonucleic acid mimics with a peptide backbone. Biochem. Educ. 1998; 26:277-280.
Barlow, et al. Studies of the electronic structure of metallocene-based second-order nonlinear optical dyes. J. Am. Chem. Soc. 1999; 121:3715-3723.
Bar-Sagi. A Ras by any other name. Mol Cell Biol. Mar. 2001;21(5):1441-3.
Ben-Oren, et al. Infrared nonlinear optical measurements of membrane potential in photoreceptor cells. Biophys J. Sep. 1996;71(3):1616-20.
Bentin, et al. Triplexes involving PNA. Triple Helix Form. Oligonucleotides. 1999; 245-255.
Berkovic, et al. Interference between second-harmonic generation from a substrate and from an adsorbate layer. Journal of the Optical Society of America B-Optical Physics. 1989; 6:205-208.
Bertoncini, et al. Release of long-range tertiary interactions potentiates aggregation of natively unstructured alpha-synuclein. Proc Natl Acad Sci U S A. Feb. 1, 2005;102(5):1430-5. Epub Jan. 25, 2005.
Bethea. Experimental technique of dc induced SHG in liquids: measurement of the nonlinearity of CH2I2. Applied Optics. 1975; 14:1447-1451.
Bier, et al. Real-time measurement of nucleic-acid hybridization using evanescent-wave sensors: steps towards the genosensor. Sens. Actuators B Chem. 1997; 38:78-82.
Bieri, et al. Micropatterned immobilization of a G protein-coupled receptor and direct detection of G protein activation. Nature Biotechnology. 1999; 17:1105-1108.
Blanchard, et al. High-density oglionucleotide arrays. Biosensors and Bioelectronics. 1996; 11:687-690.

Bonnet, et al. Kinetics of conformational fluctuations in DNA hairpin-loops. Proc Natl Acad Sci U S A. Jul. 21, 1998;95(15):8602-6.
Bonnet, et al. Thermodynamic basis of the enhanced specificity of structured DNA probes. Proc Natl Acad Sci U S A. May 25, 1999;96(11):6171-6.
Bouevitch, et al. Probing membrane potential with nonlinear optics. Biophys J. Aug. 1993;65(2):672-9.
Boyd, et al. Local-field enhancement on rough surfaces with the use of optical 2nd-harmonic generation. Phys. Rev. B 1984; 30:519-526.
Brian, et al. Allogeneic Stimulation of Cyto-toxic T-cells by Supported Planar Membranes. PNAS-Biological Sciences. 1984; 81(19): 6159-6163.
Brooks, et al. Optimizing levodopa therapy for Parkinson's disease with levodopa/carbidopa/entacapone: implications from a clinical and patient perspective. Neuropsychiatr Dis Treat. Feb. 2008;4(1):39-47.
Brown, et al. Exploring the new world of the genome with DNA microarrays. Nature Genet. 1999; 21 (Suppl.):33-37.
Brown, et al. Molecular beacons attached to glass beads fluoresce upon hybridisation to target DNA. Chemical Comm 2000; 621-622.
Buchardt, et al. Peptide nucleic acids and their potential applications in biotechnology. Tibtech. 1993; 11:384-386.
Campagnola, et al. High-resolution nonlinear optical imaging of live cells by second harmonic generation. Biophys J. Dec. 1999;77(6):3341-9.
Campagnola, et al. Second-harmonic imaging microscopy for visualizing biomolecular arrays in cells, tissues and organisms. Nat Biotechnol. Nov. 2003;21(11):1356-60.
Campagnola, et al. Three-dimensional high-resolution second-harmonic generation imaging of endogenous structural proteins in biological tissues. Biophysical Journal. 2002; 81:493-508.
Case-Green, et al. Analysing genetic information with DNA arrays. Curr Opin Chem Biol. Jun. 1998;2(3):404-10.
Cha, et al. Atomic Scale Movement of the Voltage-Sensing Region in a Potassium Channel Measureed via Spectroscopy. Nature. Dec. 16, 1999;402(6763):809-13.
Cha, et al. Characterizing voltage-dependent conformational changes in the Shaker K+ channel with fluorescence. Neuron. Nov. 1997;19(5):1127-40.
Chang, et al. Human genome contains four genes homologous to transforming genes of Harvey and Kirsten murine sarcoma viruses. Proc Natl Acad Sci U S A. Aug. 1982;79(16):4848-52.
Chen, et al. Detection of Molecular Monolayers by Optical Second-Harmonic Generation. Physical Review Letters. 1981; 46:1010-1012.
Chen, et al. Molecular beacons: a real-time polymerase chain reaction assay for detecting *Salmonella*. Anal Biochem. Apr. 10, 2000;280(1):166-72.
Cheng, et al. Experimental investigations of organic molecular nonlinear optical polarizabilities. 1. Methods and results on benzene and stilbene derivatives. J. Phys. Chem. 1991; 95:10631-10643.
Cheng, et al. Experimental investigations of organic molecular nonlinear optical polarizabilities. 2. A study of conjugation dependencies. J. Phys. Chem. 1991; 95:10643-10652.
Cheung, et al. Making and reading microarrays. Nature Genetics. 1999; 21:15-19.
Chrisey, et al. Covalent Attachment of Synthetic DNA to Self-Assembled Monolayer Films. Nucleic Acids Research. 1996; 24:3031-3039.
Christopoulos. Allosteric binding sites on cell-surface receptors: novel targets for drug discovery. Nat Rev Drug Discov. Mar. 2002;1(3):198-210.
Chung, et al. Two-Dimensional Standing Wave Total Internal Reflection Fluorescence Microscopy: Superresolution Imaging of Single Molecular and Biological Specimens. Biophys J. Sep. 1, 2007; 93(5): 1747-1757.
Clackson, et al. Making antibody fragments using phage display libraries. Nature. Aug. 15, 1991;352(6336):624-8.
Clarke, et al. Conformational changes of fibrinogen after adsorption. Journal of Physical Chemistry B. 2005; 109:22027-22035.

(56) References Cited

OTHER PUBLICATIONS

Clays, et al. Nonlinear optical properties of proteins measured by hyper-rayleigh scattering in solution. Science. Nov. 26, 1993;262(5138):1419-22.
Clayton, et al. K-ras point mutation detection in lung cancer: comparison of two approaches to somatic mutation detection using ARMS allele-specific amplification. Clin Chem. Dec. 2000;46(12):1929-38.
Cohen, et al. A Fluorescent Probe Designed for Studying Protein Conformational Change. PNAS. 2005; 102(4):965-970.
Cohen, et al. Probing protein electrostatics with a synthetic fluorescent amino acid. Science. 2002; 296:1700-1703.
Conboy, et al. Studies of Alkane/water interfaces by total internal reflection second harmonic generation. J. Phys. Chem. 1994; 98:9688-9698.
Conway, et al. Fibrils formed in vitro from alpha-synuclein and two mutant forms linked to Parkinson's disease are typical amyloid. Biochemistry. Mar. 14, 2000;39(10):2552-63.
Corey. Peptide nucleic acids: expanding the scope of nucleic acid recognition. TIBTECH. 1997; 15:224-229.
Craighead, et al. Textured surfaces: optical storage and other applications. J. Vac. Sci. Technol. 1982; 20:316-319.
Craighead, et al. Textured thin-film Si solar selective adsorbers using reactive ion etching Appl. Phys. Lett. 1980; 37:653-655.
Cwirla, et al. Peptides on phage: a vast library of peptides for identifying ligands. Proc Natl Acad Sci U S A. Aug. 1990;87(16):6378-82.
De Baar, et al. One-tube real-time isothermal amplification assay to identify and distinguish human immunodeficiency virus type 1 subtypes A, B, and C and circulating recombinant forms Ae and Ag. Journal of Clinical Microbiology. 2001; 39(5):1895-1902.
De Baar, et al. Single rapid real-time monitored isothermal RNA amplification assay for quantification of human immunodeficiency virus type 1 isolates from groups M, N, and O. J Clin Microbiol. Apr. 2001;39(4):1378-84.
De Ronde, et al. Establishment of new transmissible and drug-sensitive human immunodeficiency virus type 1 wild types due to transmission of nucleoside analogue-resistant virus. J Virol. Jan. 2001;75(2):595-602.
Delprincipe et al. Two Photo and UV-Laser Flash Photlysis of Ca Cage Dimethoynitrophenyl-EGTA-4. Cell Calcium. 1999; 25:85-91.
Derrick, et al. Crystal structure of a streptococcal protein G domain bound to an Fab fragment. Nature. Oct. 22, 1992;359(6397):752-4.
Devor. Use of molecular beacons to verify that the serine hydroxymethyltransferase pseudogene SHMT-psl is unique to the order Primates. Genome Biol. 2001;2(2):RESEARCH0006. Epub Jan. 29, 2001.
Ditcham, et al. An immunosensor with potential for the detection of viral antigens in body fluids, based on surface second harmonic generation. Biosens Bioelectron. May 2001;16(3):221-4.
Ditlbacher, et al. Electromagnetic Interaction of Fluorophores with Designed Two-Dimensional Silver Nanoparticle Arrays. Applied Physics B .2001; 73;373-377.
Doring, et al. Enhanced internal dynamics of a membrane transport protein during substrate translocation. Protein Sci. Nov. 2000;9(11):2246-50.
Dracheva, et al. N-methyl-D-aspartic acid receptor expression in the dorsolateral prefrontal cortex of elderly patients with schizophrenia. Am J Psychiatry. Sep. 2001;158(9):1400-10.
Dubertret, et al. Single-mismatch detection using gold-quenched fluorescent oligonucleotides. Nat Biotechnol. Apr. 2001;19(4):365-70.
Dueholm, et al. Chemistry, properties, and applications of PNA (Peptide Nucleic Acid). New J. Chem.1997; 21:19-31.
Duggan, et al. Expression profiling using cDNA microarrays. Nat Genet. Jan. 1999;21(1 Suppl):10-4.
Duncan, et al. The binding site for C1q on IgG. Nature. Apr. 21, 1988;332(6166):738-40.
Durand, et al. Use of molecular beacons to detect an antifolate resistance-associated mutation in Plasmodium falciparum. Antimicrob Agents Chemother. Dec. 2000;44(12):3461-4.
Dworczak, et al. Electric field induced second harmonic generation (EFISH) experiments in the swivel cell: new aspects of an established method. Phys. Chem. Chem. Phys., 2000; 2:5057-5064.
Eckstein. Oligonucleotides and analogues. Oxford University Press. 1991.
Efimov, et al. Bacteriophage T4 as a surface display vector. Virus Genes. 1995;10(2):173-7.
Eisenthal. Photochemistry and photophysics of liquid interfaces by second harmonic spectroscopy. J. Phys. Chem. 1996; 100:12997-13006.
Ekins, et al. Microarrays: their origins and applications. Trends Biotechnol. Jun. 1999;17(6):217-8.
Eldrup, et al. Peptide nucleic acids: potential as antisense and antigene drugs. Adv. Amino Acid Mimetics Peptidomimetics. 1999; 2:221-245.
Elender, et al. Functionalisation of Si/SiO2 and glass surfaces with ultrathin dextran films and deposition of lipid bilayers. Biosens Bioelectron. 1996;11(6-7):565-77.
El-Hajj, et al. Detection of rifampin resistance in Mycobacterium tuberculosis in a single tube with molecular beacons. J Clin Microbiol. Nov. 2001;39(11):4131-7.
Emory, et al. Direct Observation of Size-Dependent Optical Enhancement in Single Metal Nanoparticles. J. Am. Chem. Soc. 1998; 120: 8009-8010.
Emory, et al. Screening and Enrichment of Metal Nanoparticles with Novel Optical Properties. J. Phys. Chem. B. 1998; 102:493-497.
England. Unnatural amino acid mutagenesis: A precise tool for probing protein structure and function. Biochemistry. 2004; 43(37):11623-11629.
Eun, et al. Molecular beacons: a new approach to plant virus detection. Phytopathology. Mar. 2000;90(3):269-75. doi: 10.1094/PHYTO.2000.90.3.269.
European search report Jan. 24, 2008 for EP Application No. 03736879.2.
European search report May 18, 2005 for EP Application No. 01995403.1.
European search report Dec. 3, 2004 for EP Application No. 01957166.0.
Falkiewicz. Peptide nucleic acids and their structural modifications. Acta Biochim Pol. 1999;46(3):509-29.
Fang, et al. Using molecular beacons to probe molecular interactions between lactate dehydrogenase and single-stranded DNA. Anal Chem. Jul. 15, 2000;72(14):3280-5.
Fejer, et al. Quasi-Phase-Matched Second Harmonic Generation Tuning and Tolerances. IEEE Journal of Quantum Electronics. 1992; 28(11):2631-2654.
Felderhof, et al. Optical second-harmonic generation from adsorbate layers in total-reflection geometry. Journal of the Optical Society of America B-Optical Physics. 1993; 10:1824-1833.
Feller, et al. Investigation of surface-induced alignment liquid-crystal molecules by optical second-harmonic generation. Physical Review A. 1991; 43(12), 6778-6792.
Ferguson, et al. A fiber-optic DNA biosensor microarray for the analysis of gene expression. Nat Biotechnol. Dec. 1996;14(13):1681-4.
Fernandez, et al. NMR of alpha-synuclein-polyamine complexes elucidates the mechanism and kinetics of induced aggregation. EMBO J. May 19, 2004;23(10):2039-46. Epub Apr. 22, 2004.
Finn, et al. Measurements of hyperpolarizabilities for some halogenated methanes. J. Chem. Phys. 1974; 60:454-458.
Fittinghoff. Collinear type II second-harmonic-generation frequency-resolved optical gating for use with high-numerical-aperature objectives, 1998, Opt Lett, 23(13), 1046-1048.
Fodor, et al. Light-directed Spatially-addressable Parallel Chemical Synthesis. Science. 1991; 251:767-773.
Fodor. Massively parallel genomics. Science. 1997; 277:393-395.
Fortin, et al. Use of real-time polymerase chain reaction and molecular beacons for the detection of *Escherichia coli* O157:H7. Anal Biochem. Feb. 15, 2001: 289(2):281-8.

(56) References Cited

OTHER PUBLICATIONS

Frey, et al. Two-dimensional protein crystallization via metal-ion coordination by naturally occurring surface histidines. Proc Natl Acad Sci U S A. May 14, 1996;93(10):4937-41.
Friday, et al. K-ras as a target for cancer therapy. Biochim Biophys Acta. Nov. 25, 2005;1756(2):127-44. Epub Aug. 18, 2005.
Fulton, et al. Advanced multiplexed analysis with the FlowMetrix system. Clin Chem. Sep. 1997;43(9):1749-56.
Galletto, et al. Enhancement of second harmonic response by adsorbates on gold colloids: the effect of aggregation. J. Phys. Chem. B. 1999; 103:8706-8710.
Gao, et al. Messenger RNA release from ribosomes during 51-translational blockage by consecutive low-usage arginine but not leucine codons in *Escherichia coli*. Mol Microbiol. Aug. 1997;25(4):707-16.
Garcia-Pomar, et al. Experimental two-dimensional field mapping of total internal reflection lateral beam shift in a self-collimated photonic crystal. Appl. Phys. Lett. 94, 061121 (2009) http://dx.doi.org/10.1063/1.3085768.
Georger, et al. Coplanar Patterns of Self-assembled Monolayers for Selective Cell-adhesion and Outgrowth Thin Solid Films. 1992; 210(1-2): 716-719.
Gether, et al. Fluorescent labeling of purified beta 2 adrenergic receptor. Evidence for ligand-specific conformational changes. Biol Chem. Nov. 24, 1995;270(47):28268-75.
Geysen, et al. Small peptides induce antibodies with a sequence and structural requirement for binding antigen comparable to antibodies raised against the native protein. Proc Natl Acad Sci U S A. Jan. 1985;82(1):178-82.
Geysen, et al. Strategies for epitope analysis using peptide synthesis J Immunol Methods. Sep. 24, 1987;102(2):259-74.
Geysen, et al. The delineation of peptides able to mimic assembled epitopes. Ciba Found Symp. 1986;119:130-49.
Geysen, et al. Use of peptide synthesis to probe viral antigens for epitopes to a resolution of a single amino acid. Proc Natl Acad Sci U S A. Jul. 1984;81(13):3998-4002.
Ghanouni, et al. Agonist-induced conformational changes in the G-protein-coupling domain of the beta 2 adrenergic receptor. Proc Natl Acad Sci U S A. May 22, 2001;98(11):5997-6002. Epub May 15, 2001.
Ghanouni, et al. Functionally Different Agonists Induce Distinct Conformations in the G Protein Coupling Domain of the B2 Adrenergic Receptor. Journal of Biological Chemistry. 2001; 276:24433-24436.
Giesendorf, et al. Molecular beacons: a new approach for semiautomated mutation analysis. Clin Chem. Mar. 1998;44(3):482-6.
Giusti, et al. Synthesis and characterization of 51-fluorescent-dye-labeled oligonucleotides. PCR Methods Appl. Feb. 1993;2(3):223-7.
Glauner, et al. Spectroscopic Mapping of Voltage Sensor Movement in the *Shaker* Potassium Channel. Nature. 1999; 402:813-817.
Gliko, et al. Fast two-dimensional standing-wave total-internal-reflection fluorescence microscopy using acousto-optic deflectors. Optics Letters. 2009; 34(6):836-838.
Goddard, et al. Sequence dependent rigidity of single stranded DNA. Phys Rev Lett. Sep. 11, 2000;85(11):2400-3.
Goh, et al. Absolute Orientation of Water-Molecules at the Neat Water-Surface. Journal of Physical Chemistry. 1988; 92:5074-5075.
Gold, et al. The Mycobacterium tuberculosis IdeR is a dual functional regulator that controls transcription of genes involved in iron acquisition, iron storage and survival in macrophages. Mol Microbiol. Nov. 2001;42(3):851-65.
Gonzalez, et al. Race-specific HIV-1 disease-modifying effects associated with CCR5 haplotypes. Proc Natl Acad Sci U S A. Oct. 12, 1999;96(21):12004-9.
Goodey, et al. Allosteric regulation and catalysis emerge via a common route. Nat Chem Biol. Aug. 2008;4(8):474-82. doi: 10.1038/nchembio.98.

Gotink, et al. Anti-angiogenic tyrosine kinase inhibitors: what is their mechanism of action? Angiogenesis. Mar. 2010;13(1):1-14. doi: 10.1007/s10456-009-9160-6. Epub Dec. 11, 2009.
Grant, et al. Novel allosteric sites on Ras for lead generation. PLoS One. 2011;6(10):e25711. doi: 10.1371/journal.pone.0025711. Epub Oct. 25, 2011.
Greijer, et al. Multiplex real-time NASBA for monitoring expression dynamics of human cytomegalovirus encoded IE1 and pp. 67 RNA. J Clin Virol. Feb. 2002;24(1-2):57-66.
Gronenborn, et al. A novel, highly stable fold of the immunoglobulin binding domain of streptococcal protein G. Science. Aug. 9, 1991;253(5020):657-61.
Groves, et al. Electrical manipulation of glycan-phosphatidyl inositol-tethered proteins in planar supported bilayers. Biophys J. Nov. 1996;71(5):2716-23.
Groves, et al. Micropattern formation in supported lipid membranes. Acc Chem Res. Mar. 2002;35(3):149-57.
Groves, et al. Micropatterning fluid bilayers on solid supports. Science. 1997; 275:651-653.
Gunner, et al. Electrostatic Potentials in Rhodopseudomonas Viridis Reaction Centers: Implications for the Driving Force and Directionality of Electron Transfer. J. Phys. Chem. 1996; 100:4277-4291.
Gupta, et al. A general method for the synthesis of 3'-sulfhydryl and phosphate group containing oligonucleotides. Nucleic Acids Res. Jun. 11, 1991;19(11):3019-25.
Hall, et al. Syntheses and Photophysical Properties of Some 5(2)-Aryl-2(5)-(4-pyridy0oxazoles and Related Oxadiazoles and Furans. J. Heterocyclic Chem. 1992; 29,:1245-1273.
Hall, et al. The structural basis for the transition from Ras-GTP to Ras-GDP. Proc Natl Acad Sci U S A. Sep. 17, 2002;99(19):12138-42. Epub Sep. 4, 2002.
Harrick. Internal reflection spectroscopy. Hulick Scientific Corporation. 2nd printing 1979.
Harrison. Variation on an SRC-like Theme. Cell. 2003; 112(6):737-740.
Heath, et al. Covalent attachment of immunoglobulins to liposomes via glycosphingolipids. Biochim Biophys Acta. Jan. 8, 1981;640(1):66-81.
Heil, et al. Betaine-homocysteine methyltransferase (BHMT): genomic sequencing and relevance to hyperhomocysteinemia and vascular disease in humans. Mol Genet Metab. Nov. 2000;71(3):511-9.
Heinz, et al. Spectroscopy of Molecular Monolayers by Resonant Second-Harmonic Generation. Phys. Rev. Lett. 1982; 48, 478. DOI: http://dx.doi.org/10.1103/PhysRevLett.48.478.
Heinz. Determination of molecular orientation of monlayer adsorbates by optical second-harmonic generation. Physical Review A. 1991; 28(3):1883-1885.
Helmreich, et al. Structure and function of proteins in G-protein-coupled signal transfer. Biochim Biophys Acta. Oct. 29, 1996;1286(3):285-322.
Helps, et al. Use of real-time quantitative PCR to detect Chlamydophila felis infection. J Clin Microbiol. Jul. 2001;39(7):2675-6.
Hicks. Studies of Chemical Processes in Liquids Using Short Laser Pulses: 1. The Dynamics of Photoisomerization of Polar Molecules in Solution 2. Studies of Liquid Surfaces by Second Harmonic Generation Ph.D. dissertation, Columbia University. 1986.
Ho, et al. Optical sensors based on hybrid aptamer/conjugated polymer complexes. J Am Chem Soc. Feb. 11, 2004;126(5):1384-7.
Ho, et al. Optical sensors based on hybrid DNA/conjugated polymer complexes. Chemistry. Mar. 4, 2005;11(6):1718-24.
Hodgson, et al. The synthesis of peptides and proteins containing non-natural amino acids. Chem Soc Rev. Sep. 10, 2004;33(7):422-30. Epub Aug. 13, 2004.
Hoffmann, et al. Low scale multiple array synthesis and DNA hybridization of peptide nucleic acids. Pept. Proc. Am. Pept. Symp. 15th. 1999; 233-234.
Hoheisel. Improved solid supports and spacer/linker systems for the synthesis of spatially addressable PNAlibraries. Nucleosides Nucleotides. 1999; 18:1289-1291.

(56) References Cited

OTHER PUBLICATIONS

Huang, et al. Nonlinear optical properties of potential sensitive styryl dyes. Biophys J. May 1988;53(5):665-70.
Hubbard, et al. Nonlinear optical studies of a fluorinated poled polyimide guest-host system. Applied Physics Letters. 1994; 65(3):265-267.
Hubbard. Autoregulatory mechanisms in protein-tyrosine kinases. Journal of Biological Chemistry. 1988; 273(20):11987-11990.
Huse, et al. The conformational plasticity of protein kinases. Cell. 2002; 109:275-282.
Hyrup, et al. Peptide Nucleic Acids (PNA): Synthesis, Properties and Potential Applications. Bioorg. Med. 1996; 4:5-23.
Hyun, et al. Oriented insertion of phi29 N-hexahistidine-tagged gp10 connector protein assemblies into C20BAS bolalipid membrane vesicles. J Am Chem Soc. Dec. 8, 2010;132(48):17053-5. doi: 10.1021/ja104204z. Epub Aug. 17, 2010.
International preliminary report on patentability dated Oct. 3, 2013 for PCT/US2012/030010.
International search report and written opinion dated Apr. 20, 2012 for PCT/US2012/030010.
International search report dated Jan. 22, 2002 for PCT/US2001/022411.
International search report dated Feb. 10, 2006 for PCT Application No. PCT/US2003/017807.
International search report dated Feb. 10, 2006 for PCT/US2003/017807.
International search report dated Mar. 23, 2006 for PCT/US2002/022681.
International search report dated May 1, 2002 for PCT/US2001/046932.
International search report dated Oct. 20, 2001 for PCT/US2001/022412.
International search report dated Dec. 27, 2001 for PCT/US2001/022441.
Ishima, et al. Protein dynamics from NMR. Nature Structural Biology. 2000;7:740-743.
Jager, et al. Comparison of quasi-phase-matching geometries for second harmonic generation in poled polymer channel waveguides at 1.5 mm,. Appl. Phys. Lett.1996; 68:1183-1185.
Jiang, et al. Display of a PorA peptide from Neisseria meningitidis on the bacteriophage T4 capsid surface. Infect Immun. Nov. 1997;65(11):4770-7.
Jordens, et al. Amplification with molecular beacon primers and reverse line blotting for the detection and typing of human papillomaviruses. J Virol Methods. Sep. 2000;89(1-2):29-37.
Joshi, et al. A three-component Mannich-type reaction for selective tyrosine bioconjugation. J Am Chem Soc. Dec. 15, 2004;126(49):15942-3.
Joshi, et al. Metal-containing DNA hairpins as hybridization probes. Chem. Commun., 2001, 549-550.
Kaboev, et al. PCR hot start using primers with the structure of molecular beacons (hairpin-like structure). Nucleic Acids Res. Nov. 1, 2000;28(21):E94.
Kajikawa, et al. Second harmonic generation in disperse-red-labeled poly(methyl methacrylate) Langmuir Blodgett film. Appl. Phys. Letters. May 3, 1993; 62(18):2161-2163.
Kamat, et al. Picosecond Dynamics of Silver Nanoclusters. Photoejection of Electrons and Fragmentation. J. Phys. Chem. B. 1998; 102:3123-3128.
Kang, et al. Linkage of recognition and replication functions by assembling combinatorial antibody Fab libraries along phage surfaces. Proc Natl Acad Sci U S A. May 15, 1991;88(10):4363-6.
Kang, et al. Specific adsorption of histidine-tagged proteins on silica surfaces modified with Ni2+ /NTA-derivatized poly(ethylene glycol). Langmuir. May 22, 2007;23(11):6281-8. Epub Apr. 20, 2007.
Karpinar, et al. Pre-fibrillar alpha-synuclein variants with impaired beta-structure increase neurotoxicity in Parkinson's disease models. Embo J. Oct. 21, 2009;28(20):3256-68. doi: 10.1038/emboj.2009. 257. Epub Sep. 10, 2009.

Kemnitz, et al. The Phase of 2nd-Harmonic Light Generated at an Interface and Its Relation to Absolute Molecular-Orientation. Chemical Physics Letters. 1986; 131:285-290.
Keseru, et al. Hit discovery and hit-to-lead approaches. Drug Discov Today. Aug. 2006;11(15-16):741-8.
Khatchatouriants, et al. GFP is a selective non-linear optical sensor of electrophysiological processes in Caenorhabditis elegans. Biophys J. Nov. 2000;79(5):2345-52.
Kleinfield, et al. Controlled outgrowth of dissociated neurons on patterned substrates. J Neurosci. Nov. 1988;8(11):4098-120.
Kleinjung, et al. Fibre-optic genosensor for specific determination of femtomolar DNA oligomers. Analytica Chimica Acta. 1997; 350:51-58.
Klerks, et al. Development of a multiplex AmpliDet RNA for the simultaneous detection of Potato leafroll virus and Potato virus Y in potato tubers. J Virol Methods. Apr. 2001;93(1-2):115-25.
Klockgether. Parkinson's disease: clinical aspects. Cell Tissue Res. Oct. 2004;318(1):115-20. Epub Sep. 8, 2004.
Knighton, et al. Crystal structure of the catalytic subunit of cyclic adenosine monophosphate-dependent protein kinase. Science. Jul. 26, 1991;253(5018):407-14.
Knudsen, et al. Application of Peptide Nucleic Acid in Cancer Therapy. Anti-Cancer Drug. 1997; 8:113-118.
Kostrikis, et al. Spectral genotyping of human alleles. Science. Feb. 20, 1998;279(5354):1228-9.
Kota, et al. Detection of transgenes in crop plants using molecular beacon assays. Plant Mol Biology Rep. 1999; 17:363-370.
Kozarac, et al. Interaction of Proteins with Lipid Monolayers at the Air-Solution Interface Studied by Reflection Spectroscopy. Eur. Biophys. J. 1987; 15:193-196.
Kriech, et al. Using the intrinsic chirality of a molecule as a label-free probe to detect molecular adsorption to a surface by second harmonic generation. Applied Spectroscopy. 2005; 59:46-753.
Kufareva, et al. Type-II kinase inhibitor docking, screening, and profiling using modified structures of active kinase states. J Med Chem. Dec. 25, 2008;51(24):7921-32. doi: 10.1021/jm8010299.
Kuhner, et al. Lipid mono- and bilayer supported on polymer films: composite polymer-lipid films on solid substrates. Biophys J. Jul. 1994;67(1):217-26.
Lamprecht, et al. Femtosecond decay-time measurement of electron-plasma oscillation in nanolithographically designed silver particles. Appl. Phys. B. 1997; 64:269-272.
Lanciotti, et al. Nucleic acid sequence-based amplification assays for rapid detection of West Nile and St. Louis encephalitis viruses. J Clin Microbiol. Dec. 2001;39(12):4506-13.
Landry, et al. Pulse simulations of a mirrored counterpropagating-QPM device. Optics Express. 1999; 5(8):176-187.
Lang, et al. Parkinson's disease. Second of two parts. N. Engl J Med. Oct. 15, 1998;339(16):1130-43.
Larsson, et al. Transmembrane movement of the shaker K+ channel S4. Neuron. Feb. 1996;16(2):387-97.
Lazurkin. Stability and specificity of triplexes formed by peptide nucleic acid with DNA. Molecular Biology. 1999; 33(1):79-83.
Le Floch, et al. Label-free electrochemical detection of protein based on a ferrocenebearing cationic polythiophene and aptamer. Analytical Chemistry 78, 4727-4731 (2006).
Leone, et al. Molecular beacon probes combined with amplification by NASBA enable homogeneous, real-time detection of RNA. Nucleic Acids Res. May 1, 1998;26(9):2150-5.
Levene, et al. Zero-Mode Waveguides for Single-Molecule Analysis at High Concentrations. Science. 2003; 299 (5607): 682-686.
Levicky, et al. Using Self-Assembly to Control the Structure of DNA Monolayers on Gold: a Neutron Reflectivity Study. Journal of the American Chemical Society. 1998; 120:9787-9792.
Levine, et al. Absolute signs of hyperpolarizabilities in the liquid state. J. Chem. Phys. 1974; 60(10)3856-3858.
Levine, et al. Charge transfer complexes and hyperpolarizabilities. J. Chem. Phys. 1977; 66:1070-1074.
Levine, et al. Molecular hyperpolarizabilities determined from conjugated and nonconjugated organic liquids. Appl. Phys. Left. 1974; 24:445-447.

(56) References Cited

OTHER PUBLICATIONS

Levine, et al. Second and third order hyperpolarizabilities of organic molecules. J. Chem. Phys. 1975; 63(6):2666-2682.

Levine, et al. Second Order Hyperpolarizability of a Polypeptide a-helix: Poly—ybenzyl-L-glutamate. J. Chem. Phys. 1976; 65(5):1989-1993.

Levine, et al. Ultraviolet dispersion of the donor-acceptor charge transfer contribution to the second order hyperpolarizability. J. Chem. Phys. 1978; 69(12): 5240-5245.

Levine. Conjugated electron contributions to the second order hyperpolarizability of substituted benzene molecules J. Chem. Phys. 1975; 63:115-117.

Lewin, et al. Use of real-time PCR and molecular beacons to detect virus replication in human immunodeficiency virus type 1-infected individuals on prolonged effective antiretroviral therapy. Virol. Jul. 1999;73(7):6099-103.

Lewis, et al. Second Harmonic Generation of Biological Interfaces: Probing the Membrane Protein Bacteriorhodopsin and Imaging Membrane Potential Around GFP Molecules at Specific Sites in Neuronal Cells of C. elegans. Chemical Physics. 1999; 245:133-144.

Li, et al. Filamentous bacteriophage display of a bifunctional protein A:: scFv fusion. Mol Biotechnol. Jun. 1998;9(3):187-93.

Li, et al. Molecular beacon-based homogeneous fluorescence PCR assay for the diagnosis of infectious diseases. Analytical Sciences. 2000; 16:245-248.

Li, et al. Molecular Beacons: A Novel Approach to Detect Protein—DNA Interactions. Angew Chem Int Ed Engl. Mar. 2000;39(6):1049-1052.

Li, et al. Using molecular beacons as a sensitive fluorescence assay for enzymatic cleavage of single-stranded DNA. Nucleic Acids Res. Jun. 1, 2000;28(11):E52.

Lindquist, et al. Characterization of the interaction between alphaCP(2) and the 3'-untranslated region of collagen alphal (I) mRNA. Nucleic Acids Res. Nov. 1, 2000;28(21):4306-16.

Liu, et al. A fiber-optic evanescent wave DNA biosensor based on novel molecular beacons. Anal Chem. Nov. 15, 1999;71(22):5054-9.

Liu, et al. Molecular beacons for DNA biosensors with micrometer to submicrometer dimensions. Anal Biochem. Jul. 15, 2000;283(1):56-63.

Liu, et al. Rational design of inhibitors that bind to inactive kinase conformations. Nat Chem Biol. Jul. 2006;2(7):358-64.

Liu, et al. Real-time monitoring in vitro transcription using molecular beacons. Anal Biochem. Jan. 1, 2002;300(1):40-5.

Liu, et al. Site-directed fluorescence labeling of P-glycoprotein on cysteine residues in the nucleotide binding domains. Biochemistry. Sep. 10, 1996;35(36):11865-73.

Lopez, et al. Convenient Methods for Patterning the Adhesion of Mammalian Cells to Surfaces Using Self-Assembled Monolayers of Alkanethiolates on Gold. J. Am. Chem. Soc. 1993; 115:5877-5878.

Lorber, et al. Flexible ligand docking using conformational ensembles. Protein Sci. Apr. 1998;7(4):938-50.

Lowman, et al. Selecting high-affinity binding proteins by monovalent phage display. Biochemistry. Nov. 12, 1991;30(45):10832-8.

Lu, et al. Mutation-selective tumor remission with Ras-targeted, whole yeast-based immunotherapy. Cancer Res. Aug. 1, 2004;64(15):5084-8.

Macbeath, et al. Printing Proteins as Microarrays for High-Throughput Function Determination. Science. 2000; 289:1760-1763.

Magnuson, et al. The Raf-1 serine/threonine protein kinase.Semin Cancer Biol. Aug. 1994;5(4):247-53.

Majumdar, et al. Single-molecule Fret reveals sugar-induced conformational dynamics in LacY. Proc Natl Acad Sci U S A. Jul. 31, 2007;104(31):12640-5. Epub May 14, 2007.

Mallik, et al. Towards materials for the specific recognition and separation of proteins. New J. Chem. 1994; 18:299-304.

Manganelli, et al. Differential expression of 10 sigma factor genes in Mycobacterium tuberculosis. Mol Microbiol. Jan. 1999;31(2):715-24.

Mannuzzu, et al. Direct physical measure of conformational rearrangement underlying potassium channel gating. Science. Jan. 12, 1996;271(5246):213-6.

Marks, et al. By-passing immunization. Human antibodies from V-gene libraries displayed on phage. J Mol Biol. Dec. 5, 1991;222(3):581-97.

Marras, et al. Multiplex detection of single-nucleotide variations using molecular beacons. Genet Anal. Feb. 1999;14(5-6):151-6.

Marshall, et al. DNA chips: an array of possibilities. Nat Biotechnol. Jan. 1998;16(1):27-31.

Martin, et al. Immunospecific targeting of liposomes to cells: a novel and efficient method for covalent attachment of Fab' fragments via disulfide bonds. Biochemistry. Jul. 7, 1981;20(14):4229-38.

Martin, et al. Irreversible coupling of immunoglobulin fragments to preformed vesicles. An improved method for liposome targeting. J Biol Chem. Jan. 10, 1982;257(1):286-8.

Martinson, et al. Global distribution of the CCR2-64I/CCR5-59653T HIV-1 disease-protective haplotype. AIDS. Mar. 31, 2000;14(5):483-9.

Matsuo. In situ visualization of messenger RNA for basic fibroblast growth factor in living cells. Biochim Biophys Acta. Feb. 2, 1998;1379(2):178-84.

Matysiak, et al. Improved solid supports and spacer/linker systems for the synthesis of spatially addressable PNA-libraries. Nucleosides Nucleotides. 1999; 18:1289-1291.

McAllister, et al. DNA microarrays and genomic mismatch scanning: new genetic tools. Am. J. Hum. Genet. 1997; 61(4):1387.

McClendon, et al. Charge neutralization and collapse of the C-terminal tail of alpha-synuclein at low pH. Protein Sci. Jul. 2009;18(7):1531-40. doi: 10.1002/pro.149.

McConnell, et al. Electronic and optical properties of chemically modified metal nanoparticles and molecularly bridged nanoparticle arrays. J. Phys. Chem. B. 2000; 104: 8925-8930.

McGuinness, et al. Direct, Real-time Detection of Protein Conformation: Revealing Therapeutic Opportunities Using Second Harmonic Generation (SHG) Detection. Biodesy, LLC. Poster M143. Mar. 18-21, 2011.

McHugh, et al. Construction, purification, and functional incorporation on tumor cells of glycolipid-anchored human B7-1 (CD80). Proc Natl Acad Sci U S A. Aug. 15, 1995;92(17):8059-63.

McKillip, et al. Molecular beacon polymerase chain reaction detection of Escherichia coli 0157:H7 in milk. J Food Prot. Jul. 2000;63(7):855-9.

Mesmaeker, et al. Backbone modifications in oligonucleotides and peptide nucleic acid systems. Curr. Opin. Struct. Biol. 1995; 5:343-355.

Metzner, et al. Effects of in vivo CD8(+) T cell depletion on virus replication in rhesus macaques immunized with a live, attenuated simian immunodeficiency virus vaccine. J Exp Med. Jun. 5, 2000;191(11):1921-31.

Michael, et al. Randomly ordered addressable high-density optical sensor arrays. Anal Chem. Apr. 1, 1998;70(7):1242-8.

Millard, et al. Second harmonic imaging microscopy. Methods Enzymol. 2003;361:47-69.

Milosevic, et al. Extreme-ultraviolet harmonic generation near 13 nm with a two-color elliptically polarized laser field, 2000, Opt Lett, 25(20), 1532-1534.

Moreaux, et al. Membrane imaging by second harmonic generation microscopy. Journal of Optical Society of America B: Optical Physics. 2000; 17(10):1685-1694.

Mrksich, et al. Using self-assembled monolayers to understand the interactions of man-made surfaces with proteins and cells. Annu Rev Biophys Biomol Struct. 1996;25:55-78.

Mullah, et al. Efficient automated synthesis of molecular beacons. Nucleos Nucleot. 1999; 18:1311-1312.

Nagar, et al. Crystal structures of the kinase domain of c-Abl in complex with the small molecule inhibitors PD173955 and imatinib (STI-571). Cancer Research. 2002; 62:4236-4243.

Nagar, et al. Structural basis for the autoinhibition of c-Abl tyrosine kinase. Cell. Mar. 21, 2003;112(6):859-71.

(56) References Cited

OTHER PUBLICATIONS

Nazarenko, et al. A closed tube format for amplification and detection of DNA based on energy transfer. Nucleic Acids Res. Jun. 15, 1997;25(12):2516-21.
Needels, et al. Generation and screening of an oligonucleotide-encoded synthetic peptide library. Proc Natl Acad Sci U S A. Nov. 15, 1993;90(22):10700-4.
Nelson, et al. Bifunctional oligonucleotide probes synthesized using a novel CPG support are able to detect single base pair mutations. Nucleic Acids Res. Sep. 25, 1989;17(18):7187-94.
Neumann, et al. Functional immobilization of a ligand-activated G-protein-coupled receptor. Chembiochem. Oct. 4, 2002;3(10):993-8.
Nie, et al. Probing single molecules and single nanoparticles by surface-enhanced raman scattering. Science. 1997; 75:1102-1106.
Nielsen, et al. Peptide nucleic acid (PNA), a new molecular tool. In Molecular Biology: Current Innovations and Future Trends, Part2. Horizon Scientific Press. 1995; 73-89.
Nielsen, et al. Peptide nucleic acid (PNA). A DNA mimic with a pseudopeptide backbone. Chem. Soc. Rev. 1997; 73-78.
Nielsen, et al. Peptide nucleic acids-(PNA): Oligonucleotide analogues with a polyamide backbone. Antisense Research and Applications. 1992;363-372.
Nielsen, et al. Peptide nucleic acids (PNAs): Potential Antisense and Anti-gene Agents. Anti-Cancer Drug Design. 1993; 8:53-63.
Nielsen, P. E. "DNA analogues with nonphosphodiester backbones"Annu Rev.Biophys.Biomol.Struct. 24 (1995) 167-183.
Nielsen, P. E., Egholm, M. and Buchardt, 0. "Peptide Nucleic Acid (PNA). A DNA mimic with a peptide backbone" Bioconjugate Chemistry 5 (1994) 3-7.
Nielsen. Antisense Properties of Peptide Nucleic Acid. Handbook of Experimental Pharmacology. 1998; 131:545-560.
Nielsen. Applications of peptide nucleic acids. Curr Opin Biotechnol. 1999; 10:7175.
Nielsen. Design of Sequence-Specific DNA-Binding Ligands. Chem. Eur. J. 1997; 3:505-508.
Nielsen. Peptide nucleic acid (PNA): A lead for gene therapeutic drugs. Antisense Therapeutics. 1996; 4:76-84.
Nielsen. Peptide Nucleic Acids. Science and Medicine Planning. 1998; 48-55.
Nielsen. Sequence-specific recognition of double-stranded DNA by peptide nucleic acids. Advances in DNA Sequence-Specific Agents. 1998; 3:267-278.
Nielsen. Structural and Biological Properties of Peptide Nucleic Acid (PNA). Pure & Applied Chemistry. 1998; 70:105-110.
Noble, et al. Impact on Biophysical Parameters on the Biological Assessment of Peptide Nucleic Acids, Antisense Inhibitors of Gene Expression. Drug. Develop. Res. 1995; 34:184195.
Noble, et al. Protein kinase inhibitors: insights into drug design from structure. Science. Mar. 19, 2004;303(5665):1800-5.
Norris, et al. Reversible inhibition of alpha-synuclein fibrillization by dopaminochrome-mediated conformational alterations. J Biol Chem. Jun. 3, 2005;280(22):21212-9. Epub Apr. 6, 2005.
Novak, et al. Assembly of Phenylacetylene-Bridged Silver and Gold 5 Nanoparticle Arrays. J. Am. Chem. Soc. 2000; 122:3979-3980.
Novak, et al. Nonlinear Optical Properties of Molecularly Bridged Gold Nanoparticle Arrays. J. Am. Chem. Soc. 2000; 122:12029-12030.
Nye, et al. Kinetic control of histidine-tagged protein surface density on supported lipid bilayers. Langmuir. Apr. 15, 2008;24(8):4145-9. doi: 10.1021/la703788h. Epub Feb. 28, 2008.
Office action dated Jan. 14, 2013 for U.S. Appl. No. 12/535,631.
Office action dated Feb. 7, 2002 for U.S. Appl. No. 09/731,366.
Office action dated Feb. 16, 2011 for U.S. Appl. No. 12/571,342.
Office action dated Feb. 16, 2012 for U.S. Appl. No. 12/571,342.
Office action dated Feb. 23, 2004 for U.S. Appl. No. 09/731,366.
Office action dated Mar. 24, 2008 for U.S. Appl. No. 11/327,199.
Office action dated Mar. 30, 2009 for U.S. Appl. No. 11/327,199.
Office action dated Apr. 3, 2012 for U.S. Appl. No. 12/535,631.
Office action dated Apr. 21, 2004 for U.S. Appl. No. 09/907,038.
Office action dated May 8, 2002 for U.S. Appl. No. 09/907,035.
Office action dated Jun. 18, 2007 for U.S. Appl. No. 11/327,199.
Office action dated Aug. 25, 2003 for U.S. Appl. No. 09/907,035.
Office action dated Sep. 10, 2004 for U.S. Appl. No. 09/731,366.
Office action dated Sep. 20, 2005 for U.S. Appl. No. 10/467,098.
Office action dated Oct. 2, 2012 for U.S. Appl. No. 12/571,342.
Office action dated Oct. 23, 2003 for U.S. Appl. No. 09/731,366.
Office action dated Oct. 28, 2002 for U.S. Appl. No. 09/731,366.
Office action dated Nov. 3, 2006 for U.S. Appl. No. 10/970,754.
Office action dated Nov. 20, 2002 for U.S. Appl. No. 09/907,035.
Ong, et al. Polarization of water molecules at a charged interface: second harmonic studies of the silica/water interface. Chemical Physics Letters. 1992; 191:327-335.
Oral Abstracts from the Society of Biomolecular Sciences 14th Annual Conference and Exhibition: St. Louis, Missouri Apr. 6-10, 2008. J. Biomol Screen 2008 13: 692. DOI: 10.1177/1087057108322219.
Ortiz, et al. PNA molecular beacons for rapid detection of PCR amplicons. Mol Cell Probes. Aug. 1998;12(4):219-26.
Orum, et al. Peptide Nucleic Acid. Nucleic Acid Amplification Technologies: Application to Disease Diagnostics. 1997; 29-48.
Oudar, et al. Hyperpolarizabilities of the nitroanilines and their relations to the excited state dipole moment. J. Chem. Phys. 1977; 66. 2664-2668.
Oudar, et al. Optical nonlinearities of conjugated molecules. Stilbene derivatives and highly polar aromatic compounds. J. Chem. Phys. 1977; 67(2):446-457.
Pantano, et al. Ordered nanowells arrays. Chem. Mater. 1996; 8:2832-2835.
Pargellis, et al Inhibition of p38 Map kinase by utilizing a novel allosteric binding site. Nat Struct Biol. Apr. 2002;9(4):268-72.
Park, et al. Rapid identification of Candida dubliniensis using a species-specific molecular beacon. J Clin Microbiol. Aug. 2000;38(8):2829-36.
Paszti, et al. Sum frequency generation vibrational spectroscopy studies of protein adsorption on oxide-covered Ti surfaces. Journal of Physical Chemistry B. 2004; 108:7779-7787.
Peleg, et al. Nonlinear optical measurement of membrane potential around single molecules at selected cellular sites. Proc Natl Acad Sci U S A. Jun. 8, 1999;96(12):6700-4.
Perozo, et al. rearrangements underlying K+ -channel activation gating. Science. Jul. 2, 1999;285(5424):73-8.
Piatek, et al. Genotypic analysis of Mycobacterium tuberculosis in two distinct populations using molecular beacons: implications for rapid susceptibility testing. Antimicrob Agents Chemother. Jan. 2000;44(1):103-10.
Piatek, et al. Molecular beacon sequence analysis for detecting drug resistance in Mycobacterium tuberculosis. Nat Biotechnol. Apr. 1998;16(4):359-63.
Pierce, et al. Real-time PCR using molecular beacons for accurate detection of the Y chromosome in single human blastomeres. Mol Hum Reprod. Dec. 2000;6(12):1155-64.
Pitchford, et al. Direct, real-time detection of kinae type II inhibitors using second harmonic generation (SHG) detection. 2011. Poster T380. Retrieved Apr. 18, 2012. www.labautopedia.com/mw/images/T380posterSBS2011.jpg.
Piunno, et al. Fiber-optic DNA sensor for fluorometric nucleic acid determination. Anal Chem. Aug. 1, 1995;67(15):2635-43.
Poddar. Detection of adenovirus using PCR and molecular beacon. J Virol Methods. Sep. 1999;82(1):19-26.
Poddar. Symmetric vs asymmetric PCR and molecular beacon probe in the detection of a target gene of adenovirus. Mol Cell Probes. Feb. 2000;14(1):25-32.
Polizzi, et al. (2004). Ellipsometric approach for the real-time detection of label-free protein absroption by second harmonic generation. Journal of the American Chemical Society. 2004; 126:5001-5007.
Potyrailo, et al. Adapting selected nucleic acid ligands (aptamers) to biosensors. Anal Chem. Aug. 15, 1998;70(16):3419-25.
Rajagopalan, et al. Interaction of dihydrofolate reductase with methotrexate: ensemble and single-molecule kinetics. Proc Natl Acad Sci U S A. Oct. 15, 2002;99(21):13481-6. Epub Oct. 1, 2002.

(56) References Cited

OTHER PUBLICATIONS

Ramsay. DNA chips-states-of-the-art. Nature Biotechnology. 1998; 16(1):40-44.
Reider, et al. Second-order Nonlinear Optical Effects at Surfaces and Interfaces in Photonic Probes of Surfaces. Halevia, P., editor. Elsevier Science, Amsterdam. Chapter 9. 1995. 415-478.
Ren, et al. Cloning of linear DNAs in vivo by overexpressed T4 DNA ligase: construction of a T4 phage hoc gene display vector. Gene. Aug. 22, 1997;195(2):303-11.
Ren, et al. Phage display of intact domains at high copy number: a system based on SOC, the small outer capsid protein of bacteriophage T4. Protein Sci. Sep. 1996;5(9):1833-43.
Ren, et al. Phage T4 SOC and HOC display of biologically active, full-length proteins on the viral capsid. Gene. Jul. 30, 1998;215(2):439-44.
Revision history of T380:Pitchford:SHGKinaseposter. Retrieved on Apr. 18, 2012. Retrieved from the internet: http://www.labautopedia.com/mw/index.php?title=T380:Pitchford:SHG-KinasePoster&action=history.
Rhee, et al. Molecular epidemiologic evaluation of transmissibility and virulence of *Mycobacterium tuberculosis*. J Clin Microbiol. Jun. 1999;37(6):1764-70.
Rinuy, et al. Second harmonic generation of glucose oxidase at the air/water interface. Biophysial Journal. 1999; 77:3350-3355.
Rodriguez, et al. In vivo incorporation of multiple unnatural amino acids through nonsense and frameshift suppression. Proc Natl Acad Sci U S A. Jun. 6, 2006;103(23):8650-5. Epub May 25, 2006.
Sackmann. Supported membranes: scientific and practical applications. Science. Jan. 5, 1996;271(5245):43-8.
Saha, et al. Quantitation of HIV-1 by real-time PCR with a unique fluorogenic probe. J Virol Methods. Apr. 2001;93(1-2):33-42.
Salafsky, et al. A second-harmonic-active unnatural amino acid as a structural probe of biomolecules on surfaces. J. Phys. Chem. B, 2008, 112 (47), pp. 15103-15107.
Salafsky, et al. Architecture and function of membrane proteins in planar supported bilayers: a study with photosynthetic reaction centers' Biochemistry. 1996; 35(47):14773-14781.
Salafsky, et al. Protein absorption at interfaces detected by second-harmonic generation. Journal of Physical Chemistry B. 2000; 104:7752-7755.
Salafsky, et al. Protein absorption at interfaces detected by second-harmonic generation. J. Phys. Chem. B. 2004; 108(10):3376. Additions and Corrections.
Salafsky, et al. Real-time measurement of protein conformational change in key therapeutic targets: application to Abl kinase and mutant Ras. Biodesy, LLC. SLAS2012 talk abstract. Nov. 2011.
Salafsky, et al. Second Harmonic Spectroscopy: Detection and Orientation of Molecules at a Biomembrane Interface. Chemical Physics Letters 2000; 319:435-439.
Salafsky, et al. SHG labels for detection of molecules by second harmonic generation. Chemical Physics Letters. 2001; 342:485-491.
Salafsky, J. (Apr. 2008). "Second-Harmonic Generation (SHG) for Identification of Allosteric D & Conformation-Specific Compounds" PowerPoint Presentation presented to SBS, 30 pages.
Salafsky, J. (Apr.15, 2009). "Detection Method for Conformational Change Second—Harmonic Generation Provides a Molecular-Level, Functional Readout in Real Time" Gen Eng & Biotech News, 2 pages.
Salafsky. Detection of protein conformational change by optical second-harmonic generation. J Chem Phys. Aug. 21, 2006;125(7):074701.
Salafsky. Real-time measurement of protein conformational change in key therapeutic targets: applications to Abl-kinase and mutant Ras. Biodesy, LLC. SLAS Conference. PPT presentation. Feb. 7, 2012.
Salafsky. Real-time measurement of protein conformational change in key therapeutic targets: applications to Abl-kinase and mutant Ras. Biodesy, LLC. SLAS2012 talk Summary. Feb. 7, 2012.
Salafsky. Second-harmonic generation as a probe of conformational change in molecules. Chemical Physics Letters. 2003; 381(5):705-709.
Salafsky. Second-harmonic generation for studying structural motion of biological molecules in real time and space. Phys Chem Chem Phys. Nov. 14, 2007;9(42):5704-11. Epub Sep. 7, 2007.
Samanta, et al. Excited state dipole moment of Prodan as determined from transient dieletric loss measurements. Journal of Physical Chemistry A. 2000; 104:8972-8975.
Sandberg, et al. New chemical descriptors relevant for the design of biologically active peptides. A multivariate characterization of 87 amino acids. J Med Chem. Jul. 2, 1998;41(14):2481-91.
Sauer-Eriksson, et al. Crystal structure of the C2 fragment streptococcal protein G in complex with the FC domain of the human IgG. Structure. 19951 3(3):265-278.
Schena, et al. Quantitative monitoring of gene expression patterns with a complementary DNA microarray. Science. Oct. 20, 1995;270(5235):467-70.
Schindler, et al. Structural mechanism for STI-571 inhibition of abelson tyrosine kinase. Science. Sep. 15, 2000;289(5486):1938-42.
Schneider, et al. Synthesis and characterization of the first fluorescent nonpeptide NPY Y1 receptor antagonist. Chembiochem. Nov. 5, 2007;8(16):1981-8.
Schofield, et al. Molecular beacons: trial of a fluorescence based solution hybridization technique for ecological studies with ruminal bacteria. Appl Environ Microbiol. 1997; 63(3):1143-1147.
Schoofs, et al. Epitopes of an influenza viral peptide recognized by antibody at single amino acid resolution. J Immunol Jan. 15, 1988;140(2):611-6.
Schwede, et al. Swiss-Model: an automated protein homology-modeling server. Nucleic Acids Res. Jul. 1, 2003;31(13):3381-5.
Scott, et al. Searching for peptide ligands with an epitope library. Science. Jul. 27, 1990;249(4967):386-90.
Sebti, et al. Candida dubliniensis at a cancer center. Clin Infect Dis. Apr. 1, 2001;32(7):1034-8. Epub Mar. 15, 2001.
Seeliger, et al. c-Src binds to the cancer drug imatinib with an inactive Abl/c-Kit conformation and a distributed thermodynamic penalty. Structure. Mar. 2007;15(3):299-311.
Seeliger, et al. Equally potent inhibition of c-Src and Abl by compounds that recognize inactive kinase conformations. Cancer Res. Mar. 15, 2009;69(6):2384-92. doi: 10.1158/0008-5472.CAN-08-3953. Epub Mar. 10, 2009.
Seeliger, et al. High yield bacterial expression of active c-Abl and c-Src tyrosine kinases. Protein Sci. Dec. 2005;14(12):3135-9. Epub Oct. 31, 2005.
Shan, et al. A conserved protonation-dependent switch controls drug binding in the Abl kinase. Proc Natl Acad Sci U S A. Jan. 6, 2009;106(1):139-44. doi: 10.1073/pnas.0811223106. Epub Dec. 24, 2008.
Shen. Optical Second Harmonic Generation at Interfaces. Annual Review of Physical Chemistry. 1989; 40(1):327-350.
Shen. Surface properties probed by second-harmonic and sum-frequency generation. Nature. 1989; 337: 20 519-525.
Shen. The Principles of Nonlinear Optics, John Wiley & Sons, New York. 1984.
Shen.. Surface properties probed by second-harmonic and sum-frequency generation. Nature. 1989; 337: 20 519-525.
Shih, et al. Evidence that genetic instability occurs at an early stage of colorectal tumorigenesis. Cancer Res. Feb. 1, 2001;61(3):818-22.
Shnek, et al. Specific Protein Attachment to Artificial Membranes via Coordination to Lipid-Bound Copper (II). Langmuir. 1994; 10:2382-2388.
Sicheri, et al. Structures of Src-family tyrosine kinases. Current Opinion in Structural Biology. 1997; 7:777-785.
Sicheri. Crystal structure of the Src family tyrosine kinase Hck. Nature. 1997; 3 85:602-609.
Sigal, et al. A self-assembled monolayer for the binding and study of histidine-tagged proteins by surface plasmon resonance. Anal Chem. Feb. 1, 1996;68(3):490-7.
Simard, et al. A new screening assay for allosteric inhibitors of cSrc. Nat Chem Biol. Jun. 2009;5(6):394-6. doi: 10.1038/nchembio.162. Epub Apr. 26, 2009.

(56) References Cited

OTHER PUBLICATIONS

Simard, et al. Development of a fluorescent-tagged kinase assay system for the detection and characterization of allosteric kinase inhibitors. J Am Chem Soc. Sep. 23, 2009;131(37):13286-96. doi: 10.1021/ja902010p.
Singer, et al. Measurements of molecular second-order optical susceptibilities using dc-induced second harmonic generation. J. Chem. Phys. 1981; 75:3572-3580.
Singhvi, et al. Engineering cell shape and function. Science. Apr. 29, 1994;264(5159):696-8.
Sittampalam, et al. High-throughput screening: advances in assay technologies. Curr Opin Chem Biol. Oct. 1997;1(3):384-91.
Smit, et al. Semiautomated Dna mutation analysis using a robotic workstation and molecular beacons. Clin Chem. Apr. 2001;47(4):739-44.
Smith, et al. Libraries of peptides and proteins displayed on filamentous phage. Methods Enzymol. 1993;217:228-57.
Smith. Surface presentation of protein epitopes using bacteriophage expression systems. Curr Opin Biotechnol. Oct. 1991;2(5):668-73.
Sokol, et al. Real time detection of DNA.RNA hybridization in living cells. Proc Natl Acad Sci U S A. Sep. 29, 1998;95(20):11538-43.
Sonnichsen, et al. Spectroscopy of single metallic nanoparticles using total internal reflection microscopy. Appl. Phys. Left. 2000; 77(19):2949-2951.
Spargo, et al. Spatially controlled adhesion, spreading, and differentiation of endothelial cells on self-assembled molecular monolayers. Proc Natl Acad Sci U S A. Nov. 8, 1994;91(23):11070-4.
Sproat, et al. The synthesis of protected 5'-mercapto-2',5'-dideoxyribonucleoside-3'- O-phosphoramidites; uses of 5'-mercapto-oligodeoxyribonucleotides. Nucleic Acids Res. Jun. 25, 1987;15(12):4837-48.
Srivastava, et al. Kinetics of molecular transport across a liposome bilayer. Chem. Phys. Lett. 1998; 292 (3): 345-351.
Steemers, et al. Screening unlabeled DNA targets with randomly ordered fiber-optic gene arrays. Nat Biotechnol. Jan. 2000;18(1):91-4.
Steuerwald, et al. Analysis of gene expression in single oocytes and embryos by real-time rapid cycle fluorescence monitored Rt-Pcr. Mol Hum Reprod. Nov. 1999;5(11):1034-9.
Stricker, et al. Neoplasia. Robbins and Cotran's Pathologic Basis of Disease, 8th. Eds. (Elsevier): Chicago, 2010. Ch 7:279-286.
Strouse, et al. Using molecular beacons to quantify low levels of type I endonuclease activity. Biopharm. 2000; 13:40-47.
Suh, et al. Morphology dependent contrast measurements of microscopically textured germanium films. Proc. SPIE. 1983; 382:199-201.
Summerer, et al. A genetically encoded fluorescent amino acid. Proc Natl Acad Sci U S A. Jun. 27, 2006;103(26):9785-9. Epub Jun. 19, 2006.
Suslick, et al. Push-pull porphyrins as nonlinear optical materials. J. Am. Chem. Soc. 1992; 114:6928-6930.
Szemes, et al. Development of a multiplex AmpliDet RNA assay for simultaneous detection and typing of potato virus Y isolates. J Virol Methods. Feb. 2002;100(1-2):83-96.
Szuhai, et al. A novel strategy for human papillomavirus detection and genotyping with SybrGreen and molecular beacon polymerase chain reaction. Am J Pathol. Nov. 2001;159(5):1651-60.
Szuhai, et al. Simultaneous A8344G heteroplasmy and mitochondrial DNA copy No. quantification in myoclonus epilepsy and ragged-red fibers (MERRF) syndrome by a multiplex molecular beacon based real-time fluorescence PCR. Nucleic Acids Res. Feb. 1, 2001;29(3):E13.
Takagi, et al. Global conformational rearrangements in integrin extracellular domains in outside-in and inside-out signaling. Cell. Sep. 6, 2002;110(5):599-11.
Tan, et al. Molecular beacons: a novel DNA probe for nucleic acid and protein studies. Chemistry. Apr. 3, 2000;6(7):1107-11.
Tanaka, et al. Interfering with RAS-effector protein interactions prevent RAS-dependent tumour initiation and causes stop-start control of cancer growth. Oncogene. Nov. 11, 2010;29(45):6064-70. doi: 10.1038/onc.2010.346. Epub Sep. 6, 2010.
Tapp, et al. Homogeneous scoring of single-nucleotide polymorphisms: comparison of the 5'-nuclease TaqMan assay and Molecular Beacon probes. Biotechniques. Apr. 2000;28(4):732-8.
Thelwell, et al. Mode of action and application of Scorpion primers to mutation detection. Nucleic Acids Res. Oct. 1, 2000;28(19):3752-61.
Theodossiou, et al.Thermally Induced Irreversible Conformational Changes in Collagen Probed by Optical Second Harmonic Generation and Laser-induced Fluorescence, 2002; 17:34-41.
Thomas. Raman spectroscopy of protein and nucleic acid assemblies. Annual Review of Biophysics and Biomolecular Structure. 1999; 28:1-27.
Tom, et al. Development of modulators of alpha-synuclein conformation for Parkinson's disease therapeutics. Biodesy, LLC. Max Planck Institute for Biophysical Chemistry. MJFF poster. Oct. 2010.
Tung, et al. In vivo imaging of proteolytic enzyme activity using a novel molecular reporter. Cancer Res. Sep. 1, 2000;60(17):4953-8.
Turcatti, et al. Probing the structure and function of the tachykinin neurokinin-2 receptor through biosynthetic incorporation of fluorescent amino acids at specific sites. J Biol Chem. Aug. 16, 1996;271(33):19991-8.
Tyagi, et al. Molecular beacons: probes that fluoresce upon hybridization. Nat Biotechnol. Mar. 1996;14(3):303-8.
Tyagi, et al. Multicolor molecular beacons for allele discrimination. Nat Biotechnol. Jan. 1998;16(1):49-53.
Tyagi, et al. Wavelength-shifting molecular beacons. Nat Biotechnol. Nov. 2000;18(11):1191-6.
Uddin, et al. A fiber optic biosensor for fluorimetric detection of triple-helical DNA. Nucleic Acids Res. Oct. 15, 1997;25(20):4139-46.
Uhlmann, et al. PNA: Synthetic polyamide nucleic acids with unusual binding properties. Angewandte Chemie-International Edition. 1998; 37:2797-2823.
Uhlmann. Peptide nucleic acids (PNA) and PNA-DNA chimeras: from high binding affinity towards biological function. Biol Chem. 1998; 379:1045-52.
Valentin, et al. CXCR4 mediates entry and productive infection of syncytia-inducing (X4) HIV-1 strains in primary macrophages. Virology. Apr. 10, 2000;269(2):294-304.
Van Beuningen, et al. Development of a high-throughput detection system for HIV-1 using real-time NASBA based on molecular beacons. Proceedings—SPIE the International Society for Optical Engineering. 2001; 4264, 66-71.
Van Elshocht, et al. Chiral 1,1E-binaphthyl-based helical polymers as nonlinear optical materials. Chemical Physics Letters. 1999; 309:315-320.
Van Schie, et al. Semiautomated clone verification by real-time PCR using molecular beacons. Biotechniques. Dec. 2000;29(6):1296-300, 1302-4, 1306 passim.
Vance, et al. Enormous Hyper-Rayleigh Scattering from Nanocrystalline Gold Particle Suspensions. J. Phys. Chem. B. 1999; 102:10091-93.
Verdine, et al. The challenge of drugging undruggable targets in cancer: lessons learned from targeting BCL-2 family members. Clin Cancer Res. Dec. 15, 2007;13(24):7264-70.
Vet, et al. Multiplex detection of four pathogenic retroviruses using molecular beacons. Proc Natl Acad Sci U S A. May 25, 1999;96(11):6394-9.
Villiers, et al. Peptide-protein microarrays and surface plasmon resonance detection: Biosensors for versatile biomolecular interaction analysis. Biosensors and Bioelectronics. 2010; 26:1554-1559.
Vogelstein, et al. Digital PCR. Proc Natl Acad Sci U S A. Aug. 3, 1999;96(16):9236-41.
Vogtherr, et al. NMR characterization of kinase p38 dynamics in free and ligand-bound forms. Angew Chem Int Ed Engl. Jan. 30, 2006;45(6):993-7.
Walt. Techview: molecular biology. Bead-based fiber-optic arrays. Science. Jan. 21, 2000;287(5452):451-2.
Wang, et al. In situ, nonlinear optical probe of Surfactant Adsorption on the Surface of Microparticles in Colloids. Langmuir 2000, 16, 2475-2481.

(56) References Cited

OTHER PUBLICATIONS

Wang, et al. Polarity of liquid interfaces by second harmonic generation spectroscopy, 1997, J Phys Chem a, 101, 713-718.
Wang. DNA biosensors based on peptide nucleic acid (PNA) recognition layers. A review. Biosens Bioelectron. 1998; 13:757-62.
Wartchow, et al. Assaying protein conformational change in real time—a novel approach for target-based drug discovery. Biodesy, LLC. SLAS2012 Roche poster. Feb. 6-8, 2012.
Watson, et al. Technology for microarray analysis of gene expression. Curr Opin Biotechnol. Dec. 1998;9(6):609-14.
Weber, et al. Synthesis and spectral properties of a hydrophobic fluorescent probe: 6- propionyl-2-(dimethylamino)naphthalene. Biochemistry. Jul. 10, 1979;18(14):3075-8.
Weidner, et al. Sum frequency generation and solid-state NMR study of the structure, orientation, and dynamics of polystyrene-adsorbed peptides. Proc Natl Acad Sci U S A. Jul. 27, 2010;107(30):13288-93. doi: 10.1073/pnas.1003832107. Epub Jul. 13, 2010.
Weisz. Polyamides as artificial regulators of gene expression. Angew. Chem. Int. Ed. Eng. 1997; 36:2592-2594.
Weljie, et al. Protein conformational changes studied by diffusion NMR spectroscopy: Application to helix-loop-helix calcium binding proteins. Protein Science. 2003; 12:228-235.
Wennerberg, et al. The Ras superfamily at a glance. J Cell Sci. Mar. 1, 2005 ;118(Pt 5):843-6.
Wettstein, et al. Expression of a class II major histocompatibility complex (MHC) heterodimer in a lipid-linked form with enhanced peptide/soluble MHC complex formation at low pH. J Exp Med. Jul. 1, 1991;174(1):219-28.
Whitcombe, et al. Detection of PCR products using self-probing amplicons and fluorescence. Nat Biotechnol. Aug. 1999;17(8):804-7.
Winner, et al. In vivo demonstration that alpha-synuclein oligomers are toxic. Proc Natl Acad Sci U S A. Mar. 8, 2011;108(10):4194-9. doi: 10.1073/pnas.1100976108. Epub Feb. 15, 2011.
Wittung, et al. Recognition of double-stranded DNA by peptide nucleic acid. Nucleosid. Nucleotid. 1997; 16"599-602.
Wu, et al. Protein immobilization on Ni(II) ion patterns prepared by microcontact printing and dip-pen nanolithography. ACS Nano.Feb. 23, 2010;4(2):1083-91. doi: 10.1021/nn901270c.
Xiao, et al. A DNA damage signal is required for p53 to activate gadd45. Cancer Res. Mar. 15, 2000;60(6):1711-9.
Xie, et al. Adding amino acids to the genetic repertoire. Curr Opin Chem Biol. Dec. 2005;9(6):548-54. Epub Nov. 2, 2005.
Xie, et al. Innovation: a chemical toolkit for proteins—an expanded genetic code. Nature Reviews Molecular Cell Biology. 2006; 7:775-782.
Xu, et al. Crystal structures of c-Src reveal features of its autoinhibitory mechanism. Molecular Cell 3, 629-638 (1999).
Xu, et al. Three-dimensional structure of the tyrosine kinase c-Src. Nature. 1997 385:595-602.
Yamamoto, et al. Molecular beacon aptamer fluoresces in the presence of Tat protein of HIV-1. Genes Cells. May 2000;5(5):389-96.
Yang, et al. Spectral broadening of ultrashort pulses in a nonlinear medium. Opt Left. Nov. 1, 1984;9(11):510-2.
Yang, et al. Surface second harmonic generation (SSHG)—a new scheme for immunoassay. Proceedings of the SPIE. 1996; 2676:290-296. http://dx.doi.org/10.1117/12.238808.
Yates, et al. Quantitative detection of hepatitis B virus DNA by real-time nucleic acid sequence-based amplification with molecular beacon detection. J Clin Microbiol. Oct. 2001;39(10):3656-65.
Yellen. The moving parts of voltage-gated ion channels. Q Rev Biophys. Aug. 1998;31(3):239-95.
Ying, et al. Two-state model of conformational fluctuation in a DNA hairpin-loop. Chemical Physics Letters. 2001; 334:145-150.
You, et al. Affinity capturing for targeting proteins into micro and nanostructures. Anal Bioanal Chem. Mar. 2009;393(6-7):1563-70. doi: 10.1007/s00216-008-2595-6. Epub Jan. 20, 2009.
Zhang, et al. A chemilluminescence fiber-optic biosensor for detection of DNA hybridization. Anal. Lett. 1999; 32:2725-2736.
Zhang, et al. A new strategy for the site-specific modifications of proteins in vivo. Biochemistry. 2003; 42:6735-6746.
Zhang, et al. Design of a Molecular Beacon DNA Probe with Two Fluorophores. Angew Chem Int Ed Engl. Jan. 19, 2001;40(2):402-405.
Zhang, et al. Measuring recent thymic emigrants in blood of normal and HIV-1-infected individuals before and after effective therapy. J Exp Med. Sep. 6, 1999;190(5):725-32.
Zhang, et al. Targeting cancer with small molecule kinase inhibitors. Nat Rev Cancer. Jan. 2009;9(1):28-39. doi: 10.1038/nrc2559.
Zhu, et al Inhibition of vascular endothelial growth factor-induced receptor activation with anti-kinase insert domain-containing receptor single-chain antibodies from a phage display library. Cancer Res. Aug. 1, 1998;58(15):3209-14.
Zhuang, et al. Mapping molecular orientation and conformation at interfaces by surface nonlinear optics. Physical Review B. 19991 59(19):12632-12640.
Zimdars, et al. Static and Dynamic Solvation at the Air/Water Interface. Journal of Physical Chemistry B. 2001; 105:3993-4002.
Zuckermann, et al. Efficient methods for attachment of thiol specific probes to the 31-ends of synthetic oligodeoxyribonucleotides. Nucleic Acids Res. Jul. 10, 1987;15(13):5305-21.
Notice of Allowance mailed on May 6, 2013 for U.S. Appl. No. 12/571,342, filed Sep. 30, 2009, 9 pages.
Notice of Allowance mailed on Oct. 10, 2014 for U.S. Appl. 14/482,899, filed Sep. 10, 2014, 12 pages.
Office action dated Jan. 30, 2015 for U.S. Appl. No. 13/834,521.
Office action dated Apr. 14, 2015 for U.S. Appl. No. 13/834,809.
Office action dated Apr. 21, 2015 for U.S. Appl. No. 13/838,340.
Office action dated Apr. 21, 2015 for U.S. Appl. No. 13/838,491.
Office action dated Sep. 15, 2015 for U.S. Appl. No. 13/834,521.
Office action dated Sep. 25, 2015 for U.S. Appl. No. 13/838,753.
Paige, et al. Estrogen receptor (ER) modulators each induce distinct conformational changes in ER alpha and ER beta. Proc Natl Acad Sci U S A. Mar. 30, 1999;96(7):3999-4004.
Request for Continued Examination filed on Jan. 13, 2009 for U.S. Appl. No. 11/327,199, filed Jan. 5, 2006, 6 pages.
Request for Continued Examination filed on Jul. 16, 2012 for U.S. Appl. No. 12/571,342, filed Sep. 30, 2009, 10 pages.
Response to Non-Final Office Action filed on Apr. 1, 2013 for U.S. Appl. No. 12/571,342, filed Sep. 30, 2009, 9 pages.
Response to Non-Final Office Action filed on Aug. 18, 2011 for U.S. Appl. No. 12/571,342, filed Sep. 30, 2009, 6 pages.
Response to Non-Final Office Action filed on Dec. 14, 2007 for U.S. Appl. No. 11/327,199, filed Jan. 5, 2006, 8 pages.
Seok, et al. Topology of allosteric regulation of lactose permease. Proc Natl Acad Sci U S A. Dec. 9, 1997;94(25):13515-9.

CLASSIFICATION OF KINASE INHIBITORS USING NONLINEAR OPTICAL TECHNIQUES

CROSS-REFERENCE TO RELATED APPLICATIONS

This application claims priority to U.S. Provisional Patent Application No. 61/454,868, filed Mar. 21, 2011 and U.S. Provisional Patent Application No. 61/595,123, filed Feb. 5, 2012, the disclosures of which are incorporated by reference herein in their entireties.

STATEMENT AS TO FEDERALLY SPONSORED RESEARCH

This invention was made with the support of the United States government under SBIR grant number IIP-1142241 from the National Science Foundation.

SEQUENCE LISTING

The instant application contains a Sequence Listing which has been submitted electronically in ASCII format and is hereby incorporated by reference in its entirety. Said ASCII copy, created on Nov. 6, 2013, is named 27484-704.831_SL.txt and is 1,050 bytes in size.

FIELD OF THE INVENTION

The invention relates to the field of molecular detection in general and kinase protein conformational structure detection in particular.

BACKGROUND

Kinases are one of the main classes of drug targets with at least 30 distinct targets now present in clinical trials[4,5]. The vast majority of these drugs, typically inhibitors of kinase activity, are being investigated for the treatment of cancer. Traditionally, kinase inhibitors were designed to inhibit ATP binding and thus prevent protein activity; most kinase drugs, known as type I inhibitors, mimic and bind to the ATP binding site, directly competing with ATP. Type I inhibitors stabilize the activation loop, an important structural element that determines the protein's activity, in an active conformation (FIG. 2, right). In contrast, type II inhibitors (e.g., Gleevec and sorafenib), which were first discovered serendipitously about a decade ago, cause the activation loop to shift to an inactive conformation (FIG. 2, left). They bind partly to the ATP binding site and partly to an additional hydrophobic pocket that is revealed in the inactive conformation.[6-10] The intense current interest in type II inhibitors is the result of five main factors.[4,5,11] First, the striking clinical success of Gleevec (imatinib), a type II inhibitor, in treating chronic-phase Chronic Myeloid Leukemia (CML) is fueling their demand. Second, the interactions of type II inhibitors in the hydrophobic pocket are more unique structurally, across kinases in the kinome, than those in the ATP binding pocket. As a result, type II inhibitors are expected to exhibit significantly better selectivity and slower off-rates in general. Third, type II inhibitors offer a route to expand the chemical space of kinase drugs because the scaffolds of many compound libraries have already been exploited for type I inhibitors. Fourth, there is a critical need for new type II inhibitors that can overcome mutational resistance; cocktails will likely become the dominant treatment paradigm. Fifth, although type II inhibitors have been identified against a handful of kinases, they have not been identified yet for the other ~500 kinases, leaving open the tantalizing possibility of developing Gleevec-like drugs for many other cancers and diseases.

Unfortunately, although demand for novel type II inhibitors is intense, identifying them is difficult.[4,12,13] They are often overlooked in traditional enzymatic assays because of their low affinity for active, phosphorylated kinases. The most direct way currently to identify type II inhibitors is by X-ray crystallography, whose throughput is, at best, about 100 co-structures per month. However, the throughput demand for a screen that can identify them is much higher. Therefore, a critical need exists for a new technique that is both high-throughput and can readily identify type II inhibitors.

The invention described herein addresses these problems and provides additional benefits as well.

Throughout this specification, various patents, patent applications and other types of publications (e.g., journal articles) are referenced. The disclosure of all patents, patent applications, and publications cited herein are hereby incorporated by reference in their entirety for all purposes.

SUMMARY OF THE INVENTION

The invention provided herein discloses, inter alia, methods for classifying a kinase inhibitor, including generic versions of brand name drug kinase inhibitors, as belonging to either the type I or type II class of kinase inhibitors.

In some aspects, provided herein are methods for classifying a kinase inhibitor as a type I or type II kinase inhibitor based on a conformational change that the kinase inhibitor induces in the structure of a kinase labeled with a second harmonic-active label, wherein the label has a net orientation at an interface, the method comprising: (a) contacting the kinase with a kinase inhibitor, wherein the kinase specifically interacts with said kinase inhibitor; (b) detecting an interaction between the kinase and said kinase inhibitor by measuring a first signal or signal change generated by the second harmonic-active label using a surface-selective technique, wherein the first signal or signal change indicates a conformational change in the structure of the kinase that is specific for the kinase inhibitor; and (c) classifying the kinase inhibitor as a type I or type II kinase inhibitor by comparing the first signal or signal change of (b) with a second signal or signal change detected by an interaction between the kinase and a known type I or type II inhibitor of the kinase, wherein the second signal or signal change indicates a conformational change in the structure of the kinase that is specific for the known type I or type II inhibitor of the kinase. In some embodiments, the type II kinase inhibitor is imatinib. In some embodiments, the type I kinase inhibitor is dasatinib. In some embodiments, the kinase is attached to a surface. In some embodiments, the surface is selected from the group consisting of: a glass surface, a plastic surface, a metal surface, a latex surface, a rubber surface, a ceramic surface, a polymeric surface, a supported lipid bilayer surface, a polypropylene surface, a polyvinylidene difluoride surface, a polyethylene surface. In some embodiments, the surface is derivatized with oligo-PEG molecules or lipids. In some embodiments, the oligo-PEG molecules or lipids are Ni-NTA-bearing oligo-PEG molecules or Ni-NTA-bearing lipids. In some embodiments, the kinase comprises an affinity tag. In some embodiments, the conformational change in the structure of the kinase is detected in real time. In some embodiments of any of the embodiments described above, the kinase inhibitor is a small molecule chemical compound, a non-antibody inhibitory peptide, an antibody, or any combination thereof. In some embodiments of any of the embodiments described above, the second harmonic-active label is bound to the kinase by one or more sulfhydryl groups on the surface of the kinase. In some embodiments, said one or more sulfhydryl groups are native sulfhydryl groups. In some embodiments, said one or more sulfhydryl groups are engineered sulfhydryl groups. In some embodiments of any of the embodiments described above, said one or more sulfhydryl groups are not located within the kinase activation loop. In some embodiments of any of the embodiments described above, the second harmonic-active label is selected from the group consisting of PyMPO maleimide, PyMPO-NHS, PyMPO-succinimidyl ester, Badan, and Acrylodan. In some embodiments of any of the embodiments described above, the second harmonic-active label is an unnatural amino acid. In some embodiments, the unnatural amino acid is Aladan. In some embodiments of any of the embodiments described above, the kinase is Abl kinase.

In some aspects, provided herein are methods for comparing the conformational changes induced by a generic drug and a branded drug in the structure of a kinase labeled with a second harmonic-active label, wherein the label has a net orientation at an interface, and wherein the branded drug is a type I or type II kinase inhibitor, the method comprising: contacting the kinase with the branded drug, wherein the kinase specifically interacts with the branded drug; detecting an interaction between the kinase and the branded drug by measuring a first signal or signal change generated by the second harmonic-active label using a surface-selective technique, wherein the first signal change indicates a conformational change in the structure of the kinase that is specific for the branded drug; contacting the kinase with the generic drug, wherein the kinase specifically interacts with the generic drug; and detecting an interaction between the kinase and the generic drug by measuring a second signal or signal change generated by the second harmonic-active label using a surface-selective technique, wherein the second signal or signal change indicates a conformational change in the structure of the kinase that is specific for the generic drug and wherein the second signal or signal change is compared to the first signal or signal change to determine whether the conformational change induced in the kinase by the generic drug is identical to the change induced by the branded drug. In some embodiments, the branded type II inhibitor is imatinib. In some embodiments, the generic drug is a biosimilar or a small molecule chemical compound. In some embodiments, the kinase is attached to a surface. In some embodiments, the surface is selected from the group consisting of: a glass surface, a plastic surface, a metal surface, a latex surface, a rubber surface, a ceramic surface, a polymeric surface, a supported lipid bilayer surface, a polypropylene surface, a polyvinylidene difluoride surface, a polyethylene surface. In some embodiments, the surface is derivatized with oligo-PEG molecules or lipids. In some embodiments, the oligo-PEG molecules or lipids are Ni-NTA-bearing oligo-PEG molecules or Ni-NTA-bearing lipids. In some embodiments, the kinase comprises an affinity tag. In some embodiments, the conformational change in the structure of the kinase is detected in real time. In some embodiments of any of the embodiments described above, the kinase inhibitor is a small molecule chemical compound, a non-antibody inhibitory peptide, an antibody, or any combination thereof. In some embodiments of any of the embodiments described above, the second harmonic-active label is bound to the kinase by one or more sulfhydryl groups on the surface of the kinase. In some embodiments, said one or more sulfhydryl groups are native sulfhydryl groups. In some embodiments, said one or more sulfhydryl groups are engineered sulfhydryl groups. In some embodiments of any of the embodiments described above, said one or more sulfhydryl groups are not located within the kinase activation loop. In some embodiments of any of the embodiments described above, the second harmonic-active label is selected from the group consisting of PyMPO maleimide, PyMPO-NHS, PyMPO-succinimidyl ester, Badan, and Acrylodan. In some embodiments of any of the embodiments described above, the second harmonic-active label is an unnatural amino acid. In some embodiments, the unnatural amino acid is Aladan. In some embodiments of any of the embodiments described above, the kinase is Abl kinase.

In some aspects, provided herein are methods for classifying an unknown candidate kinase inhibitor as a type I or type II kinase inhibitor based on a conformational change that the candidate kinase inhibitor induces in the structure of a kinase labeled with a second harmonic-active label, wherein the label has a net orientation at an interface, and wherein the kinase has no known type I or type II inhibitors, the method comprising: (a) contacting the kinase with the candidate kinase inhibitor, wherein the kinase specifically interacts with said candidate kinase inhibitor; (b) detecting an interaction between the kinase and said candidate kinase inhibitor by measuring a signal or signal change generated by the second harmonic-active label using a surface-selective technique, wherein the signal or signal change indicates a conformational change in the structure of the kinase that is specific for the candidate kinase inhibitor; (c) comparing the signal or signal change detected in (b) with a signal or signal change produced by the interaction between a known type I or type II kinase inhibitor and a kinase known to be inhibited by said known type I or type II kinase inhibitor to classify the candidate kinase inhibitor based on the conformational change it induces in the structure of the kinase. In some embodiments, the known type I or type II kinase inhibitor is a type II kinase inhibitor. In some embodiments, the type II kinase inhibitor is imatinib. In some embodiments of any of the embodiments described above, the kinase known to be inhibited by said known type I or type II kinase inhibitor is abl kinase. In some embodiments, the kinase is attached to a surface. In some embodiments, the surface is selected from the group consisting of: a glass surface, a plastic surface, a metal surface, a latex surface, a rubber surface, a ceramic surface, a polymeric surface, a supported lipid bilayer surface, a polypropylene surface, a polyvinylidene difluoride surface, a polyethylene surface. In some embodiments, the surface is derivatized with oligo-PEG molecules or lipids. In some embodiments, the oligo-PEG molecules or lipids are Ni-NTA-bearing oligo-PEG molecules or Ni-NTA-bearing lipids. In some embodiments, the kinase comprises an affinity tag. In some embodiments, the conformational change in the structure of the kinase is detected in real time. In some embodiments of any of the embodiments described above, the candidate kinase inhibitor is a small molecule chemical compound, a non-antibody inhibitory peptide, an antibody, or any combination thereof. In some embodiments of any of the embodiments described above, the second harmonic-active label is bound to the kinase by one or more sulfhydryl groups on the surface of the kinase. In some embodiments, said one or more sulfhydryl groups are native sulfhydryl groups. In some embodiments, said one or more sulfhydryl groups are engineered sulfhydryl groups. In some embodiments of any of the embodiments described above, said one or more sulfhydryl groups are not located within the kinase activation loop. In some embodiments of any of the embodiments described above, the second harmonic-active label is selected from the group consisting of PyMPO maleimide, PyMPO-NHS, PyMPO-succinimidyl ester, Badan, and Acrylodan. In some embodiments of any of the embodiments described above, the second harmonic-active label is an unnatural amino acid. In some embodiments, the unnatural amino acid is Aladan.

It is to be understood that one, some, or all of the properties of the various embodiments described herein may be combined to form other embodiments of the present invention. These and other aspects of the invention will become apparent to one of skill in the art.

DETAILED DESCRIPTION

Figure 1:
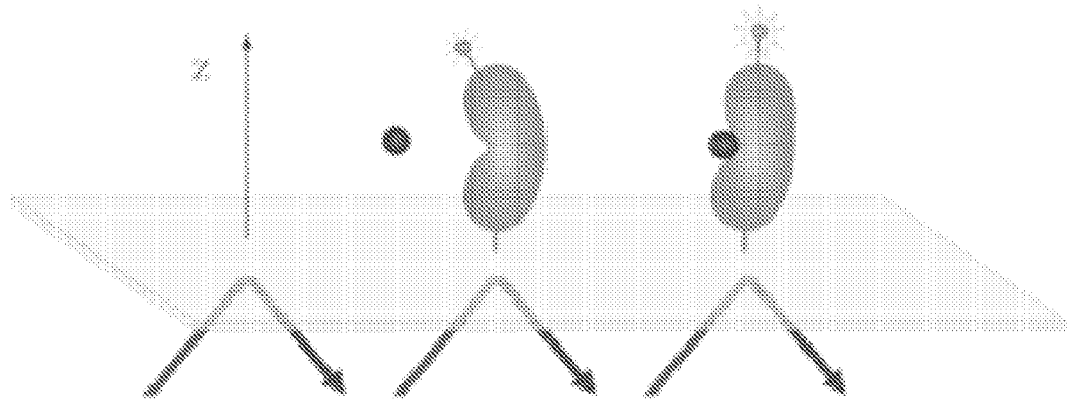
FIG. 1 depicts a schematic of the detection process for detecting conformational changes in proteins. Incident red light strikes the surface and through total internal reflection creates an evanescent wave polarized normal to the plane of the surface and traveling just a short distance from the surface (left). Labeled protein bound to surface with baseline signal dependent on the position of the dye relative to this normal (center). A conformational change that brings the label towards the normal of the evanescent wave results in a signal increase (left).
Figure 2:
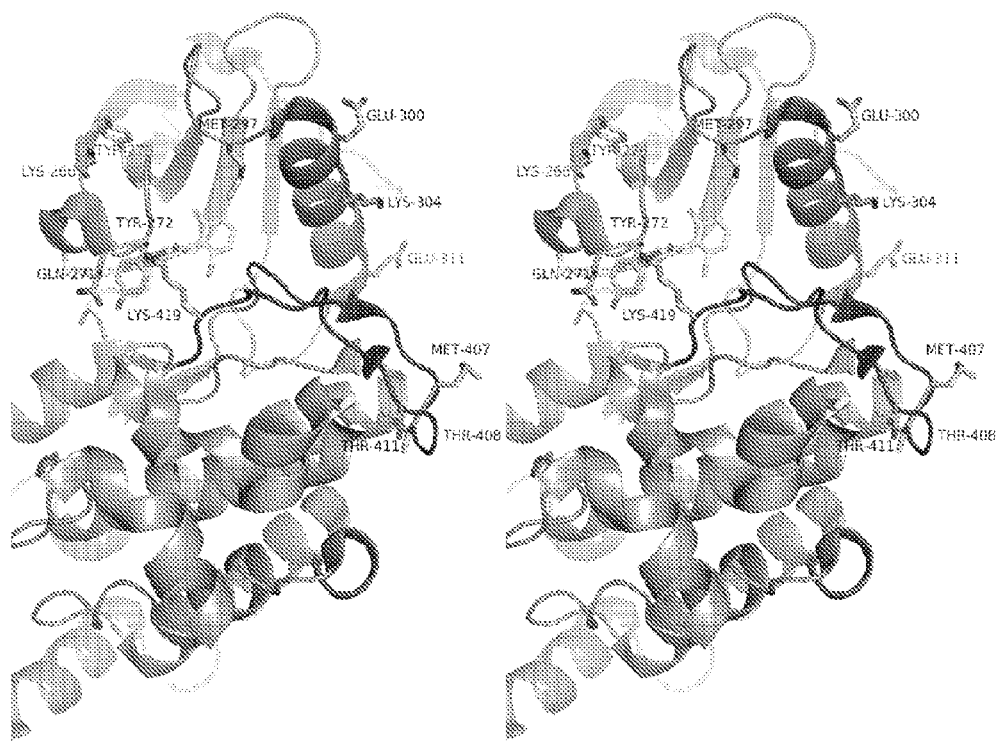
FIG. 2 depicts drugs classified by the structural effect they ellicit on the activation loop (black) of a kinase. Most kinase drugs, known as type I inhibitors, bind to the ATP binding site, mimic and directly compete with ATP and stabilize the activation loop in an active conformation (right). In contrast, type II inhibitors (e.g., Gleevec and sorafenib) cause the activation loop to shift to an inactive conformation (left). They bind partly to the ATP binding site and to an additional hydrophobic pocket that is revealed by the activation loop in the inactive conformation.

The present invention discloses, inter alia, methods for labeling a kinase with an SHG-active probe for detection by second-harmonic or sum-frequency generation in order to classify a kinase inhibitor as belonging to either the type I or type H class of kinase inhibitors.

The aim of structure-based drug screening and basic studies of the mechanism of biological molecules requires a tool that can measure structure and structural change of biological molecules as they bind to ligands, drugs, or other binding partners. Present techniques for determining structural change are mainly confined to NMR (Nuclear Magnetic Resonance) and X-ray crystallography. Neither of these techniques is suitable for measuring structural change in real time. Moreover, they are time- and labor-intensive and unsuitable for wide scale use in drug screening. Furthermore, there are many proteins that are difficult to crystallize (e.g., membrane proteins) and thus many whose structures have not been determined.

The present invention uses second harmonic generation techniques to classify candidate kinase inhibitors as either type I or type II inhibitors based on the structural change induced in an SHG-active probe-labeled kinase by a kinase inhibitor. The inventors have discovered, inter alia, that known type I and type II kinase inhibitors induce characteristic and reproducible "signature" conformational changes in kinase structure which can be measured by SHG. The methods of the present application, therefore, represent an improvement over what has previously been practiced in the art, in that classification of kinase inhibitors using the instantly described methods can be performed as high-throughput assays and in real time, in contrast to traditional methods which often require long periods of time to obtain results and, at best, provide only a snapshot of a protein's conformational dynamics upon binding to a ligand or binding partner.

I. GENERAL TECHNIQUES

The practice of the present invention will employ, unless otherwise indicated, conventional techniques of molecular biology (including recombinant techniques), microbiology, cell biology, biochemistry, nonlinear optics detection and measurement, and immunology, which are within the skill of the art. Such techniques are explained fully in the literature, "*Molecular Cloning: A Laboratory Manual*", second edition (Sambrook et al., 1989); "*Oligonucleotide Synthesis*" (M. J. Gait, ed., 1984); "*Animal Cell Culture*" (R. I. Freshney, ed., 1987); "*Methods in Enzymology*" (Academic Press, Inc.); "*Current Protocols in Molecular Biology*" (F. M. Ausubel et al., eds., 1987, and periodic updates); "*PCR: The Polymerase Chain Reaction*", (Mullis et al., eds., 1994). Singleton et al., *Dictionary of Microbiology and Molecular Biology* 2nd ed., J. Wiley & Sons (New York, N.Y. 1994), March, "*Advanced Organic Chemistry Reactions, Mechanisms and Structure*" 4th ed., John Wiley & Sons (New York, N.Y. 1992), "*Bioconjugate Techniques*", Elsevier, (G. T. Hermanson 2008), and "Second-order nonlinear optical effects at surfaces and interfaces," in *Nonlinear Surface Electromagnetic Phenomena*, Elsevier (Eds. H. Ponath and G. I. Stegeman, 1991) provide one skilled in the art with a general guide to many of the terms used in the present application.

II. DEFINITIONS

As used herein "second harmonic" refers to a frequency of light that is twice the frequency of a fundamental beam of light.

As used herein, a molecule or material phase is "centrosymmetric" if there exists a point in space (the "center" or "inversion center") through which an inversion (x,y,z)->> (-x,-y,-z) of all atoms is performed that leaves the molecule or material unchanged. A non-centrosymmetric molecule or material lacks this center of inversion. For example, if the molecule is of uniform composition and spherical or cubic in shape, it is centrosymmetric. Centrosymmetric molecules or materials have no nonlinear susceptibility or hyperpolarizability, necessary for second harmonic, sum frequency and difference frequency generation.

As used herein, "surface-selective" refers to a non-linear optical technique such as second harmonic generation or sum/difference frequency generation or other surface-specific technique known in the art.

As used herein, "sum frequency generation" (SFG) is a nonlinear, optical technique whereby light at one frequency ($\Omega_1$) is mixed with light at another frequency ($\Omega_2$) to yield a response at the sum frequency ($\Omega_1+\Omega_2$) (Shen, 1984, 1989). For example, SFG is particularly useful for the detection of molecules at surfaces through their characteristic vibrational transitions and, in this case, is essentially a surface-selective infrared spectroscopy with $\Omega_1$ and $\Omega_2$ at visible and infrared frequencies.

A "nonlinear active moiety," as used herein, is a substance which possesses a hyperpolarizability.

"Second harmonic-active label," as used herein, refers to a nonlinear-active moiety, particle or molecule which can be attached (covalently or non-covalently) to a molecule (e.g., a protein, such as a kinase), particle or phase (e.g., lipid bilayer) in order to render it more nonlinear optical active.

"Hyperpolarizability" or "Nonlinear Susceptibility" as used herein refer to the properties of a molecule, particle, interface, or phase which allow for generation of nonlinear light. The terms "hyperpolarizability," "second-order nonlinear polarizability," and "nonlinear susceptibility" are sometimes used interchangeably.

As used herein, "nonlinear" refers to optical techniques capable of transforming the frequency of an incident light beam (a.k.a., the fundamental). The nonlinear beams are the higher order frequency beams which result from such a transformation, e.g. a second harmonic. In second harmonic, sum frequency or difference frequency generation, the nonlinear beams are generated coherently. In second harmonic generation (SHG), two photons of the fundamental beam are virtually scattered by the interface to produce one photon of the second harmonic. Also referred to herein as "nonlinear optical" or "surface-selective nonlinear."

The terms "nonlinear active" or "nonlinearly active" as used herein also refer to the general property of the ability of molecules, particles, an interface or a phase, to generate nonlinear optical radiation when driven by incident radiation beam or beams.

When referring herein to nonlinear optical methods, "detection" or "detecting" refers to those techniques by which the properties of surface-selective nonlinear optical radiation can be used to detect, measure or correlate properties of probe-target interactions (such as the interaction between a kinase and a candidate kinase inhibitor), or effects of the interactions, with properties of the nonlinear optical light (e.g., intensity, wavelength, polarization or other property common to electromagnetic radiation).

As used herein, "identical" with respect to SHG signals or changes in SHG signals (such as detected SHG signals or detected changes in SHG signals) means the average signal or signal change is identical in change, profile, intensity, polarization, and/or time within the average signal-to-noise ratio as determined by making multiple measurements of each signal or signal change caused by the binding of a kinase inhibitor (such as a type I or type II kinase inhibitor or an unknown candidate kinase inhibitor) to a kinase. In some embodiments, any of 1, 2, 3, 4, 5, 6, 7, 8, 9, 10, 11, 12, 13, 14, 15, or more measurements of each signal or signal change can be performed to determine if the signal or signal change is identical.

As used herein the term "conformational change" refers to the alteration of a biological species' (for example, a protein, such as a kinase) structural conformation.

As used herein, the term "protein" includes polypeptides, peptides, fragments of polypeptides, and fusion polypeptides.

As used herein, an "interface" is a region which generates a nonlinear optical signal or the region near a surface in which there are second harmonic-active labeled targets possessing a net orientation. An interface can also be composed of two surfaces, a surface in contact with a different medium (e.g., a glass surface in contact with an aqueous solution, a cell surface in contact with a buffer), or the region near the contact between two media of different physical or chemical properties.

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

III. COMPOSITIONS

A. Kinases

A kinase is a type of enzyme that transfers phosphate groups from high-energy donor molecules, such as ATP, to specific substrates, a process referred to as phosphorylation. One of the largest groups of kinases are protein kinases, which act on and modify the activity of specific proteins. Kinases are used extensively to transmit signals and control complex processes in cells. More than five hundred different kinases have been identified in humans. Their enormous diversity, as well as their role in signaling, makes them an object of study particularly with regard to disease states characterized by aberrant kinase expression or regulation.

Protein kinases contain a large flexible loop, called the activation loop or A-loop, whose conformation is believed to regulate kinase activity. In many kinases, the conformation of the A-loop is controlled by the phosphorylation of specific residues within this region (Johnson 1996). The activation loop generally begins with a conserved AspPheGly sequence and ends at a conserved AlaProGlu. In structures of inactive kinases, this loop often blocks either the substrate or ATP binding sites (Hubbard 1994; Mohammadi 1996; and McTigue 1999). Tyrosine kinases usually have one or two tyrosines in the loop, MAPK kinases have a T[DE]Y motif, which is phosphorylated on both T and Y, while most other kinases have a threonine within the loop.

The methods of the invention using the compositions described herein are broadly applicable to any protein kinase. These can include protein tyrosine kinases and protein serine kinases. Non-limiting examples of protein tyrosine kinases are pp 60c-src, p56lck, ZAP kinase, platelet derived growth factor receptor tyrosine kinase, Bcr-Abl, VEGF (vascular endothelial growth factor) receptor tyrosine kinase, and epidermal growth factor receptor tyrosine kinase, and epidermal growth factor receptor-like tyrosine kinases. Non-limiting examples of serine protein kinases applicable for use in the present invention include MAP (mitogen activated protein) kinase, protein kinase C, protein kinase A, Akt, and CDK (cyclin dependent protein kinase). In mammalian biology, protein kinases belonging to the mitogen activated protein kinase (MAPK) family are inappropriately activated in a variety of proliferative cell diseases (such as, for example, cancers) associated with the mutation of ras genes and deregulation of growth factor receptors (Magnuson et al., *Seminars in Cancer Biology*, 5:247-252 (1994)). MAP kinases are known in the art and a partial non-limiting list of such kinases includes abl, Aurora-A, Aurora-B, Aurora-C, ATK, bcr-abl, Blk, Brk, Btk, c-Kit, c-Met, c-Src, CDK1, CDK2, CDK4, CDK6, cRaf1, CSF1R, CSK, EGFR, ErbB2, ErbB3, ErbB4, ERK, Fak, fes, FGFR1, FGFR2, FGFR3, FGFR4, FGFR5, Fgr, FLK-4, Flt-1, Fms, Fps, Frk, Fyn, Hck, IGF-1R, INS-R, Jak, KDR, Lck, Lyn, MEK, p38, PDGFR, PIK, PKC, PYK2, Ros, Tie1, Tie2, Trk, Yes and Zap70. In some embodiments of the methods described herein, the kinase is abl kinase.

B. Kinase Inhibitors

Provided herein are methods for classifying kinase inhibitors as belonging to either the type I or type II class of kinase inhibitors. Type I kinase inhibitors recognize the active conformation of a kinase. They bind to the ATP-binding site by presenting one to three hydrogen bonds which mimic the hydrogen bonds normally formed by ATP. Without being bound to theory, it is believed that, in contrast to type I kinase inhibitors, type II kinase inhibitors recognize the inactive conformation of a kinase and can indirectly compete with ATP by occupying the hydrophobic pocket directly adjacent to the ATP-binding site. This hydrophobic pocket is created by the unique DFG-out conformation of the activation loop and is also known as the allosteric site. Type II inhibitors can modulate kinase activity in an allosteric way. While this is not necessary for functionality, some type II inhibitors are able to form a hydrogen bond directly to the ATP-binding site (Gotink & Verheul, *Angiogenesis*, 2010, 13(1): 1-14). As used herein, "allosteric inhibition" or "allosterically" refers to inhibition of a kinase by the binding of a kinase inhibitor to a site other than the protein's active site and to a site that partially includes the protein's active site. Accordingly, the kinase inhibitors for use in the present invention can either be type I inhibitors, which inhibit the active site of the kinase, or type II inhibitors, which can inhibit the kinase allosterically. In some embodiments, methods directed to distinguishing between allosteric and nonallosteric kinase inhibition are described herein.

Examples of known type I inhibitors include, without limitation, PD166326, sunitinib, PIK-39, dasatinib, and SB-431542.

Examples of known type II inhibitors include, without limitation, sorafenib, imatinib, nilotinib, doramapimod, AAL993, diaryl urea, indole amide, BIRB796, anilinoquinazoline, linifanib, AST-487, and 4-aminopyrimidinoquinazoline.

In some aspects, the kinase inhibitors for use in the methods described herein are not classified as either type I or type II inhibitors, but are unknown candidate kinase inhibitors. The kinase inhibitors for use in the methods described herein can be any of a small molecule chemical compound, an antibody, a non-antibody polypeptide, a carbohydrate, an inhibitory nucleic acid, or any combination thereof. In some embodiments, the kinase inhibitor is an antibody (such as a humanized antibody) or a fragment thereof. Alternatively, the kinase inhibitor may be a small molecule compound. In other embodiments, the kinase inhibitor can be a non-antibody polypeptide (such as an isolated non-antibody polypeptide). In some embodiments, kinase inhibitor is a peptide (for example, an isolated peptide).

1. Non-Antibody Binding Polypeptides

In some aspects, the kinase inhibitor is a non-antibody binding polypeptide. Binding polypeptides are polypeptides that bind, preferably specifically, to a kinase as either a type I or type II inhibitor as described herein. Binding polypeptides may be chemically synthesized using known polypeptide synthesis methodology or may be prepared and purified using recombinant technology. Binding polypeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such binding polypeptides that are capable of binding, preferably specifically, to a target kinase, such as any kinase described herein. Binding polypeptides may be identified without undue experimentation using well known techniques. In this regard, it is noted that techniques for screening polypeptide libraries for binding polypeptides that are capable of binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in Synthetic Peptides as Antigens, 130-149 (1986); Geysen et al., *J. Immunol. Meth.*, 102:259-274 (1987); Schoofs et al., *J. Immunol.*, 140:611-616 (1988), Cwirla, S. E. et al., (1990) *Proc. Natl. Acad. Sci. USA*, 87:6378; Lowman, H. B. et al., (1991) *Biochemistry*, 30:10832; Clackson, T. et al., (1991) *Nature*, 352: 624; Marks, J. D. et al., (1991), *J. Mol. Biol.*, 222:581; Kang, A. S. et al., (1991) *Proc. Natl. Acad. Sci. USA*, 88:8363, and Smith, G. P. (1991) *Current Opin. Biotechnol.*, 2:668).

Bacteriophage (phage) display is one well known technique which allows one to screen large polypeptide libraries to identify member(s) of those libraries which are capable of binding to a target polypeptide, such as a kinase for use in the methods disclosed herein. Phage display is a technique by which variant polypeptides are displayed as fusion proteins to the coat protein on the surface of bacteriophage particles (Scott, J. K. and Smith, G. P. (1990) *Science*, 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al., (1990) *Proc. Natl. Acad. Sci. USA*, 87:6378) or protein (Lowman, H. B. et al., (1991) *Biochemistry*, 30:10832; Clackson, T. et al., (1991) *Nature*, 352: 624; Marks, J. D. et al., (1991), *J. Mol. Biol.*, 222:581; Kang, A. S. et al., (1991) *Proc. Natl. Acad. Sci. USA*, 88:8363) libraries on phage have been used for screening millions of polypeptides or oligopeptides for ones with specific binding properties (Smith, G. P. (1991) *Current Opin. Biotechnol.*, 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663,143.

Although most phage display methods have used filamentous phage, lambdoid phage display systems (WO 95/34683; U.S. Pat. No. 5,627,024), T4 phage display systems (Ren et al., *Gene*, 215: 439 (1998); Zhu et al., *Cancer Research*, 58(15): 3209-3214 (1998); Jiang et al., *Infection & Immunity*, 65(11): 4770-4777 (1997); Ren et al., *Gene*, 195(2): 303-311 (1997); Ren, *Protein Sci.*, 5: 1833 (1996); Efimov et al., *Virus Genes*, 10: 173 (1995)) and T7 phage display systems (Smith & Scott, *Methods in Enzymology*, 217: 228-257 (1993); U.S. Pat. No. 5,766,905) are also known.

Additional improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphylococcus aureus* protein A as an affinity tag has also been reported (Li et al., (1998) *Mol. Biotech.*, 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432,018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

The binding polypeptides can be modified to enhance their inhibitory effect (including, for example, enhanced affinity, improved pharmacokinetic properties such as half-life, stability, and clearance rate, reduced toxicity, etc.). Such modifications include, for example, glycosylation, pegylation, substitution with non-naturally occurring but functionally equivalent amino acid, linking groups, etc.

2. Small Molecules

In some aspects, the kinase inhibitor is a small molecule chemical compound. Small molecules are preferably organic molecules other than binding polypeptides or antibodies as defined herein that bind, preferably specifically, to a kinase as either a type I or type II inhibitor as described herein. Organic small molecules may be identified and chemically synthesized using known methodology (see, e.g., PCT Publication Nos. WO00/00823 and WO00/39585). Organic small molecules are usually less than about 2000 Daltons in size, alternatively less than about 1500, 750, 500, 250 or 200 Daltons in size, wherein such organic small molecules that are capable of binding, preferably specifically, to a polypeptide as described herein may be identified without undue experimentation using well known techniques. In this regard, it is noted that techniques for screening organic small molecule libraries for molecules that are capable of binding to a polypeptide target are well known in the art (see, e.g., PCT Publication Nos. WO00/00823 and WO00/39585). Organic small molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

In some aspects, the small molecule chemical compound is a component of a combinatorial chemical library. Combinatorial chemical libraries are a collection of multiple species of chemical compounds comprised of smaller subunits or monomers. Combinatorial libraries come in a variety of sizes, ranging from a few hundred to many hundreds of thousand different species of chemical compounds. There are also a variety of library types, including oligomeric and polymeric libraries comprised of compounds such as carbohydrates, oligonucleotides, and small organic molecules, etc. Such libraries have a variety of uses, such as immobilization and chromatographic separation of chemical compounds, as well as uses for identifying and characterizing ligands capable of binding an acceptor molecule (such as a c-met protein) or mediating a biological activity of interest (such as, but not limited to, inhibition of cellular proliferation).

Various techniques for synthesizing libraries of compounds on solid-phase supports are known in the art. Solid-phase supports are typically polymeric objects with surfaces that are functionalized to bind with subunits or monomers to form the compounds of the library. Synthesis of one library typically involves a large number of solid-phase supports. To make a combinatorial library, solid-phase supports are reacted with one or more subunits of the compounds and with one or more numbers of reagents in a carefully controlled, predetermined sequence of chemical reactions. In other words, the library subunits are "grown" on the solid-phase supports. The larger the library, the greater the number of reactions required, complicating the task of keeping track of the chemical composition of the multiple species of compounds that make up the library. In some embodiments, the small molecules are less than about 2000 Daltons in size, alternatively less than about 1500, 750, 500, 250 or 200 Daltons in size.

The small molecule agents described in any of the aspects herein can be derived from any type of chemical reaction that can be carried out on a solid support. Such chemical reactions include, but are not limited to, 2+2 cycloadditions including trapping of butadiene; [2+3] cycloadditions including synthesis of isoxazolines, furans and modified peptides; acetal formation including immobilization of diols, aldehydes and ketones; aldol condensation including derivatization of aldehydes, synthesis of propanediols; benzoin condensation including derivatization of aldehydes; cyclo-condensations including benzodiazepines and hydantoins, thiazolidines, turn mimetics, porphyrins, phthalocyanines; Dieckmann cyclization including cyclization of diesters; Diels-Alder reaction including derivatization of acrylic acid; Electrophilic addition including addition of alcohols to alkenes; Grignard reaction including derivatization of aldehydes; Heck reaction including synthesis of disubstituted alkenes; Henry reaction including synthesis of nitrile oxides in situ (see 2+3 cycloaddition); catalytic hydrogenation including synthesis of pheromones and peptides (hydrogenation of alkenes); Michael reaction including synthesis of sulfanyl ketones, bicyclo[2.2.2]octanes; Mitsunobu reaction including synthesis of aryl ethers, peptidyl phosphonates and thioethers; nucleophilic aromatic substitutions including synthesis of quinolones; oxidation including synthesis of aldehydes and ketones; Pausen-Khand cycloaddition including cyclization of norbornadiene with pentynol; photochemical cyclization including synthesis of helicenes; reactions with organo-metallic compounds including derivatization of aldehydes and acyl chlorides; reduction with complex hydrides and tin compounds including reduction of carbonyl, carboxylic acids, esters and nitro groups; Soai reaction including reduction of carboxyl groups; Stille reactions including synthesis of biphenyl derivatives; Stork reaction including synthesis of substituted cyclohexanones; reductive amination including synthesis of quinolones; Suzuki reaction including synthesis of phenylacetic acid derivatives; and Wittig-Horner reactions including reactions of aldehydes, pheromones, and sulfanyl ketones.

References disclosing the synthesis of chemical libraries as well as the deconvolution of the individual compounds of those libraries onto individual solid phase supports, can be found in U.S. Patent Application No. 2009/0032592; Needels et al., (1993), *Proc. Natl. Acad. Sci. USA* 90: 10700-10704; and WO 97/15390.

3. Antibodies

In some aspects, the kinase inhibitor is an antibody. Antibodies are proteins that bind, preferably specifically, to a kinase as either a type I or type II inhibitor as described herein. Variants of antibodies can be made based on information known in the art, without substantially affecting the activity of antibody. For example, antibody variants can have at least one amino acid residue in the antibody molecule replaced by a different residue. For antibodies, the sites of greatest interest for substitutional mutagenesis generally include the hypervariable regions, but framework region (FR) alterations are also contemplated.

For antibodies, one type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In one embodiment, the Fc region variant may display altered neonatal Fc receptor (FcRn) binding affinity. Such variant Fc regions may comprise an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439 or 447 of the Fc region, wherein the numbering of the residues in the Fc region is that of the EU index as in Kabat. Fc region variants with reduced binding to an FcRn may comprise an amino acid modification at any one or more of amino acid positions 252, 253, 254, 255, 288, 309, 386, 388, 400, 415, 433, 435, 436, 439 or 447 of the Fc region, wherein the numbering of the residues in the Fc region is that of the EU index as in Kabat. The above-mentioned Fc region variants may, alternatively, display increased binding to FcRn and comprise an amino acid modification at any one or more of amino acid positions 238, 256, 265, 272, 286, 303, 305, 307, 311, 312, 317, 340, 356, 360, 362, 376, 378, 380, 382, 413, 424 or 434 of the Fc region, wherein the numbering of the residues in the Fc region is that of the EU index as in Kabat.

The Fc region variant with reduced binding to an Fc(R may comprise an amino acid modification at any one or more of amino acid positions 238, 239, 248, 249, 252, 254, 265, 268, 269, 270, 272, 278, 289, 292, 293, 294, 295, 296, 298, 301, 303, 322, 324, 327, 329, 333, 335, 338, 340, 373, 376, 382, 388, 389, 414, 416, 419, 434, 435, 437, 438 or 439 of the Fc region, wherein the numbering of the residues in the Fc region is that of the EU index as in Kabat.

For example, the Fc region variant may display reduced binding to an Fc(RI and comprise an amino acid modification at any one or more of amino acid positions 238, 265, 269, 270, 327 or 329 of the Fc region, wherein the numbering of the residues in the Fc region is that of the EU index as in Kabat.

The Fc region variant may display reduced binding to an Fc(RII and comprise an amino acid modification at any one or more of amino acid positions 238, 265, 269, 270, 292, 294, 295, 298, 303, 324, 327, 329, 333, 335, 338, 373, 376, 414, 416, 419, 435, 438 or 439 of the Fc region, wherein the numbering of the residues in the Fc region is that of the EU index as in Kabat.

The Fc region variant of interest may display reduced binding to an Fc(RIII and comprise an amino acid modification at one or more of amino acid positions 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 of the Fc region, wherein the numbering of the residues in the Fc region is that of the EU index as in Kabat.

Fc region variants with altered (i.e. improved or diminished) C1q binding and/or Complement Dependent Cytotoxicity (CDC) are described in International Patent Application No.: WO99/51642. Such variants may comprise an amino acid substitution at one or more of amino acid positions 270, 322, 326, 327, 329, 331, 333 or 334 of the Fc region. See, also, Duncan & Winter Nature 322:738-40 (1988); U.S. Pat. No. 5,648,260; U.S. Pat. No. 5,624,821; and International Patent Application No.: WO94/29351 concerning Fc region variants.

C. Second Harmonic-Active Labels

In some aspects of any of the methods provided herein, the kinase (such as any of the kinases described herein) is labeled with a second harmonic-active label. Second harmonic-active labels can be bound, either covalently or non-covalently, to a kinase in order to render the resulting kinase susceptible to second harmonic generation and amenable to study at an interface using a surface-selective technique. The labeled kinases may then be studied by surface-selective techniques such as second harmonic generation or sum-frequency generation. The exogenous labels can be pre-attached to the kinase, and any unbound or unreacted labels separated from the labeled entities before a measurement is made. In a one embodiment, the second harmonic-active label is attached to the kinase in vitro. The labeling of a kinase with a second harmonic-active label permits a direct, optical means of detecting kinase-kinase inhibitor binding reactions in cases where the binding reaction results in a change in the orientation or conformation of the label using a surface-selective nonlinear optical technique. Unlike detection with fluorescent labels, SHG-labels have the important advantage that only labeled kinases at an interface and with a net orientation contribute to the second harmonic signal; labeled kinases that fail to attach to surface contribute no signal. Therefore, the signal-to-noise ratio for detecting conformational changes in SHG-labeled kinase molecules upon the binding of a kinase inhibitor is invariably and consistently high.

In alternate aspects of the invention, at least two distinguishable second harmonic-active labels can be used. The orientation of the attached two or more distinguishable labels would then be chosen to facilitate well defined directions of the emanating coherent nonlinear light beam. The two or more distinguishable labels can be used in assays where multiple fundamental light beams at one or more frequencies, incident with one or more polarization directions relative to the sample, are used, with the resulting emanation of at least two nonlinear light beams. In one embodiment, the second harmonic-active label comprises a plurality of individual second harmonic-active labels which each have a nonlinear susceptibility and are bound together in a fixed and determinate orientation with respect to each other so as to increase the overall nonlinear susceptibility of the second harmonic-active label.

1. Second Harmonic-Active Dyes

In some aspects, the second harmonic-active label is a dye. The dye can be bound to the kinase by a specific interaction or by a non-specific interaction. The specific interaction may be a covalent bond or a hydrogen bond. In other embodiments, the second harmonic-active label is specific for an amine group, a lysine group, or for a sulfhydryl group in the primary amino acid sequence of the kinase to be detected. In another embodiment, the non-specific interaction comprises an electrostatic interaction. Examples of dyes appropriate for use as second harmonic-active labels in the methods disclosed herein include, without limitation, maleimide labels (such as PyMPO maleimide, which specifically labels proteins on cysteine residues), PyMPO-NHS (which specifically labels lysine residues), oxazole labels (such as PyMPO-succinimidyl ester which specifically labels amines), Badan, and Acrylodan. In some embodiments, the second harmonic-active dye labels an amino acid residue outside of the activation loop of the kinase. In another embodiment, the second harmonic-active dye labels an amino acid residue inside of the activation loop of the kinase.

In some aspects, a native amino acid residue in the primary amino acid sequence of the kinase can be mutated or substituted with another amino acid that is capable of binding to a second harmonic-active dye. In some embodiments, the native amino acid residue is located outside of the activation loop of the kinase. In other embodiments, the native amino acid residue is located inside of the activation loop of the kinase. As used herein, a "mutation" includes an amino acid residue deletion, an amino acid residue insertion, and/or an amino acid residue substitution of at least one amino acid residue in a defined primary amino acid sequence, such as a primary amino acid sequence of a kinase. An amino acid "substitution" means that at least one amino acid component of a defined primary amino acid sequence is replaced with another amino acid (for example, a cysteine residue or a lysine residue). Desirably, mutation or substitution of one or more amino acid residues (such as a conservative mutation or substitution) in a primary amino acid sequence does not result in substantial changes in the susceptibility of a kinase encoded by that amino acid sequence to undergo a conformational change upon binding to a known type I or type II kinase inhibitor or to an unknown candidate kinase inhibitor.

Methods for engineering a mutation or substitution into the primary amino acid sequence of a protein such as a kinase are well known in the art via standard techniques. The kinases described herein may include conservative substitutions. Conservative substitutions are shown in the "Table of Amino Acid Substitutions" below under the heading of "preferred substitutions."

| Amino Acid Substitutions | | |
|---|---|---|
| Original Residue | Exemplary Substitutions | Preferred Substitutions |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | Ala | ala |
| Ser (S) | Thr | thr |
| Thr (T) | Ser | ser |
| Trp (W) | tyr; phe | tyr |
| Tyr (Y) | trp; phe; thr; ser | phe |
| Val (V) | ile; leu; met; phe; ala; norleucine | leu |

Further information related to SHG dyes for labeling specific amino acids on a protein for use in SHG techniques can be found in Salafsky, 2001, *Chem Phys Letters*, 342: 485-491, the disclosure of which is incorporated by reference herein in its entirety.

2. Unnatural Amino Acids

In other aspects, the second harmonic-active label may be an unnatural amino acid (UAA). In contrast to conventional labels, UAA's offer a means of labeling proteins at both buried and exposed sites. Additionally, as innate components of the protein, they can report structural changes with more sensitivity and fidelity than labels (such as dyes) attached to amino acid functional groups (such as cysteines and amines). UAAs's possess hyperpolarizability for detecting proteins using a nonlinear technique such as second-harmonic generation. Therefore, these specific unnatural amino acids have also been referred to as SHAA's ("Second-Harmonic Amino-Acid"). Another advantage of using UAA's as probes for detection of changes in protein structural confirmation is that the detection can be carried out in vivo—that is, in live cells. For example, the methods described herein can be used to detect the conformational, change exhibited by a kinase in live cells in response to binding of a candidate kinase inhibitor. By using an oriented protein population of kinases relative to a surface a highly precise map of structure or conformational change in real space and real time can be built using kinases containing a UAA as part of its amino acid sequence. Desirably, substitution of one or more amino acid residues with a UAA in a primary amino acid sequence does not result in substantial changes in the susceptibility of a kinase encoded by that amino acid sequence to undergo a conformational change upon binding to a known type I or type II kinase inhibitor or to an unknown candidate kinase inhibitor.

Any hyperpolarizable UAA can be used as a second harmonic-active label to measure conformational changes in the structure of a kinase upon binding a candidate kinase inhibitor in any of the methods described herein. In some embodiments, the UAA is Aladan (Cohen et al., 2002, *Science*, 296:1700; Abbyad et al., 2007, *J. Phys. Chem.*, 111:8269, the disclosures of which are incorporated herein by reference in their entireties). In other embodiments, the UAA is Dansylalanine (Summerer et al., *Proc. Nat. Acad. Sci. U.S.A.*, 2006, 103(26): 9785-9789). In one embodiment, the unnatural amino acid is sum-frequency generation-active (SFG-active). As used herein, "sum-frequency generation-active" refers to an SH active label that possess a hyperpolarizability and is detectable by SFG. In other embodiments, the UAA is not hyperpolarizable, but possesses the appropriate chemical functional group or groups to permit it to bind to a second harmonic-active label dye, such as any of the dyes described above. In other embodiments, the UAA can include a probe with tailored vibrational properties for engineering into discreet sites within a protein to identify site-specific conformational changes by SFG. In some embodiments, probe moieties for inclusion into UAAs desirably are small enough so that they do not perturb native protein structure and can include, but are not limited to, NO, CN, SCN or $N_3$. In some embodiments, the probe moieties provide unique vibrational signatures in the spectral range of between about 1,900 and 2,300 $cm^{-1}$, which is well separated from intrinsic protein vibrations. In another embodiment, a UAA can be used to attach the kinase to a surface, such that a second harmonic-active label possesses a net orientation with respect to the surface.

Accordingly, in some aspects, structural changes in the conformation of a kinase (such as any of the kinases described herein) can be determined in real time and real space by measuring the tilt angle or absolute tilt angle of an unnatural amino acid label, or a series of such labels, engineered into the amino acid sequence in different mutants of the kinase protein. The probes can be incorporated at any site within the kinase or at its termini, or in any domain thereof. In some embodiments, the kinase can include a second-harmonic-active label that is chemically equipped to react covalently with a UAA. For example, if the UAA incorporated into a protein is Para-acetyl-phenylalanine (pAcF), the second-harmonic-active dye would have appropriate chemistry on it for bonding covalently to pAcF. In another embodiment, the incorporation of a SHAA in addition to a second UAA, the second UAA (which will in general not be second-harmonic-active) allows chemically orthogonal covalent coupling of the protein in an oriented manner to a surface derivatized with appropriate chemistry for reaction with the second UAA. With a highly oriented kinase protein sample that is SH-active (using the two UAA's), both the baseline SHG signal and the contrast (change in signal with conformational change) can be larger in comparison to kinases which do not utilize UAA's to produce SHG signals. In some embodiments, the UAA is located within the kinase activation loop. In another embodiment, the UAA is located outside of the kinase active loop.

In other aspects, use of one or more UAA's in the amino acid sequence of a kinase in any of the methods disclosed herein enables the determination of the actual conformational change the kinase undergoes upon candidate kinase-inhibitor-induced conformational change, by determining the tilt angle of one or more labels at one or more sites within the kinase as a function of time. The three dimensional structure of the kinase can be determined by making one or more mutants of a protein each containing a SHAA probe placed in a different location (i.e., the probe orientation relative to the surface in each mutant, and therefore the side-chain orientation, can be determined for the probe in each mutant and a model of the overall three dimensional protein structure can be built using this information). Information from steric hindrance methods, statistical methods, molecular dynamics, Ramachandran plots, or energy minimization methods known to those skilled in the art can be used to further aid in determining the structure given the measured probe tilt angles. A time-resolved measurement of the tilt angle of a probe produces a motion picture of a conformational change of a protein as it occurs in real time. Because of SHG's (and SFG's) virtually instantaneous response and sensitivity, spatial orientation of a particular probe (e.g., tilt angle or absolute tilt angle relative to a surface) can be measured in real time at almost any time scale of interest.

Further information related to the use of UAA's in SHG techniques can be found in U.S. Patent Application Publication No.: 2010/0068144, the disclosure of which is incorporated herein by reference in its entirety.

D. Interfaces

In some aspects of the methods disclosed herein, the kinase is bound to a solid surface or oriented with respect to an interface such that a second harmonic-active-label bound to the kinase has a net orientation. It is this net orientation than can change upon binding a candidate kinase inhibitor provided that the inhibitor induces a conformational change in the structure of the labeled kinase. In some embodiments, the interface can be made of silica, glass, silicon, polystyrene, nylon, plastic, a metal, semiconductor or insulator surface, or any surface to which biological components can adsorb or be attached. In different embodiments, the interface can be a vapor-liquid interface, a liquid-liquid interface, a liquid-solid, or a solid-solid interface. In one embodiment, the vapor-liquid interface is an air-water interface. In one embodiment, the liquid-liquid interface is an oil-water interface. In different embodiments, the liquid-solid interface is a water-glass interface or a benzene-$SiO_2$ interface.

In some aspects, the interface can also include biological cell and liposome surfaces. The attachment or immobilization can occur through a variety of techniques well known in the art. For example, with proteins, the surface can be derivatized with aldehyde silanes for coupling to amines on surfaces of biomolecules (MacBeath and Schreiber, 2000—relevant portions of which are incorporated by reference herein). BSA-NHS (BSA-N-hydroxysuccinimide) surfaces can also be used by first attaching a molecular layer of BSA to the surface and then activating it with N,N'-disuccinimidyl carbonate. The activated lysine, aspartate or glutamate residues on the BSA react with surface amines on the proteins.

Supported phospholipid bilayers can also be used, with or without membrane proteins or other membrane associated components as, for example, in Salafsky et al., *Biochemistry*, 1996—relevant portions of which are incorporated by reference herein by reference, "*Biomembranes*", Gennis, Springer-Verlag, Kalb et al., 1992, and Brian et al., 1984, relevant portions of which are incorporated herein by reference. Supported phospholipid bilayers are well known in the art and there are numerous techniques available for their fabrication, with or without associated membrane proteins. These supported bilayers typically must be submerged in aqueous solution to prevent their destruction when they become exposed to air.

If a solid surface is used (e.g., planar substrate, beads, etc.) it can also be derivatized via various chemical reactions to either reduce or enhance its net surface charge density to optimize the detection of kinase-candidate kinase inhibitor interactions. In other embodiments, the solid surface can be a glass surface, a plastic surface, a metal surface, a latex surface, a rubber surface, a ceramic surface, a polymeric surface, a polypropylene surface, a polyvinylidene difluoride surface, a polystyrene surface, or a polyethylene surface. The support on which the kinases are immobilized may be composed from a wide range of material, such as, but not limited to, biological, nonbiological, organic, inorganic, or a combination of any of these, existing as particles, strands, precipitates, gels, sheets, tubing, spheres, containers, capillaries, pads, slices, films, plates, or slides. The surface may have any convenient shape, such as, but not limited to, a disc, square, sphere, or circle. The surface can be preferably flat but may also take on a variety of alternative surface configurations. For example, the surface may contain raised or depressed regions on which a sample (such as a kinase) is located. The surface preferably forms a rigid support on which the sample can be formed. The surface is also chosen to provide appropriate light-absorbing characteristics. For example, the surface may be, without limitation, a polymerized Langmuir Blodgett film, functionalized glass, Si, Ge, GaAs, GaP, $SiO_2$ $SiN_4$, modified silicon, or any one of a wide variety of gels or polymers such as (poly)tetrafhioroefhylene, (poly)vinylidenedifluoride, polystyrene, polycarbonate, or combinations thereof. Other surface materials will be readily apparent to those of skill in the art. In one embodiment the substrate is flat glass or silica.

In some aspects, the surface can be etched using well known techniques to provide for desired surface features. For example, by way of the formation of trenches, v-grooves, mesa structures, or the like, the synthesis regions may be more closely placed within the focus point of impinging light. The surface may also be provided with reflective "mirror" structures for maximization of emission collected therefrom.

In another aspect of the present invention, oligo-polyethylene glycol (PEG) molecules can be used for immobilizing an affinity-tagged kinase to a surface for SHG or SFG detection. In some embodiments, the PEG can be SAT (PEG4) (N-Succinimidyl S-acetyl(thiotetraethylene glycol). A pegylated interface suitable for detecting SHG signals can be prepared by coating a suitable surface, such as any of the surfaces described above, with an oligo PEG solution. In one embodiment the surface can be glass. In another embodiment, the surface can be amino-terminated silane derivatized glass. Affinity tags are common in the art and may be, for example, a histidine tag (such as a $His_6$ tag (SEQ ID NO: 1)), a maltose binding protein tag, an HA tag, a biotin tag, a thiol tag, or a GST tag. In some embodiments, the affinity tag is a histidine having any of 1, 2, 3, 4, 5, 6, 7, 8, 9, 10, 11, 12, 13, 14, 15, 16, 17, 18, 19, 20, or more histidine residues (SEQ ID NO: 2). In one embodiment, the oligo-PEG molecules are modified with an agent that will bind to the affinity tag expressed on the kinase. The agent can be nickel, in the case of a histidine tag, or it can be a sugar (such as maltose), an antibody, or any other molecule known in the art that is capable of binding to an affinity tag.

IV. METHODS OF THE INVENTION

Provided herein are methods for classifying a candidate kinase inhibitor as a Type I or Type II kinase inhibitor based on the conformational change that the candidate kinase inhibitor induces in the structure of a kinase labeled with a second harmonic-active label. Further provided herein are methods for determining whether the conformational change induced in a kinase labeled with a second harmonic-active label upon binding to a generic drug is identical to the conformational change induced in the kinase upon binding to a branded drug, wherein the branded drug is a Type I or Type II kinase inhibitor.

A. Second Harmonic Generation

Second harmonic generation (SHG) is a nonlinear optical process, in which photons interacting with a nonlinear material are effectively "combined" to form new photons with twice the energy, and therefore twice the frequency and half the wavelength of the initial photons. It is a special case of sum frequency generation (SFG). Surface-selective nonlinear optical (SSNLO) techniques such as SHG allow the detection of interfacial molecules or particles in the presence of the bulk species. An intense laser beam (the fundamental) is directed on to the interface of some sample; if the interface is non-centrosymmetric, the sample is capable of generating nonlinear light, i.e. the harmonics of the fundamental. The fundamental or the second harmonic beams can easily be separated from each other, unlike the typical case in fluorescence techniques with excitation and emission light, which are separated more narrowly by the Stokes shift. Individual molecules or particles can be detected if they 1) are nonlinearly active (possess a hyperpolarizability) and 2) are near to the surface and through its influence (via chemical or electric forces) become non-randomly oriented. This net orientation and the intrinsic SHG-activity of the species are responsible for an SHG-allowed effect at the interface.

SHG has emerged as a sensitive technique to detect and study the conformational changes of biomolecules using SH-active probes (Salafsky, J. S. *Journal of Chemical Physics* 2006, 125, 074701; Salafsky, J. S. *Physical Chemistry Chemical Physics* 2007, 9, 5704). Labeled proteins that are adsorbed or covalently immobilized on surfaces produce an SHG signal, which is due to the average, net orientation of the nonlinear polarizability of the SHG label relative to the surface plane. Specifically, the SH intensity is given as $I_{SH}=G(\chi_s^{(2)})^2 I^2$, where $I_{SH}$ is the second-harmonic intensity, G is a constant that depends on the experimental geometry and wavelength, and I is the intensity of the fundamental beam. The nonlinear susceptibility, $\chi_s^{(2)}$, carries the details of the SH-active molecules on the surface via the equation:

$$\chi_s^{(2)}=N_s<\alpha^{(2)}>,$$

where $N_s$ is the surface density of the molecules, the brackets denote an orientational average, and $\alpha^{(2)}$ is their nonlinear polarizability, a quantum-mechanical property that determines the probability of producing a second-harmonic photon from two, incident photons of the fundamental beam. Measurements of $\chi_s^{(2)}$ provide information about the orientation of a molecule on the surface. For example, when $\alpha^{(2)}$ is dominated by a single element $\zeta\zeta\zeta^{(2)}$ along the molecular axis $\zeta$ and the azimuthal distribution of the molecules are random in the plane of the surface, the only elements of $\chi_s^{(2)}$ that do not vanish are:

$$\chi_{s\perp\perp\perp}^{(2)}=N_s<\cos^3\theta>\alpha_{\zeta\zeta\zeta}^{(2)}$$

$$\chi_{s\perp\|\|}^{(2)}=\chi_{s\|\perp\|}^{(2)}=\chi_{s\|\|\perp}^{(2)}=\tfrac{1}{2}N_s<\cos\theta\sin^2\theta>\alpha_{\zeta\zeta\zeta}^{(2)}$$

where $\theta$ is the polar angle between $\zeta$ and the surface normal, and the subindices $\perp$ and $\|$ refer to the directions perpendicular and parallel to the surface, respectively (Heinz, T. F., et al., *Physical Review A* 1983, 28, 1983).

The SH light is coherent and directional, so collection and isolation of the SH beam is simplified, and because the fundamental and the second-harmonic are well separated spectrally, cross-talk, which can plague fluorescence measurements, is non-existent with SHG. Photodegradation of the probe occurs relatively slowly via two-photon-induced absorption, allowing measurements over relatively long timescales. The trade-off with SHG is signal strength—it is orders of magnitude weaker than fluorescence. However, only SH-active molecules immobilized on the surface contribute second harmonic light since randomly diffusing molecules near the surface produce no signal; their orientational average, from Equation 1, is zero. Therefore, SHG is intrinsically equipped to discriminate between surface-bound and free molecules. The SH signal reports on the orientational average of the probes, and thus changes due to conformational change.

The apparatus for detection of kinase-candidate kinase inhibitor interactions and their effects on kinase conformational structure can assume a variety of configurations. In its most simple form, the apparatus will comprise the following: i) a source of the fundamental light; ii) a substrate with surface-attached probes (such as an SHG-labeled kinase); and iii) a detector for measuring the intensity of the second harmonic or other nonlinear optical beams. More elaborate versions of the apparatus will employ, for example: a monochromator (for wavelength selection), a pass-filter, color filter, interference or other spectral filter (for wavelength selection or to separate the fundamental(s) from the higher harmonics), one or more polarizing optics, one or more mirrors or lenses for directing and focusing the beams, computer control, or software.

The mode of delivering or generating the nonlinear optical light (e.g., SHG) can be based on one or more of the following means: TIR (Total internal reflection), Fiber optics (with or without attached beads), Transmission (fundamental passes through the sample), Reflection (fundamental is reflected from the sample), scanning imaging (allows one to scan a sample), confocal imaging or scanning, resonance cavity for power build-up, multiple-pass set-up.

Measured information can take the form of a vector which can include one or more of the following parameters: intensity of light (typically converted to a photovoltage by a PMT or photodiode), wavelength of light (determined with a monochromator and/or filters), time, or position. Two general configurations of the apparatus are: image scanning (imaging of a substrate—intensity, wavelength, etc. as a function of x,y coordinate) and spectroscopic (measurement of the intensity, wavelength, etc. for some planar surface or for a suspension of cells, liposomes or other particles).

The fundamental beam can be delivered to the sample in a variety of ways (See, e.g., U.S. Patent Application Publication No.: 2002/0094528, the disclosure of which is incorporated by reference herein in its entirety). It is understood that in sum- or difference-frequency configurations, the fundamental beams will be comprised of two or more beams, and will generate, at the interfaces, the difference or sum frequency beams.

According to another aspect, charge-coupled detectors (CCD) array detectors can be used when information is desired as a function of substrate location (x,y). CCDs comprise an array of pixels (i.e., photodiodes), each pixel of which can independently measuring light impinging on it. For a given apparatus geometry, nonlinear light arising from a particular substrate location (x,y) can be determined by measuring the intensity of nonlinear light impinging on a CCD location (Q,R) some distance from the substrate—this can be determined because of the coherent, collimated (and generally co-propagating with the fundamental) nonlinear optical beam) compared with the spontaneous, stochastic and multidirectional nature of fluorescence emission. With a CCD array, one or more array elements {Q,R} in the detector will map to specific regions of a substrate surface, allowing for easy determination of information as a function of substrate location (x,y). Photodiode detector and photomultiplier tubes (PMTs), avalanche photodiodes, phototransistors, vacuum photodiodes or other detectors known in the art for converting incident light to an electrical signal (i.e., current, voltage, etc.) can also be used to detect light intensities. For CCD detector, the CCD communicates with and is controlled by a data acquisition board installed in the apparatus computer. The data acquisition board can be of the type that is well known in the art such as a CIO-DAS 16/Jr manufactured by Computer Boards Inc. The data acquisition board and CCD subsystem, for example, can operate in the following manner. The data acquisition board controls the CCD integration period by sending a clock signal to the CCD subsystem. In one embodiment, the CCD subsystem sets the CCD intregration period at 4096 clock periods. By changing the clock rate, the actual time in which the CCD integrates data can be manipulated. During an integration period, each photodiode accumulates a charge proportional to the amount of light that reaches it. Upon termination of the integration period, the charge is transferred to the CCD's shift registers and a new integration period commences. The shift registers store the charges as voltages which represent the light pattern incident on the CCD array. The voltages are then transmitted at the clock rate to the data acquisition board, where they are digitized and stored in the computer's memory. In this manner, a strip of the sample is imaged during each integration period. Thereafter, a subsequent row is integrated until the sample is completely scanned.

In one aspect, the detector of the SH light can be a photomultiplier tube operated in single-photon counting mode. Photocurrent pulses can be voltage converted, amplified, subjected to discrimination using a Model SR445 Fast Preamplifier and Model SR 400 Discriminator (supplied by Stanford Research Systems, Inc.) and then sent to a counter. Photon counter gating and galvo control through a DAC output can be synchronized using a digital delay/pulse generator. Communication with a PC computer can be accomplished according to multiple methods as known to one skilled in the art, including but not limited to, using a parallel register, a CAMAC controller card, and a PC adapter card.

In an alternative aspect, a bandpass, notch, or color filter is placed in either or all of the beam paths (e.g. fundamental, second harmonic, etc.) allowing, for example, for a wider spectral bandwidth or more light throughput. In one embodiment, an interference, notch-pass, bandpass, reflecting, or absorbent filter can be used in place of the filters in the figures in order to either pass or block the fundamental or nonlinear optical beams.

In some aspects of the methods provided herein, data recorded by the detector may be recorded on a fixed or data storage medium that is accessible via a system for reading the storage medium. For example, a system for reading a data storage medium may include a computer including a central processing unit ("CPU"), a working memory which may be, e.g., RAM (random access memory) or "core" memory, mass storage memory (such as one or more disk drives or CD-ROM drives), one or more display devices (e.g., cathode-ray tube ("CRT") displays, light emitting diode ("LED") displays, liquid crystal displays ("LCDs"), electroluminescent displays, vacuum fluorescent displays, field emission displays ("FEDs"), plasma displays, projection panels, etc.), one or more user input devices (e.g., keyboards, microphones, mice, touch screens, etc.), one or more input lines, and one or more output lines, all of which are interconnected by a conventional bidirectional system bus. The system may be a stand-alone computer, or may be networked (e.g., through local area networks, wide area networks, intranets, extranets, or the internet) to other systems (e.g., computers, hosts, servers, etc.). The system may also include additional computer controlled devices such as consumer electronics and appliances.

Input hardware may be coupled to the computer by input lines and may be implemented in a variety of ways. Machine-readable data of this invention may be inputted via the use of a modem or modems connected by a telephone line or dedicated data line. Alternatively or additionally, the input hardware may include CD-ROM drives or disk drives. In conjunction with a display terminal, a keyboard may also be used as an input device.

Output hardware may be coupled to the computer by output lines and may similarly be implemented by conventional devices. By way of example, the output hardware may include a display device for displaying a graphical representation of an active site of this invention using a program such as QUANTA. Output hardware might also include a printer, so that hard copy output may be produced, or a disk drive, to store system output for later use.

Machine-readable storage devices useful in the present invention include, but are not limited to, magnetic devices, electrical devices, optical devices, and combinations thereof. Examples of such data storage devices include, but are not limited to, hard disk devices, CD devices, digital video disk devices, floppy disk devices, removable hard disk devices, magneto-optic disk devices, magnetic tape devices, flash memory devices, bubble memory devices, holographic storage devices, and any other mass storage peripheral device. It should be understood that these storage devices include necessary hardware (e.g., drives, controllers, power supplies, etc.) as well as any necessary media (e.g., disks, flash cards, etc.) to enable the storage of data.

A person having skill in the art will appreciate that any other method or technique to communicate or store data is also contemplated for providing real time data of kinase conformational changes upon binding a candidate kinase inhibitor in a machine readable format.

B. Methods for Classifying an Unknown Candidate Kinase Inhibitor

Provided herein are methods for classifying a kinase inhibitor as a type I or type II kinase inhibitor based on the conformational change that the candidate kinase inhibitor induces in the structure of a kinase labeled with a second harmonic-active label. In some embodiments, a kinase is contacted with a type I or type H kinase inhibitor, such that the label has a net orientation at an interface wherein the kinase specifically interacts with the type I or type II kinase inhibitor and an interaction between the kinase and the type I or type II kinase inhibitor can be detected by measuring a signal or signal change generated by the second harmonic-active label using a surface-selective technique. The signal or signal change indicates a conformational change in the structure of the kinase that is specific for the type I or type H kinase inhibitor. This method may additionally be used to classify an unknown candidate kinase inhibitor as belonging to either the type I or type II class by contacting the kinase with the unknown candidate kinase inhibitor, such that the label has a net orientation at an interface and detecting an interaction between the kinase and the unknown candidate kinase inhibitor by measuring a signal or signal change generated by the second harmonic-active label using a surface-selective technique. The signal or signal change indicates a conformational change in the structure of the kinase produced by the interaction between the kinase and the unknown candidate kinase inhibitor. This characteristic signal or signal change can be compared to the signal or signal change produced in response to the interaction between the kinase and the type I or type II kinase inhibitor to classify the unknown candidate kinase inhibitor as belonging to the type I or type II kinase inhibitor class based on the conformational change it induces in the structure of the kinase. For example, if an unknown candidate kinase inhibitor produces a signal or signal change that is identical to a signal or signal change produced by a type I or II kinase inhibitor, the unknown kinase inhibitor can be classified as either belonging to the type I or type II class.

In some aspects, the kinases for use in the methods described herein do not have any known type I or type II kinase inhibitors. The catalytic subunits of protein kinases across the kinome are highly conserved. For example, eukaryotic protein kinases share a conserved catalytic core common with both serine/threonine and tyrosine protein kinases. The N-terminal extremity of the catalytic domain of most kinases share a glycine-rich stretch of residues in the vicinity of a lysine residue, which has been shown to be involved in ATP binding. Furthermore, the central part of the catalytic domain contains a conserved aspartic acid residue which is also important for the catalytic activity of most kinases (Knighton et al., 1994, *Science*, 253 (5018): 407-14). Accordingly, due to the structurally conserved homology of kinases across the kinome, the methods disclosed herein can be used to classify an unknown kinase inhibitor as either a type I or type II kinase inhibitor upon binding to a kinase with no other known kinase inhibitors.

As such, in some aspects, the kinase used in the methods described herein has no known type I or type II inhibitors. In some embodiments, the method includes classifying a kinase inhibitor as a type I or type II kinase inhibitor based on the conformational change that the candidate kinase inhibitor induces in the structure of a kinase labeled with a second harmonic-active label, wherein the kinase has no known other known type I or type II inhibitors. In some embodiments, the SHG signal or signal change produced by a known type I or type II kinase inhibitor binding to a kinase known to be inhibited by that type I or type II inhibitor can be compared to the signal or signal change produced in response to the interaction between an unknown candidate kinase inhibitor and a kinase that has no known type I or type II inhibitors to classify the unknown candidate kinase inhibitor as belonging to the type I or type II kinase inhibitor class based on the conformational change it induces in the structure of the kinase that has no known type I or type II inhibitors. For example, if an unknown candidate kinase inhibitor produces an SHG signal or signal change in a kinase with no known type I or type II inhibitors that has a similar profile to a signal or signal change produced by a type I or II kinase inhibitor binding to a kinase known to be inhibited by that type I or type II kinase inhibitor, the unknown kinase inhibitor can be classified as either belonging to the type I or type II class based on the comparison.

In some aspects, the type I or type II kinase inhibitor are known type I or type II kinase inhibitors, such as any of the type I or type II kinase inhibitors discussed above. In some embodiments, the known type I inhibitor can be sunitinib, PIK-39, dasatinib, or SB-431542. In other embodiments, the known type II inhibitor can be sorafenib, imatinib, doramapimod, AAL993, diaryl urea, indole amide, anilinoquinazoline, linifanib, AST-487, and 4-aminopyrimidinoquinazoline. In one embodiment, the known type II inhibitor can be imatinib.

In some aspects, the unknown candidate kinase inhibitor can be a small molecule chemical compound, a non-antibody polypeptide, or an antibody (for example, a humanized antibody, a monoclonal antibody, or a fragment of an antibody, such as a Fab).

In some aspects, the kinase can be labeled with a second harmonic (SH) active label, such as any of the labels described above. In one embodiment, the kinase is labeled with a second harmonic-active label on one or more of the kinase's amino acid residues and attached to a surface or oriented at an interface, such as any of the surfaces or interfaces described herein, so that the SH active label possesses a net orientation with respect to the interface. The labeled amino acid can include, but are not limited to, cysteine residues, lysine residues, or amines. In other embodiments, the kinase is labeled with an unnatural amino acid, such as, but not limited to Aladan or Dansylalanine. In another embodiment, the unnatural amino acid is sum-frequency generation-active (SFG-active). In some embodiments, a UAA comprising a unique probe with tailored vibrational properties can be engineered into a protein at a discrete site (such as a kinase activation loop or a region outside of a kinase activation loop) to identify site-specific conformational changes by SFG. Probe moieties can include, but are not limited to, NO, CN, SCN or $N_3$. In some embodiments, the probe moieties provide unique vibrational signatures in the spectral range between about 1,900 and 2,300 $cm^{-1}$. In some embodiments, a native amino acid residue in the kinase is labeled with the second harmonic active label. In other embodiments, the labeled amino acid residue can be a mutated or substituted amino acid residue (such as a conservatively mutated or a conservatively substituted amino acid residue) engineered into the primary amino acid sequence of the kinase. In some embodiments, the label is associated with an amino acid residue within the activation loop of the kinase. In other embodiments, the label is associated with an amino acid residue outside of the activation loop of the kinase.

In other aspects, the kinase can be bound to a surface or at an interface, such as any of the surfaces or interfaces described above. In some embodiments, the kinase includes an affinity tag (such as, but not limited to, a polyhistidine tag, for example $His_6$ (SEQ ID NO: 1)) for immobilizing it onto the surface. In another embodiment, the surface is coated with nickel-oligo-PEG molecules for immobilizing a $His_6$-tagged kinase ("$His_6$" disclosed as SEQ ID NO: 1) to the surface for SHG or SFG detection.

In some aspects, binding of a known type I or type II kinase inhibitor or an unknown candidate kinase inhibitor to a SH active labeled kinase can induce a conformational change in the structure of the kinase. In some embodiments, this conformational change can cause the net orientation of the SH active label to change relative to the interface. In some embodiments, the net orientation of the SH active label changes any of about 1°, 2°, 3°, 4°, 5°, 6°, 7°, 8°, 9°, 10°, or more relative to the interface upon binding to a known type I or type II kinase inhibitor or an unknown candidate kinase inhibitor. In one embodiment, this change is detected and recorded in real time.

C. Methods for Comparing Conformational Changes Induced by Generic and Branded Drugs in the Structure of a Kinase A "generic drug" is a term used to describe officially-approved subsequent versions of innovator biopharmaceutical products made by a different sponsor following patent and exclusivity expiry on the innovator product. Generic drugs can include, but are not limited to, biologics and small molecule chemical compounds. "Biologics," refer to medicinal products such as recombinant therapeutic proteins, antibodies, or living cells that are used to treat diseases. For example, biologics are created by biological processes, rather than being chemically synthesized. A generic biologic, is known as a "biosimilar." Biologics can be composed of sugars, proteins, or nucleic acids or complex combinations of these substances, or may be living entities such as cells and tissues. Biologics are isolated from a variety of natural sources—human, animal, or microorganism—and may be produced by biotechnological methods and other technologies. Gene-based and cellular biologics, for example, often are at the forefront of biomedical research, and may be used to treat a variety of medical conditions for which no other treatments are available.

While having access to the commercialized innovator product, the manufacturers of biosimilars do not have access to the originator's molecular clone and original cell bank, nor to the exact fermentation and purification process, nor to the active drug substance used in order to produce the biologic therapeutic drug. Because no two cell lines, developed independently, can be considered identical, biotechnologically-produced medicines cannot be fully copied. The European Medicines Agency, EMEA, has recognized that, while it is possible that biosimilars can be similar to the original product, they are not exactly the same (see, e.g., EMEA guideline on similar biological medicinal products, October, 2005, www.emea.europa.eu/docs/en_GB/document_library/Scientific_guideline/2009/09/WC50000 3517.pdf). Small distinctions in the cell line, in the manufacturing process or in the surrounding environment can make a major difference in side effects observed during treatment, i.e. two similar biologics can trigger very different immunogenic response. Therefore, and unlike chemical pharmaceuticals, substitution between biologics, can have clinical consequences that create putative health concerns.

Because differences in impurities and/or breakdown products produced during generic drug (such as biosimilar or small molecule chemical compound) manufacture can have serious health implications, this has created a concern that copies of generic drugs might perform differently than the original branded version of the product. For example, and as a consequence, only a few subsequent versions of biologics have been authorized in the United States by the U.S. Food and Drug Administration (FDA) through the relatively simplified procedures allowed for small molecule generics, namely Menotropins (January 1997) and Enoxaparin (July 2010), and a further eight biologics through the FDA's 505(b)(2) drug approval pathway.

In most countries, biosimilars are subject to an approval process which requires substantial additional scientific and medical data compared to what is required for regulatory approval of generic small molecule chemical compounds, although not as comprehensive as what is required for the original innovator product. Introduction of biosimilars also requires a specifically designed pharmacovigilance plan. In order to be released to the public, biosimilars must be shown to be as close to identical to the parent biological product based on data compiled through clinical, animal and analytical studies. The results must demonstrate that they produce the same clinical results and are interchangeable with the referenced FDA licensed biological product already on the market. With respect to kinase inhibitors, whether a generic drug (such as, but not limited to, a biosimilar or a small molecule chemical compounds) elicits the same effect on a kinase as a branded drug is also a concern for government regulatory bodies. Because of the difficulties associated with determining conformational changes in the structure of a kinase that occur upon binding to a generic kinase inhibitor in comparison to a branded type I or type II kinase inhibitor, there is a great need for a fast and non-labor intensive method for determining whether the conformational changes elicited by the two drugs are identical Accordingly, provided herein are methods for comparing the conformational changes induced by a generic drug and a branded drug in the structure of a kinase labeled with a second harmonic-active label, where the branded drug is a type I or type II kinase inhibitor. In some embodiments, a kinase can be contacted with the branded drug such that the label has a net orientation at an interface and an interaction between the kinase and the branded drug can be detected by measuring a signal or signal change generated by the second harmonic-active label using a surface-selective technique. This signal or signal change indicates a conformational change in the structure of the kinase that is specific for the branded drug. Following this, the kinase can be contacted with the generic drug, such that the label has a net orientation at an interface and an interaction between the kinase and the generic drug can be detected by measuring a signal or signal change generated by the harmonic-active label using a surface-selective technique. This signal or signal change indicates a conformational change in the structure of the kinase that is specific for the generic drug. The signal or signal change produced by the binding of the branded drug to the kinase can then be compared to the signal or signal change produced by the binding of the generic drug to the kinase to determine whether the conformational change induced in the kinase by the generic drug is identical to the change induced by the branded drug.

In some aspects, the branded drug can be a type I or type II inhibitor. However, whether or not the branded drug is classified as such is not required. In some embodiments, the branded drug can first be classified as a type I or type II inhibitor, according to any of the methods disclosed herein, and then compared to the generic drug to determine whether the conformational change induced in the kinase by the generic drug is identical to the change induced by the branded drug. In some embodiments, the branded drug is a type II inhibitor, such as any of the type II inhibitors disclosed herein.

In some aspects, the methods are applicable to branded small molecule chemical compound kinase inhibitors. In some aspects, the branded small molecule chemical compound kinase inhibitor can be a type I or type II inhibitor. However, whether or not the branded small molecule kinase inhibitor is classified as such is not required. In some embodiments, the branded small molecule kinase inhibitor can first be classified as a type I or type II inhibitor, according to any of the methods disclosed herein, and then compared to a generic small molecule kinase inhibitor to determine whether the conformational change induced in the kinase by the generic small molecule kinase inhibitor is identical to the change induced by the branded drug. In some embodiments, the branded small molecule chemical compound kinase inhibitor is a type II inhibitor, such as any of the type II inhibitors disclosed herein. In other embodiments, the type II inhibitor is imatinib (Gleevec).

Similarly, in other aspects, the methods are applicable to branded biologics-based kinase inhibitors. In some aspects, the branded biologics-based kinase inhibitor can be a type I or type II inhibitor. However, whether or not the branded biologics-based kinase inhibitor is classified as such is not required. In some embodiments, the branded biologics-based kinase inhibitor can first be classified as a type I or type II inhibitor, according to any of the methods disclosed herein, and then compared to a biosimilar kinase inhibitor to determine whether the conformational change induced in the kinase by the biosimilar kinase inhibitor is identical to the change induced by the branded biologics-based drug.

In some aspects, the kinase can be labeled with a second harmonic (SH) active label, such as any of the labels described above. In one embodiment, the kinase is labeled with a second harmonic-active label on one or more of the kinase's amino acid residues and attached to a surface or oriented at an interface, such as any of the surfaces or interfaces described herein, so that the SH active label possesses a net orientation with respect to the interface. The labeled amino acid can include, but are not limited to, cysteine residues, lysine residues, or amines. In other embodiments, the kinase is labeled with an unnatural amino acid, such as, but not limited to Aladan. In some embodiments, a native amino acid residue in the kinase is labeled with the second harmonic active label. In other embodiments, the labeled amino acid residue can be a mutated or substituted amino acid residue (such as a conservatively mutated or a conservatively substituted amino acid residue) engineered into the primary amino acid sequence of the kinase. In some embodiments, the label is associated with an amino acid residue within the activation loop of the kinase. In other embodiments, the label is associated with an amino acid residue outside of the activation loop of the kinase.

In other aspects, the kinase can be bound to a surface or at an interface, such as any of the surfaces or interfaces described above. In some embodiments, the kinase includes an affinity tag (such as, but not limited to, a polyhistidine tag, for example $His_6$ (SEQ ID NO: 1)) for immobilizing it onto the surface. In another embodiment, the surface is coated with nickel-oligo-PEG molecules for immobilizing a $His_6$-tagged kinase ("$His_6$" disclosed as SEQ ID NO: 1) to the surface for SHG or SFG detection.

In some aspects, binding of a known or unknown type I or type II kinase inhibitor (such as a branded kinase inhibitor) or a generic kinase inhibitor (such as, but not limited to, a biosimilar or generic small molecule kinase inhibitor) to a SH active labeled kinase can induce a conformational change in the structure of the kinase. In some embodiments, this conformational change can cause the net orientation of the SH active label to change relative to the interface. In some embodiments, the net orientation of the SH active label changes any of about 1°, 2°, 3°, 4°, 5°, 6°, 7°, 8°, 9°, 10°, or more relative to the interface upon binding to a known or unknown type I or type II kinase inhibitor (such as a branded kinase inhibitor) or a generic kinase inhibitor. In one embodiment, this change is detected and recorded in real time.

V. SYSTEMS

Provided herein are systems for determining the conformational change induced in a kinase by the binding of a type I or type II kinase inhibitor. The system can have a substrate with a surface-attached SHG-labeled kinase and an apparatus for generating and detecting a signal or signal change produced by the SHG-label upon the binding of a type I or type II kinase inhibitor to the kinase. The signal or signal change can be analyzed by the apparatus to produce a readout which is characteristic of the conformational change in the structure of the kinase that is induced by the kinase inhibitor.

In some embodiments, the system can have one or more of the following components: a source of a fundamental light, a substrate with a surface-attached SHG-labeled kinase, and a detector for measuring the intensity of the second harmonic or other nonlinear optical beams. The system can also employ, for example: a monochromator (for wavelength selection), a pass-filter, color filter, interference or other spectral filter (for wavelength selection or to separate the fundamental(s) from the higher harmonics), one or more polarizing optics, one or more mirrors or lenses for directing and focusing the beams, computer control, or software analyzing the detection signals correlated to the specific SHG-labeled kinase or kinase inhibitor.

VI. KITS

Also provided herein are kits for use in performing any of the methods disclosed herein. The kit may include one or more of 1) any of the surfaces or interfaces described herein for immobilizing or attaching a kinase, 2) any of the SH-active labels described herein for labeling a kinase, 3) any of the apparatuses for eliciting an second harmonic signal or signal change described herein, and/or 4) any of the apparatuses for analyzing the signal or signal change, wherein the analyzed signal indicates whether a kinase inhibitor is a type I or type II kinase inhibitor.

EXEMPLARY EMBODIMENTS

Surface-selective techniques such as second-harmonic generation (SHG) have recently been applied to the study of proteins at interfaces and protein conformational change by the use of second-harmonic-active labels[1-3] which are attached to the surface of the protein. Second-harmonic-active labels contain moieties which are hyperpolarizable and thus detectable by SHG or sum-frequency generation (SFG). Methods for detecting proteins by SHG have been disclosed wherein the protein is detected by incorporating an SHG-active probe or label into it. A schematic of the detection process for detecting conformational changes is shown in FIG. 1. The present invention particularly concerns kinase proteins, which are important drug targets for cancers and other diseases. As described above, conformation specific drugs targeted to kinases are of high interest but identifying them with respect to whether they belong to the type I or type II class of kinase inhibitors often requires X-ray crystallography or NMR, which are labor and time-intensive techniques. A high-throughput, real time method for identifying the conformational changes in the structure of a kinase produced by candidate kinase inhibitor ligands or potential drugs would be desirable. Prior art discloses the method of labeling adenylate kinase with an amine-specific or cysteine-specific SHG-active probe and detecting conformational changes (Salafsky, *Physical Chemistry Chemical Physics,* 2007, 9, 5704-5711). This kinase undergoes very large conformational changes upon binding ligands. However, it was not evident whether the same approach would work for a non-nucleotide kinase (e.g., tyrosine or serine/threonine kinases) or for a kinase in which the conformational changes occurred mainly around the ligand binding pocket.

Figure 5:
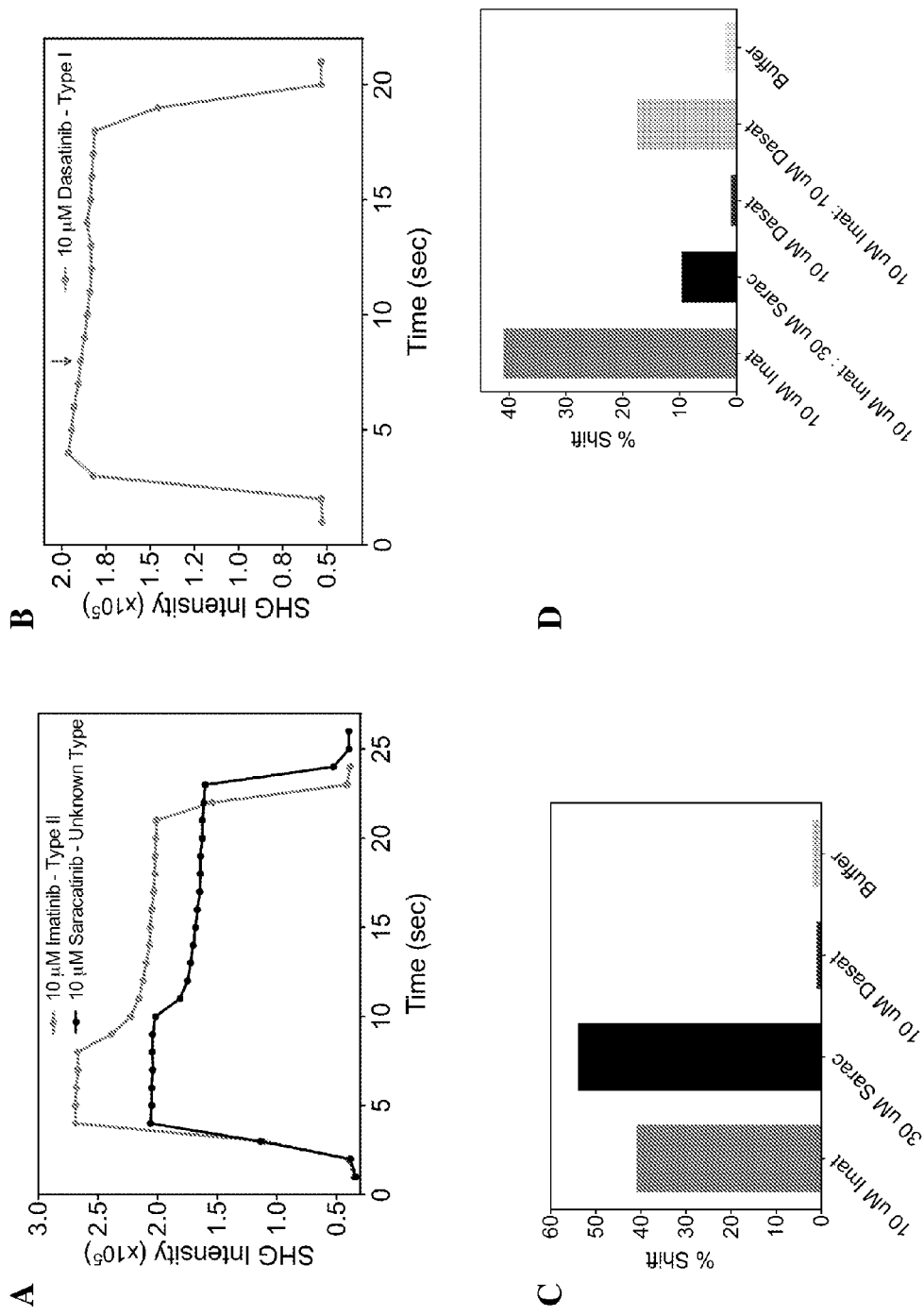
FIG. 5 depcicts specific identification of different types of kinase inhibitors by SH assays. Kinetic data are recorded for Abl kinase treated with the type II inhibitor, imatinib (A; grey curve), the uncharacterized inhibitor, saracatinib (A; black curve), and the type I inhibitor, dasatinib (B) Significant differences between responses to the known type I and II inhibitors are observed. Responses for the three different inhibitor compounds were quantified and compared to buffer controls (C) confirming that the type I inhibitor did not generate a significant response. However, in experiments designed to demonstrate response specificity (D), imatinib responses are blocked by pre-incubation with both type I and type II compounds.

One aspect of the present invention discloses detecting specific conformational changes of a kinase, Abl kinase, upon binding to different drugs. A second aspect of the present invention discloses labeling kinase at one or more sites outside the activation loop using native or engineered residues for detection by SHG and discrimination of conformation-specific ligands. A third aspect of the present invention is the use of oligo-PEG molecules for immobilizing a His-tagged kinase to a surface for SHG or SFG detection. A fourth aspect of the invention is labeling a native residue of a non-nucleotide kinase to detect conformational changes. A fifth aspect of the invention is obtaining different 'signatures' (SHG responses) upon binding different known ligands to any protein, classifying these, and comparing these to the signatures produced by unknown ligands to determine which binding class of the unknown ligands. The signatures of unknown ligands can then be used to deduce the binding type (conformation produced) by comparing them to those of standard (known) drugs. In the present disclosure, this aspect is illustrated by obtaining SHG signatures of conformational changes produced by known drugs imatinib and dasatinib, whose co-structures with Abl kinase have been determined by NMR and X-ray crystallography and comparing these to the response upon binding saracatinib. The binding mode of saracatinib is then deduced by comparing its SHG signature to those produced by these standard drugs. As is shown in FIG. 5A, saracatinib produces a similar SHG response upon binding Abl kinase to imatinib and is thus identified by SHG as a Type II Abl kinase inhibitor (and dasatinib in this assay produces no response). Another aspect of the present invention is to assay the function of non-brand biotherapeutics (e.g., biosimilars) using the SHG responses of conformational change, i.e. to determine whether the non-brand biotherapeutics (i.e., biosimilars) are functioning in the same way as brand biotherapeutics. For example, one or more known ligands is exposed to a brand biotherapeutic to determine SHG signatures produced upon binding of the ligands. These known ligands are then exposed to a generic (putative biosimilar therapeutic) and the SHG responses classified. Whether a biosimilar therapeutic is indeed similar to a brand biotherapeutic can then be deduced from the SHG functional responses 'signatures' of binding of these known ligands.

For enzymes such as tyrosine kinases[1,2,6,14-21], important conformational changes occur in loop regions, such as in the activation loop upon binding ligands or drugs. The loop regions are well known to those skilled in the art of determining or using the structures of the proteins. Moreover, catalytic function of a kinase requires an active conformation of the loop. As the active structures of kinase proteins across the kinome are highly similar, drugs that target the active form of a kinase often are non-selective, reacting 'off-target' with other kinases. Inhibitors that stabilize the proteins in inactive structures could be more selective because these structures are less homologous across the kinome. Loop regions that are well known in the art include catalytic loops, WPD loops, PTP loops, recognition loops and activation loops. Type II drugs such as Gleevec targeted to Abl kinase stabilize the activation loop in an inactive conformation and are highly efficacious and selective. Type I drugs such as dasatinib stabilize the active conformation and are typically less selective. It is desirable to have a high-throughput real time assay for distinguishing between type I and type II drugs for primary screening or lead validation, among other applications. An example of labeling Abl kinase for detection by SHG is given below. The inhibitor saracatinib which is known to be a type II inhibitor for c-Src is identified by its SHG response to be a type II binder to Abl kinase as well.

The invention can be further understood by reference to the following examples, which are provided by way of illustration and are not meant to be limiting.

EXAMPLES

Kinases are a major class of drug targets with at least 30 distinct kinase targets currently in clinical trials. Most kinase drugs, known as type I inhibitors, bind to the kinase ATP binding site and work by mimicking and directly competing with ATP to stabilize the kinase activation loop into an active confirmation. Type II inhibitors, on the other hand, cause the activation loop of the kinase to shift into an inactive conformation. The identification of type II inhibitors is difficult, due to the fact that determination of the site of candidate inhibitor binding to a kinase typically requires X-ray crystallography to discern. In this example, second harmonic generation (SHG) detection is used to classify a kinase inhibitor as either belonging to the type I or type II class by measuring the conformational changes associated with inhibitor binding to the kinase.

Materials and Methods

The following Materials and Methods are used in the examples described above.

Kinase Production and Labeling

Abl kinase KD with a N-terminal 6×His tag (SEQ ID NO: 1) is constructed, expressed and purified as described in the literature.[22-24] The protein is dialyzed in labeling buffer (0.1 M Tris buffer pH 8.0, 20 mM NaCl, 5 mM TCEP, 5% glycerol) by standard procedures. The protein concentration should be 2-5 mg/mL for labeling. Lower concentrations are acceptable but labeling time may need to be adjusted accordingly. Concentrating the protein by use of a Centricon may be necessary to raise the protein to this level of concentration.

The concentrated protein (2-5 mg/mL) is mixed with PyMPO maleimide (Invitrogen) at a molar ratio of 1:12. Maleimide probes are highly specific for cysteines. The DMSO concentration in the labeling reaction is limited to about 3% or less. The labeling reaction is then transferred to a clean conical glass labeling vial with a stir vane and the reaction placed inside foil wrap on a stir plate for 1 hour at room temperature with gentle stirring. The labeled protein is column purified using Zeba spin columns using manufacturer's published protocols in an aliquot of stacking buffer of Measurement/Loading buffer (0.1M Tris, buffer pH 8.0 20 mM NaCl). The protein:dye stoichiometry is determined spectrophotometrically to be 1:2 in this case. Mass spectrometry confirms that the probe labeled 2 cysteines in the kinase.

Immobilization of the Kinase onto a Pegylated Surface

A slide with an oligo-PEG derivatization is prepared as follows: clean slide-staining vessels and dry in vacuum oven at 75° C./20 inches Hg, let cool to room temp. Add enough SAT(PEG4) (N-Succinimidyl S-acetyl(thiotetraethylene glycol; Pierce) solution in staining vessels to cover entire slides (~50 mL). Place Ultrastick slides (amino-terminated silane derivatized slides; Thermo) in a staining rack and submerge in a staining vessel. Incubate the slides in a hood at room temperature, stirring for 2-3 hrs. Remove the slides from the SAT(PEG4) solution and transfer to a slide washing dish containing anhydrous chloroform. Sonicate the slides for 15 minutes by immersing washing dish to ⅔ its height in tap water. Transfer the slides to a second washing dish and rinse each with ethanol, then with diH$_2$0, Set cleaned SAT(PEG4) slides in vacuum oven at 37° C./20 inches Hg until dry (30 to 60 min).

Add 15 μL per well of deacylation solution containing 1 mg/ml maleimido-C3-NTA. Incubate 20 minutes at room temp under glass cover. Wash thoroughly with diH$_2$0. Add 15 μL, per well of 100 mM NiCl$_2$/Tris pH7.2 solution. Incubate 10 minutes at room temp. Wash wells by submersion in Loading Buffer required by specific experiment. Agitate with 200 μL pipettor. (However, if PBS is required by the experiment, wash NiCl$_2$/Tris pH7.2 solution out of wells with H₂O first, then wash with required buffer). Keep wells hydrated at all times with appropriate buffer.

Load the protein of interest that is first spin-filtered to remove any aggregates by making a 2× stock and mixing 1:1 into required Loading Buffer (0.1M Tris, buffer pH 8.0 20 mM NaCl). Labeled protein is loaded onto a slide surface at a concentration of 5 uM for 20-45 minutes. Wash loaded wells of slide with measurement buffer containing a concentration of DMSO matched to the incoming bolus of compounds (in this example, assay buffer was supplemented with 0.2% DMSO). Perform dilution washes at least 6 times to remove unbound labeled protein. Known type I kinase inhibitor dasatinib, known type II inhibitor imatinib, and unclassified kinase inhibitor (with respect to Abl kinase) saracatinib are added to the templated wells to a final concentration of 10 uM. All stock solutions of compounds are formulated at 10 mM in DMSO. Stocks are diluted into assay buffer at 2× final concentration (20 uM) then added to wells in a 1:1 mixture.

SHG Detection

A beam from a Ti:S femtosecond laser is used as the fundamental according to procedures known to those skilled in the art. Specifically, an argon-pumped Ti:sapphire system operating at 80 MHz with ~150 fs pulse duration and 0.5 W average power was employed (Coherent, Inc.). The beam is preferentially focused to a spot at the slide-buffer interface. Second harmonic light generated by the surface is collected, filtered from the fundamental, and detected by a photomultiplier tube (PMT) according to procedures known to those skilled in the art. A baseline signal with declining intensity due to photobleaching is recorded. The polarization of the fundamental beam is varied to produce the maximum signal output. The polarization of both the fundamental and second-harmonic beams is varied using wave plates. The signal is verified as the second-harmonic by determining its quadratic dependence on the fundamental intensity and measuring its characteristic spectral lineshape. Each data point is obtained by using a photon counting 1-second integration time.

Results

Figure 3:
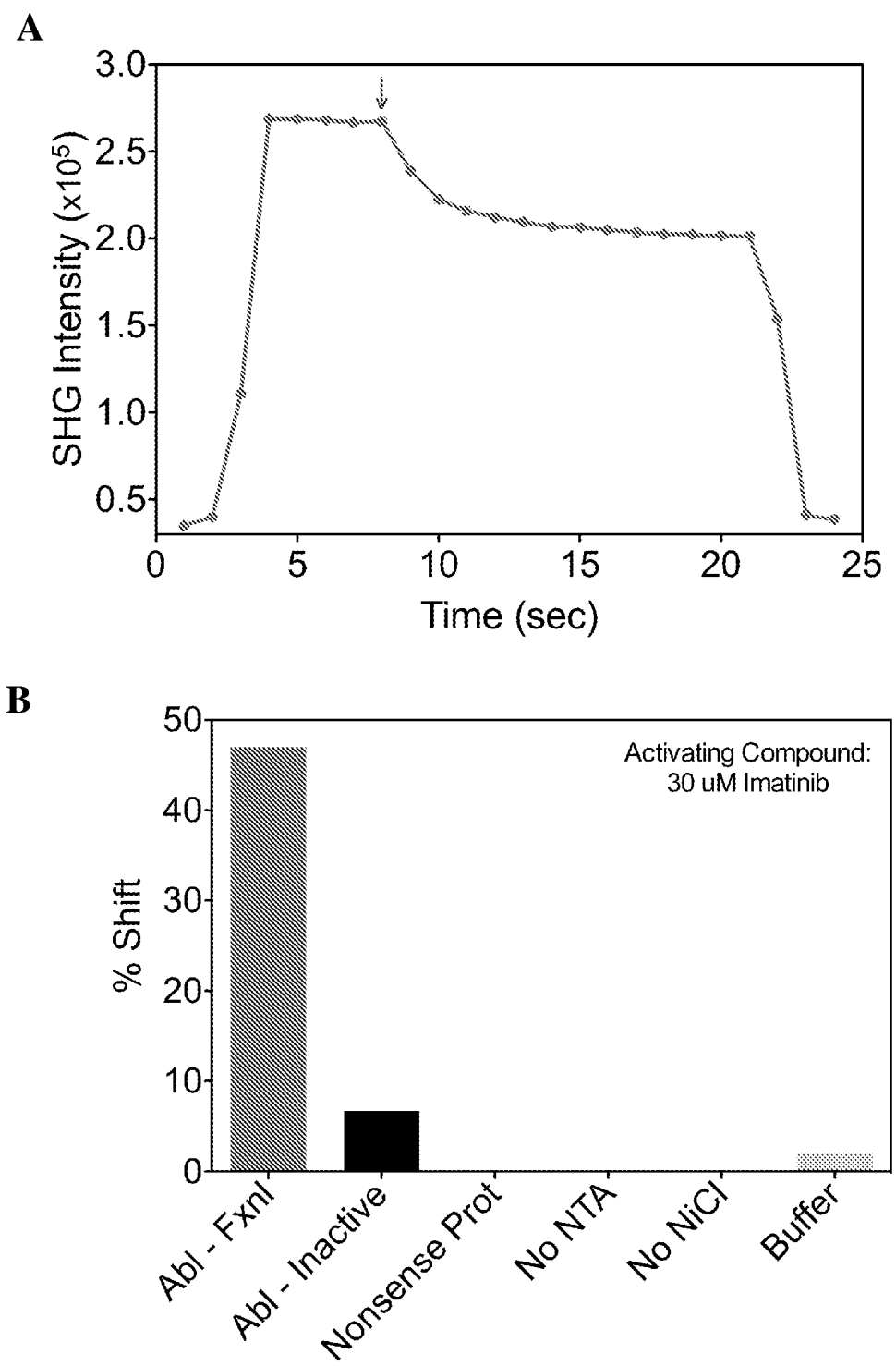
FIG. 3 depicts SHG responses are target protein dependent. Treating Abl kinase with 30 µM of the type II inhibitor imatinib generates a characteristic kinetic response (A). This response is dependent on the presence of functional Abl kinase properly presented for SHG analysis (B). (Abl-Fxnl=Functional Abl kinase; Abl-Inactive=inactivated Abl kinase; Nonsense Prot=surface loaded with nonsense protein; No NTA and No NiCl=reagents absent from surface preparation).
Figure 4:
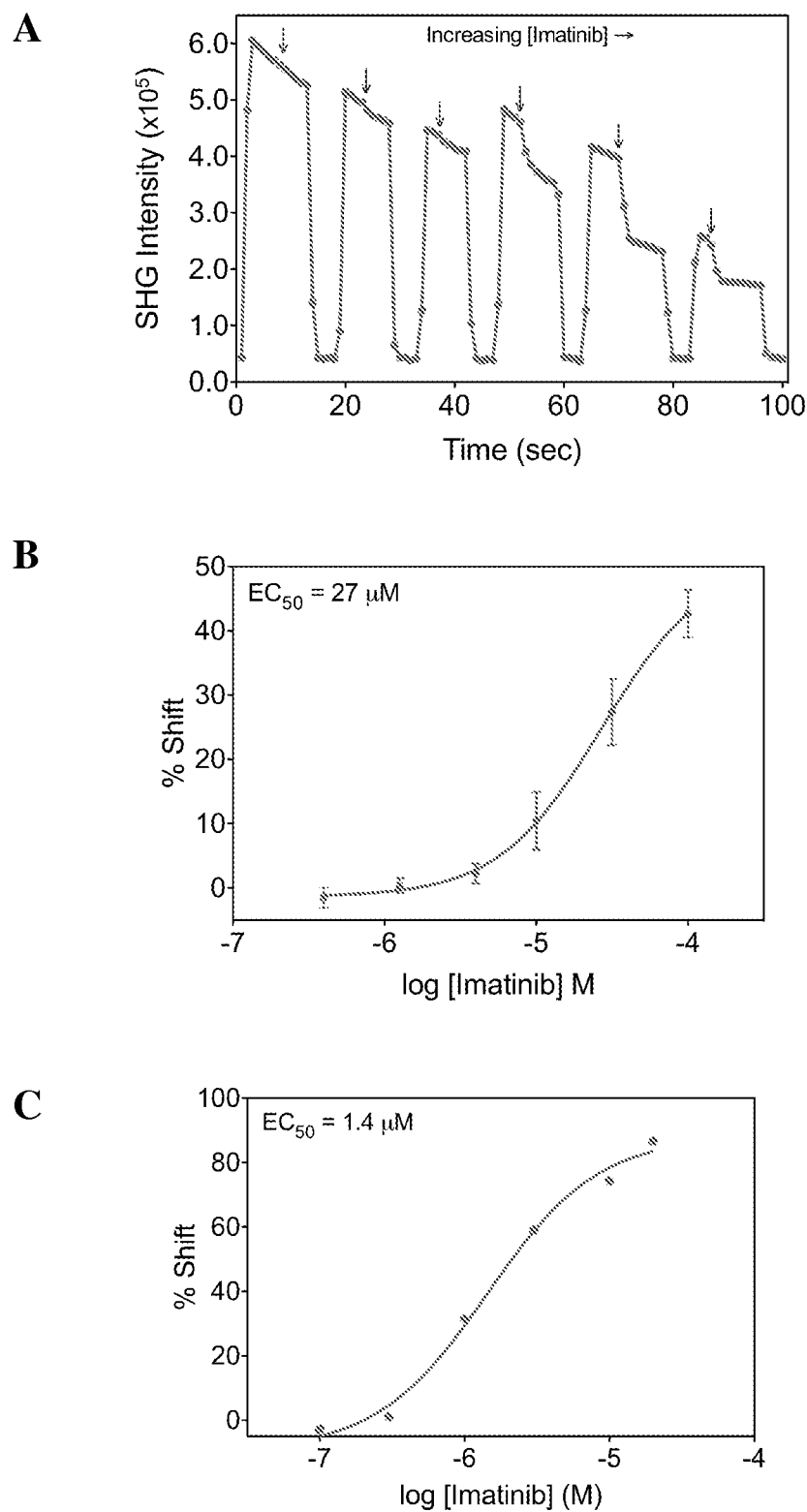
FIG. 4 depicts SHG assay characterization of kinase inhibitor compounds in both kinetic and endpoint modes. Imatinib concentration response curves are recorded in real-time, kinetic mode (A) with responses measured 5 sec after ligand addition. From these data, kinetic response features are established and a preliminary $EC_{50}$ derived (B). Endpoint assays (20 minutes after ligand addition) are subsequently performed (C), which permit the binding interaction to approach chemical equilibrium, and results in an $EC_{50}$ closer to the known Kd of Imatinib (300 nM)[5].

Treating labeled Abl kinase with 30 μM the type II inhibitor imatinib generated a characteristic SHG response (FIG. 3A). This response was dependent upon the presence of a functional Abl kinase, as there was no observed shift when imatinib was added to an inactive Abl kinase or when the surface was loaded with a nonsense protein (FIG. 3B). Concentration response curves for increasing concentrations of imatinib over time were recorded with responses measured 5 seconds after the addition of the inhibitor (FIG. 4A). From this data, an $EC_{50}$ of 27 μM was calculated (FIG. 4B). Endpoint assays performed 20 minutes after the addition of imatinib permitted the reaction to approach equilibrium and resulted in an $EC_{50}$ of 1.4 μM (FIG. 4C). Therefore, SHG detection confirms that imatinib binds in a bimolecular fashion to Abl kinase and confirms the measured responses are specific to functional Abl. Applying SHG in both kinetic and endpoint modes enables a more comprehensive characterization of compounds under investigation.

Addition of 10 μM of the type I inhibitor dasatinib produced no change in the second harmonic signal or the surface without protein (FIG. 5B). Similar to above, addition of 10 μM of the type II inhibitor imatinib, produces a significant change in the signal (FIG. 5A) but no change in signal with the surface alone, thereby indicating the assay can selectively identify type II compounds. Addition of 10 μM saracatinib, an unclassified kinase inhibitor, showed a response characteristic of the type II inhibitor imatinib, thereby confirming that this compound is a type II inhibitor with respect to Abl kinase. Responses for all three inhibitor compounds were quantified and compared to buffer control to demonstrate that dasatinib did not generate a significant response (FIG. 5C). However, when imatinib was pre-incubated with both type I and type II inhibitor compounds, the imatinib responses were blocked (FIG. 5D). This suggests that type I and type II kinase inhibitors occupy overlapping sites within the structure of Abl kinase. Significant differences between responses to the known type I and II inhibitors are observed. Interestingly, the similarities between the SHG kinetic data for imatinib and saracatinib indicates that the previously uncharacterized saracatinib is a type II Abl inhibitor.

These studies support SHG as a powerful assay for the discovery and evaluation of type I and type II kinase inhibitor compounds. Additionally, overall, this example indicates that type I and type II kinase inhibitors occupy overlapping binding sites within Abl kinase.

Example 2

Immobilization of the Kinase onto a Supported Lipid Bilayer Surface

Kinase proteins can also be detected by linking them to supported lipid bilayers. The protocol for making supported bilayers can be found in the literature. Several protocols exist, such as the ones described in Nye and Groves, *Langmuir*, 2008, 24(8): 4145-4149 (the contents of which are incorproated by reference herein with respect to teachings regarding production of lipid bilayers). A number of methods for producing supported lipid bilayers are known in the art. This example demonstrates that kinases can be immobilized on a lipid bilayer for detection with SHG.

Materials and Methods

The following Materials and Methods are used in the examples described above.

Glassware Cleaning and Preparation of Small Unilammelar Vesicles (SUVs)

All glass slides or glassware are cleaned with Piranha wash (20 minutes) prior to starting. A solution is prepared in heat-safe glassware (such as pyrex) in a fume hood. Measure out 30 ml of a 30% $H_2O_2$ solution first, then add 70 ml concentrated sulfuric acid to it. Rinse vacuum bottles with Chloroform ($CHCl_3$)

Determine the desired molar ratio of DOPC lipid to DGS NTA(Ni) while avoiding exposure to air. A vacuum bottle with lipid mix is then placed onto a Rotovap evaporator and evaporated until dry (about 30 seconds). $N_2$ gas is blown over the evaporated preparation for 10 min to remove any residual $CHCl_3$. The lipid mixture is then resuspended in 2 mL of $diH_2O$ and vortexed vigorously until a cloudy suspension forms (about 5 minutes). The suspension is transferred to a 4 mL polystyrene test tube and the lipid mixture sonicated on ice until the solution clears. This should require about 60 to 90 seconds with the sonicator set to 25% power. The sonicated lipid solution is then transferred into microcentrifuge tubes and centrifuged at 17,000×G for 30 minutes at 4° C. The supernatant is transferred into clean microcentrifuge tubes and stored at 4° C. The vesicles are stable for about 1 month.

Slide Preparation and Protein Loading

Immediately before applying DOPC/DGS NTA (Ni) SUVs, clean microscope slides with Piranha wash for 20 minutes. Rinse 3× with diH$_2$O in a slide staining vessel. Dry slides with compressed Nitrogen. Assemble SHG wells by attaching adhesive gaskets to Piranha-cleaned slides (i.e., 16 wells per slide containing 10-20 µl volume). Use assembly jig to align gaskets, carefully lay slide into jig and press firmly. Dilute DOPC/DGS NTA (Ni) lipid prep 1:1 with PBS or TBS buffers. 100 mM NaCl is required to reduce hydrostatic charge of the glass slide and enable the SLB to form. Pipet 10 µL of diluted DOPC/DGS NTA (Ni) SUVs into wells of slide. Incubate for 5 minutes at room temperature. (SLB are stable in the wells for 2 days at 4° C.). Taking care not to introduce air into the wells at any time, wash wells by submersing slide in buffer bath (PBS or TBS) and agitating with a 200 µL pipettor. Exchange entire volume of buffer in bath with fresh buffer and repeat washing step 2 more times. Add a 1:1 volume of 100 mM NiCl$_2$ solution to all wells. Incubate 10 minutes at room temperature. Wash wells by submersing slide in buffer bath (PBS or TBS) and agitating with a 200 µL pipettor. Exchange entire volume of buffer in bath with fresh buffer and repeat washing step 2 more times. If necessary, exchange buffer in wells to appropriate protein loading buffer. Load target protein of interest onto wells. Incubate 30 to 90 minutes at room temperature. Rinse wells thoroughly with assay buffer before starting experiments.

SUVs are applied over Piranha-washed Fisher slides to make the SLB surface. NiCl$_2$ was added for 10 minutes and wells were washed in labeling buffer.

Labeled Abl kinase is then prepared and applied to the surface as described in the example above.

Labeled Abl kinase is loaded onto the SLB surface prepared as described above at 3 µM for 45 minutes, followed by washing. If imidazole is added, the signal drops indicating that attachment to the surface occurs via the protein's His-tag. If supported bilayers are prepared without inclusion of the Ni-NTA lipid, little to no signal is produced above the background signal upon addition of the labeled protein to the well.

Results

Figure 6:
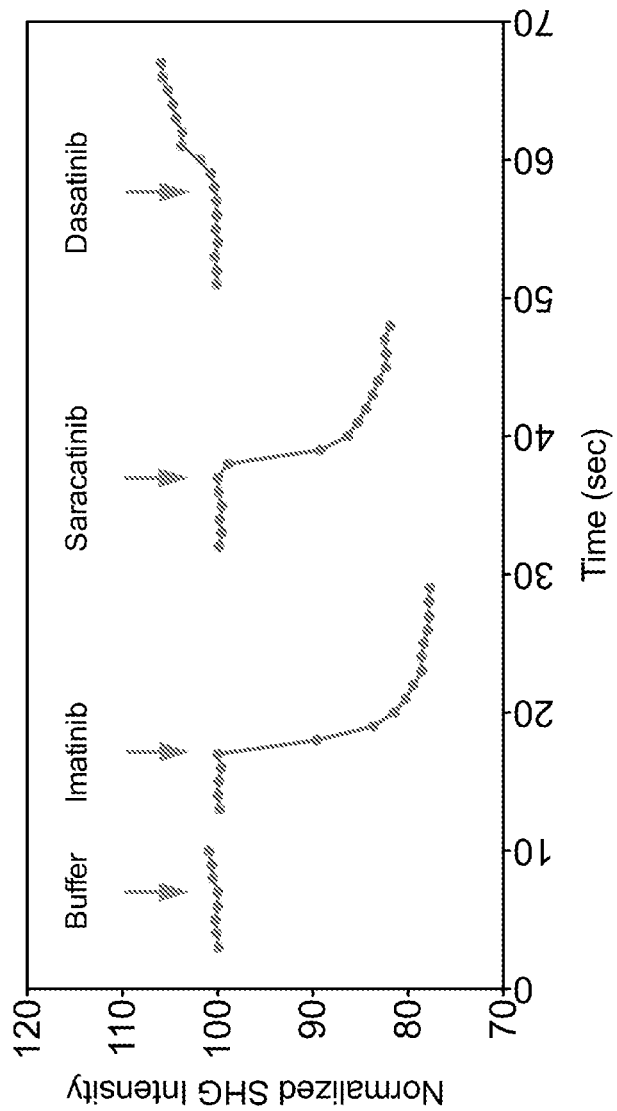
FIG. 6 depicts SHG response of Abl kinase immobilized on a lipid bilayer to three kinase inhibitors.

FIG. 6 shows that labeled Abl kinase can be detected by SHG on the supported lipid bilayer. Exposure of the protein to buffer, imatinib, saracatinib or dasatinib produce characteristic SHG responses in real time.

These studies show that SHG can be used to assay for the discovery and evaluation of type I and type II kinase inhibitor compounds using kinases immobilized on a lipid bilay

REFERENCES

1 Salafsky, J. S. 'SHG-labels' for detection of molecules by second harmonic generation. *Chemical Physics Letters* 342, 485-491 (2001).
2 Salafsky, J. S. Second-harmonic generation as a probe of conformational change in molecules. *Chemical Physics Letters* 381, 705-709 (2003).
3 Salafsky, J. S. Detection of protein conformational change by optical second-harmonic generation. *Journal of Chemical Physics* 125 (2006).
4 Liu, Y. & Gray, N. S. Rational design of inhibitors that bind to inactive kinase conformations. *Nature Chem. Biol.* 2, 358-364 (2006).
5 Zhang, J., Yang, P. L. & Gray, N. S. Targeting cancer with small molecule kinase inhibitors. *Nature Reviews Cancer* 9, 28-39, doi:10.1038/nrc2559 (2009).
6 Noble, M. E. M., Endicott, J. A. & Johnson, L. N. Protein kinase inhibitors: Insights into drug design from structure. *Science* 303, 1800-1805 (2004).
7 Schindler, T. et al. Structural Mechanism for STI-571 Inhibition of Abelson Tyrosine Kinase. *Science* 289, 1938-1942 (2000).
8 Pargellis, C. et al. Inhibition of p38 MAP kinase by utilizing a novel allosteric binding site. *Nature Structural Biology* 9, 268-272 (2002).
9 Schindler, T. Structural mechanism for STI-571 inhibition of abelson tyrosine kinase. *Science* 289, 1938-1942 (2000).
10 Shan, Y. B. et al. A conserved protonation-dependent switch controls drug binding in the Abl kinase. *Proceedings of the National Academy of Sciences of the United States of America* 106, 139-144 (2009).
11 Kufareva, I. & Abagyan, R. Type-II Kinase Inhibitor Docking, Screening, and Profiling Using Modified Structures of Active Kinase States. *Journal of Medicinal Chemistry* 51, 7921-7932 (2008).
12 Annis, D. A., Nazef, N., Chuang, C.-C., Scott, M. P. & Nash, H. M. A General Technique To Rank Protein, àíLigand Binding Affinities and Determine Allosteric versus Direct Binding Site Competition in Compound Mixtures. *Journal of the American Chemical Society* 126, 15495-15503, doi:10.1021/ja048365x (2004).
13 Vogtherr, M. et al. NMR Characterization of Kinase p38 Dynamics in Free and Ligand-Bound Forms. *Angewandte Chemie International Edition* 45, 993-997 (2006).
14 Hubbard, S. R., Mohammadi, M. & Schlessinger, J. Autoregulatory mechanisms in protein-tyrosine kinases. *Journal of Biological Chemistry* 273, 11987-11990 (1998).
15 Huse, M. & Kuriyan, J. The conformational plasticity of protein kinases. *Cell* 109, 275-282 (2002).
16 Nagar, B. et al. Crystal structures of the kinase domain of c-Abl in complex with the small molecule inhibitors PD173955 and imatinib (STI-571). *Cancer Research* 62, 4236-4243 (2002).
17 Seeliger, M. A. et al. High yield bacterial expression of active c-Abl and c-Src tyrosine kinases. *Protein Science* 14, 3135-3139 (2005).
18 Sicheri, F. & Kuriyan, J. Structures of Src-family tyrosine kinases. *Current Opinion in Structural Biology* 7, 777-785 (1997).
19 Sicheri, F., Moarefi, I. & Kuriyan, J. Crystal structure of the Src family tyrosine kinase Hck. *Nature* 385, 602-609 (1997).
20 Xu, W. Q., Doshi, A., Lei, M., Eck, M. J. & Harrison, S. C. Crystal structures of c-Src reveal features of its autoinhibitory mechanism. *Molecular Cell* 3, 629-638 (1999).
21 Xu, W. Q., Harrison, S. C. & Eck, M. J. Three-dimensional structure of the tyrosine kinase c-Src. *Nature* 385, 595-602 (1997).
22. Shan Y B, Seeliger M A, Eastwood M P, Frank F, Xu H F, Jensen M O, et al. A conserved protonation-dependent switch controls drug binding in the Abl kinase. Proceedings of the National Academy of Sciences of the United States of America. 2009; 106(1):139-44.
23. Seeliger M A, Ranjitkar P, Kasap C, Shan Y B, Shaw D E, Shah N P, et al. Equally Potent Inhibition of c-Src and Abl by Compounds that Recognize Inactive Kinase Conformations. Cancer Research. 2009; 69(6):2384-92.
24. Seeliger M A, Young M, Henderson M N, Pellicena P, King D S, Falick A M, et al. High yield bacterial expression of active c-Abl and c-Src tyrosine kinases. Protein Science. 2005; 14(12):3135-9.

We claim:

1. A method for classifying a kinase inhibitor as a type I or type II kinase inhibitor based on a conformational change that the kinase inhibitor induces in the structure of a kinase labeled with a second harmonic-active label, wherein the label has a net orientation at an interface, the method comprising:
   a. contacting the kinase with a kinase inhibitor, wherein the kinase specifically interacts with said kinase inhibitor;
   b. detecting an interaction between the kinase and said kinase inhibitor in solution and in real-time by measuring a first signal or signal change generated by the second harmonic-active label using a surface-selective technique, wherein the first signal or signal change indicates a conformational change in the structure of the kinase that is specific for the kinase inhibitor; and
   c. classifying the kinase inhibitor as a type I or type II kinase inhibitor by comparing the first signal or signal change of (b) with a second signal or signal change detected by an interaction between the kinase and a known type I or type II inhibitor of the kinase, wherein the second signal or signal change indicates a conformational change in the structure of the kinase that is specific for the known type I or type II inhibitor of the kinase.

2. The method of claim 1, wherein the kinase comprises an affinity tag.

3. The method of claim 1, wherein the conformational change in the structure of the kinase is detected in real time.

4. The method of claim 1, wherein the kinase inhibitor is a small molecule chemical compound, a non-antibody inhibitory peptide, an antibody, or any combination thereof.

5. The method of claim 1, wherein the second harmonic-active label is bound to the kinase by one or more sulfhydryl groups on the surface of the kinase.

6. The method of claim 5, wherein said one or more sulfhydryl groups are native sulfhydryl groups.

7. The method of claim 5, wherein said one or more sulfhydryl groups are engineered sulfhydryl groups.

8. The method of claim 5, wherein said one or more sulfhydryl groups are not located within the kinase activation loop.

9. The method of claim 1, wherein the second harmonic-active label is an unnatural amino acid.

10. A method for classifying an unknown candidate kinase inhibitor as a type I or type II kinase inhibitor based on a conformational change that the candidate kinase inhibitor induces in the structure of a kinase labeled with a second harmonic-active label, wherein the label has a net orientation at an interface, and wherein the kinase has no known type I or type II inhibitors, the method comprising:
   a. contacting the kinase with the candidate kinase inhibitor, wherein the kinase specifically interacts with said candidate kinase inhibitor;
   b. detecting an interaction between the kinase and said candidate kinase inhibitor in solution and in real-time by measuring a signal or signal change generated by the second harmonic-active label using a surface-selective technique, wherein the signal or signal change indicates a conformational change in the structure of the kinase that is specific for the candidate kinase inhibitor; and
   c. comparing the signal or signal change detected in (b) with a signal or signal change produced by the interaction between a known type I or type II kinase inhibitor and a kinase known to be inhibited by said known type I or type II kinase inhibitor to classify the candidate kinase inhibitor based on the conformational change it induces in the structure of the kinase.

11. A method for classifying a first kinase inhibitor as a type I or type II kinase inhibitor based on a conformational change that the first kinase inhibitor induces in the structure of a first kinase labeled with a first second harmonic-active label, wherein the label has a net orientation at an interface, the method comprising:
  a. contacting the first kinase with a first kinase inhibitor, wherein the first kinase specifically interacts with said first kinase inhibitor;
  b. detecting an interaction between the first kinase and said first kinase inhibitor in solution and in real-time by measuring a first signal or signal change generated by the first second harmonic-active label using a surface-selective technique, wherein the first signal or signal change indicates a conformational change in the structure of the first kinase that is specific for the first kinase inhibitor; and
  c. classifying the first kinase inhibitor as a type I or type II kinase inhibitor by comparing the first signal or signal change of (b) with a second signal or signal change detected by an interaction between a second kinase and a known type I or type II inhibitor of the second kinase, wherein the second signal or signal change indicates a conformational change in the structure of the second kinase that is specific for the known type I or type II inhibitor of the second kinase.

12. The method of claim 11, wherein the first kinase has no other known kinase inhibitors.

13. The method of claim 11, further comprising comparing a profile of the first signal or signal change to a profile of the second signal or signal change.

14. The method of claim 11, wherein the kinase is attached to a surface.

15. The method of claim 14, further comprising contacting the kinase attached to the surface with imidazole.

16. The method of claim 15, further comprising measuring a signal or signal change generated by the second harmonic-active label using the surface-selective technique, wherein the signal or signal change indicates a specific interaction of the kinase with the surface.

17. The method of claim 11, further comprising mass-spectrometrically confirming that a residue in the kinase is labeled by the second harmonic-active label.

18. The method of claim 11, wherein the kinase is labeled with a second second harmonic-active label that is distinguishable from the first second harmonic-active label.

* * * * *

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: misc_feature
<222> LOCATION: (1)..(20)
<223> OTHER INFORMATION: This sequence may encompass 1-20 "His" residues

<400> SEQUENCE: 2

His His His His His His His His His His His His His His His His
1               5                   10                  15

His His His His
            20
```